US006440996B1

(12) United States Patent
Kozikowski et al.

(10) Patent No.: US 6,440,996 B1
(45) Date of Patent: Aug. 27, 2002

(54) MONOMERIC AND DIMERIC HETEROCYCLES, AND THERAPEUTIC USES THEREOF

(75) Inventors: Alan P. Kozikowski, Princeton, NJ (US); Gian Luca Araldi, San Diego, CA (US); Amir P. Tamiz, Washington, DC (US)

(73) Assignee: Georgetown University, Washington, DC (US)

( * ) Notice: Subject to any disclaimer, the term of this patent is extended or adjusted under 35 U.S.C. 154(b) by 0 days.

(21) Appl. No.: 09/414,106

(22) Filed: Oct. 7, 1999

Related U.S. Application Data

(60) Provisional application No. 60/103,460, filed on Oct. 7, 1998, and provisional application No. 60/103,423, filed on Oct. 7, 1998.

(51) Int. Cl.[7] .................. A61K 31/445; A61K 31/4523; C07D 271/06; C07D 309/10; C07D 401/02
(52) U.S. Cl. ...................... 514/316; 514/326; 514/332; 546/186; 546/187; 546/189; 546/191; 546/209; 546/228; 548/131; 549/425; 549/426
(58) Field of Search ................................ 546/186, 189; 514/332; 548/131; 549/425, 426

(56) References Cited

FOREIGN PATENT DOCUMENTS

| DE | 240 411 3 | 8/1974 |
|----|-----------|--------|
| EP | 0639 568 A1 | 2/1995 |
| WO | WO 98/45263 | 10/1998 |

OTHER PUBLICATIONS

Clarke et al., "Compounds Affecting the Central Nervous System. 4.3β–Phenyltropane–2–carboxylic Esters and Analogs", Journal of Medicinal Chemistry 16(11):1260–1267 (1973).

Clarke et al., "In Pursuit of Analgetic Agents. Hydro–1, 3–ethanoindeno[2,1–c]pyridines and Homologs", Journal of Medicinal Chemistry 17(10):1040–1046 (1974).

Kozikowski et al., "Chemistry and Pharmocology of the Piperidine–Based Analogues of Cocaine. Identification of Potent DAT Inhibitors Lacking the Tropane Skeleton", Journal of Medicinal Chemistry 41:1962–1969 (1998).

Lambrecht and Mutschler, "Structur–Wirkungs–Beziehungen Von Aromatisch Substituierten Piperidin–Derivaten, 1.Mitt.(Structure–Activity–Relationship of Aromatic Substituted Piperidine Derivatives", Archiv Der Pharmazie , De, VCH Verlagssellschaft MBH, Weinheim, 308 (9): 676–67 (1975).

Reith et al., "Structural Requirements for Cocaine Congeners to Interact with [³H]Batrachotoxinin A 20–α–Benzoate Binding Sites on Sodium Channels in Mouse Brain Synaptosomes", The Journal of Biological Chemistry, 261 (16):7300–7305 (1986).

Reith and Coffey., "Structure–Activity Relationships for Cocaine Congeners in Inhibiting Dopamine Uptake into Rat Brain Synaptic Vesicles and Bovine Chromaffin Granule Ghosts [1]", Journal of Pharmacology and Experimental Therapeutics, 271 (3): 1444–1452 (1994).

*Primary Examiner*—T. A. Solola
(74) *Attorney, Agent, or Firm*—Dana M. Gordon; Foley Hoag LLP

(57) ABSTRACT

The invention provides compounds of formula (I):

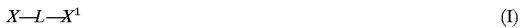

X—L—X¹  (I)

wherein X and X¹ are substituted piperidine, cyclohexane, or tetrahydropyran rings, and L is a linking group between X and X¹; as well a pharmaceutical composition comprising a compound of formula I; intermediates and methods useful for preparing a compound of formula I; and therapeutic methods for treating drug addiction, Parkinson's disease, depression, or a disease wherein the administration of cocaine is indicated, comprising administering a compound of formula I or a pharmaceutically acceptable salt thereof to a mammal in need of such treatment.

34 Claims, 26 Drawing Sheets

| Compd # | B | Spacer | Isomer | [³H]DA Uptake $K_i$ (nM) | [³H]NE Uptake $K_i$ (nM) | [³H]5-HT Uptake $K_i$ (nM) | Selectivity NET/DAT | NET/HTT |
|---|---|---|---|---|---|---|---|---|
| Cocaine | - | - | (+)-cis | 423 ± 147 | 108 ± 3.5 | 155 ± 0.4 | 0.26 | 0.70 |
| 4 | - | - | (-)-cis | 69 ± 8 | 88 ± 3 | 391 ± 27 | 1.28 | 0.23 |
| 6 | - | - | (+)-trans | 228 ± 30 | 90 ± 5 | 5880 ± 440 | 0.39 | 0.015 |
| 10 | O | -(CH₂)₅- | (+)-trans | 56 ± 5 | 182 ± 8 | 25 ± 5.4 | 3.3 | 7.3 |
| 11 | O | -(CH₂)₃- | (+)-trans | 108 ± 10 | 340 ± 2 | 730 ± 68 | 3.1 | 0.46 |
| 12 | O | -(CH₂)₈- | (+)-trans | 142 ± 4 | 658 ± 88 | 174 ± 4 | 4.6 | 3.8 |
| 13 | O | p-Ph-p | (+)-trans | 333 ± 15 | 1590 ± 220 | 1180 ± 120 | 4.8 | 1.3 |
| 14 | O | p-Ph-Ph-p | (+)-trans | 967 ± 96 | 1660 ± 50 | 137 ± 17.1 | 1.7 | 12 |
| 16 | NH | -(CH₂)₅- | (+)-trans | 39 ± 4 | 158 ± 15 | 7.0 ± 0.6 | 4.0 | 22 |
| 17 | NH | -(CH₂)₅- | (-)-trans | 1960 ± 200 | 393 ± 7 | 1.0 ± 0.1 | 0.2 | 393 |
| 18 | NH | -(CH₂)₄- | (+)-trans | 33 ± 6 | 104 ± 7.6 | 534 ± 41 | 3.1 | 0.19 |
| 22 | NH | -(CH₂)₆- | (+)-trans | 75 ± 8 | 579 ± 28 | 60 ± 2 | 7.7 | 9.7 |

MONOMERIC AND DIMERIC HETEROCYCLES, AND THERAPEUTIC USES THEREOF

RELATED APPLICATIONS

This application claims the benefit of priority to U.S. Provisional Patent Application No. 60/103,460, filed Oct. 7, 1998, the specification of which is hereby incorporated by reference; and U.S. Provisional Patent Application No. 60/103,423, filed Oct. 7, 1998, the specification of which is hereby incorporated by reference.

GOVERNMENT FUNDING

The invention described herein was made with U.S. Government support under grant DA11546, awarded by the National Institutes of Health, National Institute on Drug Abuse.

BACKGROUND OF THE INVENTION

Cocaine abuse is one of the greatest concerns of the American public today, and has therefore become a focus of medical, social and political leaders. Cocaine is one of the most addictive substances known, and addicts may lose their ability to function at work or in interpersonal situations. Drug dependence and the great profits that are made throughout the distribution network of cocaine have fueled a rise in drug-associated crime in the United States and in Colombia. Although the incidence of casual cocaine use has decreased substantially in the last few years, the number of weekly users is rising. The rise has accompanied a change in the chemical form often used to free base, or "crack," and the route of administration used from nasal to inhalation by smoking or intravenous injection.

Psychological and behavioral approaches are important in a treatment program because peer pressure and environmental cues are closely associated with a relapse to addiction. However, behavioral observations have identified a window of about ten weeks after cessation of cocaine use where the susceptibility to relapse is greatest. Clearly, there is a need to increase the success rate of outpatient detoxification programs through the development of pharmacological agents that will assist during this critical period.

Currently a number of treatment strategies are being looked at using CNS agents developed for other indications. The agents being tried include, among others, the indirect dopamine agonist, amantadine, the direct agonist bromocriptine, the partial mu opiate receptor agonist, buprenorphine, and the tricyclic antidepressant, desipramine. While these agents appear to depress either self-administration or cocaine "craving" under certain circumstances, these studies are still in their early stages and the efficacy of such treatments has not been established.

The behavioral properties of cocaine, including its abilities to act as a reinforcer, are thought to stem from its ability to inhibit the reuptake of dopamine (DA). While cocaine also has the ability to act as an inhibitor of serotonin and norepinephrine uptake as well as to bind to sigma opiate and muscarinic receptors, the potencies of cocaine and analogs in self-administration studies correlate best with their DA transporter inhibitor activities. Unfortunately, the precise mechanism by which cocaine inhibits dopamine uptake is still uncertain. Several laboratories have shown that cocaine inhibition of dopamine uptake into striatal synaptosomes is consistent with a classic, fully competitive mechanism. However these data are also consistent with more complex models, including allosteric or partially competitive, and several others involving steric hindrance, distinct but overlapping sites or multiple binding sites in which at least one is required for both cocaine and dopamine binding. In addition, a recent study using rotating disk electrode voltammetry, which is capable of monitoring uptake with a 50 msec resolution, suggests that cocaine inhibits dopamine uptake uncompetitively while competitively blocking $Na^+$ and $Cl^-$ binding to the carrier. While these data have not been validated using other experimental approaches, they further support the idea that the cocaine and dopamine binding sites are unique.

N-Ethyhmaleimide (NE) is capable of inhibiting about 95% of the specific binding of [$^3$H]mazindol, and the effect of 10 mM N-ethyhmaleimide is completely prevented by 10 $\mu$M cocaine, while neither 300 $\mu$M dopamine nor d-amphetamine afforded any significant protection. Furthermore, a recent study of the structure of the dopamine transporter revealed that aspartate and serine residues lying within the first and seventh hydrophobic putative membrane spanning regions were critical for dopamine uptake, but less so for [$^3$H]CFT (WIN-35428) binding. For example, replacement of the serine residues at positions 356 and 359 in the seventh hydrophobic region by alanine or glycine reduced [$^3$H]DA uptake, whereas [$^3$H]CFT (WIN-35428) binding was less affected. More recent experiments with DA and NE transporter chimeras show that transmembrane domains 6–8 determine cocaine binding while domains 9–12 plus the carboxy tail are responsible for DA binding affinity. Thus, these data support the hypothesis that a significant portion of the cocaine binding domain on the dopamine transporter is distinct from that of either dopamine or amphetamine. This distinction may be sufficient to allow properly designed drugs to prevent cocaine binding without inhibiting dopamine uptake.

The most promising agents for treating cocaine abuse, may be agents which possess the ability to mimic partially the effects of cocaine, thereby helping to maintain individuals in treatment programs while they slowly withdraw from cocaine. Such an agent would function like methadone, a drug widely used in the treatment of opiate abuse. A compound with methadone-type activity against cocaine abuse is likely to be a partial agonist of cocaine; namely, a substance that elicits some of the same effects in the user as cocaine itself, but without causing the same degree of euphoria. Ideally, the compound should have little or no abuse liability.

Thus there is currently a need for safe and effective therapeutic agents for treating cocaine abuse.

SUMMARY OF THE INVENTION

The present invention provides a compound of formula (I):

(I)

wherein X and $X^1$ are each independently a compound of formula II

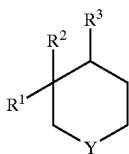

(II)

wherein:
Y is $NR^6$, —$C(R^4)(R^5)$—, or —O—;
$R^1$ is —$C(=O)OR_a$, cyano, $(C_1-C_6)$alkyl, $(C_1-C_6)$alkanoyl, $(C_2-C_6)$alkenyl, $(C_2-C_6)$alkynyl, or 1,2,4-oxadiazol-5-yl optionally substituted at the 3-position by W, wherein any $(C_1-C_6)$alkyl, $(C_1-C_6)$alkanoyl, $(C_2-C_6)$alkenyl, or $(C_2-C_6)$alkynyl may optionally be substituted with 1, 2 or 3 substituents independently selected from the group consisting of halo, nitro, cyano, hydroxy, $(C_1-C_6)$alkoxy, $(C_2-C_6)$acyloxy, trifluoromethyl, $C(=O)OR_b$, $C(=O)NR_cR_d$, $NR_eR_f$, and $S(=O)_nR_g$; and $R^3$ is $(C_6-C_{10})$aryl, 5–10 membered heteroaryl, $(C_6-C_{10})$aryl$(C_1-C_6)$alkyl, 5–10 membered heteroaryl$(C_1-C_6)$alkyl, $(C_6-C_{10})$arylcarbonyl, biphenyl, or 5–10 membered heterylcarbonyl, wherein any aryl, biphenyl, or heteroaryl substituent may optionally be substituted on carbon with 1, 2 or 3 substituents independently selected from the group consisting of halo, nitro, cyano, hydroxy, $(C_1-C_6)$alkyl, $(C_2-C_6)$alkenyl, $(C_2-C_6)$alkynyl, $(C_1-C_6)$alkoxy, $(C_2-C_6)$acyloxy, trifluoromethyl, $C(=O)OR_b$, $C(=O)NR_cR_d$, $NR_eR_f$, and $S(=O)_nR_g$; or
$R^1$ is —$CH_2$—, or —$CH_2CH_2$—, wherein $R^1$ is attached to a carbon at the ortho position of $R^3$; and $R^3$ is $(C_6-C_{10})$aryl, or 5–10 membered heteroaryl;
$R^2$ is hydrogen or $(C_1-C_6)$alkyl;
$R^4$ and $R^5$ are independently hydrogen or $(C_1-C_6)$alkyl;
$R^6$ is hydrogen, $(C_1-C_6)$alkyl, $(C_1-C_6)$alkanoyl, $(C_2-C_6)$alkenyl, $(C_2-C_6)$alkynyl, trifluoromethyl, aryl, heteroaryl, aryl$(C_1-C_4)$alkyl, heteroaryl$(C_1-C_4)$alkyl, aryl$(C_1-C_4)$alkanoyl, or heteroaryl$(C_1-C_4)$alkanoyl; wherein any $(C_2-C_6)$alkyl, $(C_2-C_6)$alkanoyl, $(C_2-C_6)$alkenyl, or $(C_2-C_6)$alkynyl may optionally be substituted on a carbon other than the carbon attached to the piperidine nitrogen with 1, 2 or 3 substituents independently selected from the group consisting of nitro, cyano, hydroxy, $(C_1-C_6)$alkoxy, $(C_2-C_6)$acyloxy, trifluoromethyl, $C(=O)OR_b$, $C(=O)NR_cR_d$, and $S(=O)_nR_g$;
each n is independently 0, 1 or 2;
W is $(C_1-C_6)$alkyl, or aryl, optionally substituted with 1, 2, or 3 substituents independently selected from the group consisting of halo, nitro, cyano, hydroxy, $(C_1-C_6)$alkoxy, $(C_2-C_6)$acyloxy, trifluoromethyl, $C(=O)OR_b$, $C(=O)NR_cR_d$, $NR_eR_f$, and $S(=O)_nR_g$;
$R_a$ is hydrogen, $(C_1-C_4)$alkyl, aryl, heteroaryl, aryl$(C_1-C_4)$alkyl, or heteroaryl$(C_1-C_4)$alkyl;
each $R_b$ is independently hydrogen, $(C_1-C_4)$alkyl, aryl, heteroaryl, aryl$(C_1-C_4)$alkyl, or heteroaryl$(C_1-C_4)$alkyl;
each $R_c$ and $R_d$ is independently hydrogen, $(C_1-C_4)$alkyl, aryl, heteroaryl, aryl$(C_1-C_4)$alkyl, or heteroaryl $(C_1-C_4)$alkyl; or, independently, each $NR_cR_d$ together is piperidino, pyrrolidino, or morpholino;
each $R_e$ and $R_f$ is independently hydrogen, $(C_1-C_4)$alkyl, $(C_1-C_4)$alkanoyl, $(C_1-C_4)$alkoxycarbonyl, aryl, heteroaryl, aryl$(C_1-C_4)$alkyl, heteroaryl$(C_1-C_4)$alkyl, aryl$(C_1-C_4)$alkanoyl, or heteroaryl$(C_1-C_4)$alkanoyl; or, independently, each $NR_eR_f$ together is piperidino, pyrrolidino, or morpholino;
each $R_g$ is independently hydrogen, $(C_1-C_4)$alkyl, aryl, heteroaryl, aryl$(C_1-C_4)$alkyl, or heteroaryl$(C_1-C_4)$alkyl; and
L is an unbranched $(C_2-C_{12})$alkylene chain, optionally substituted with one, two, or three substituents selected from the group consisting of $(C_1-C_4)$alkyl, $(C_1-C_4)$alkoxy, hydroxy, oxo, and halo; or L is an unbranched $(C_2-C_{10})$alkylene chain comprising within the chain, at least one divalent radical selected from the group consisting of non peroxide oxy (—O—), thio (—S—), sulfinyl, sulfonyl, —OC(=O)—, and —N($R_m$)HC(=O)—; or L is $R_i$—$(C_2-C_{10})$—$R_k$ wherein $R_i$ and $R_k$ are each independently —N($R_m$)—, —O—, or —S—; each $R_m$ is hydrogen or $(C_1-C_4)$alkyl; and wherein L is attached to X and $X^1$ at any chemically viable position;
or a pharmaceutically acceptable salt thereof.

In certain embodiments, the compounds of the present invention are represented by formulas I and II and the attendant definitions, wherein X is hydrogen; and L is absent.

Compounds of formula (I) and (II) bind to the cocaine recognition site with an affinity comparable to that of cocaine; additionally, the compounds act as potent inhibitors of dopamine uptake. In addition, certain compounds of formula (II) exhibit only weak cocaine- and amphetamine-like effects. Thus compounds of formula (I) and (II) partially mimic cocaine's discriminative stimulus effects. There is evidence that the compounds are also non-addictive and have weak motor stimulant effects.

Based on the ability to bind cocaine recognition sites, the invention also provides a compound of formula I; or a pharmaceutically acceptable salt thereof, as an imaging agent. For example, the invention provides a radiolabeled compound comprising a radionuclide and a compound of formula I; or a pharmaceutically acceptable salt thereof, as well as methods for using such a radiolabeled compound as an imaging agent (e.g. to identify, or evaluate the function of, neurotransmitter binding sights in the brain of a mammal, such as a human).

The invention also provides a method comprising binding a compound of formula I to a mammalian tissue, which comprises dopamine receptors, in vivo or in vitro, by contacting said tissue with an amount of a compound of formula I effective to bind to said receptors. Tissue comprising dopamine receptors with compounds of formula I bound thereto can be used as a pharmacologic tool to identify potential therapeutic agents for the treatment of diseases or conditions associated with dopamine function, by contacting the agents with the tissue, and measuring the extent of displacement of the compound of formula I and/or binding of the agent. Tissue comprising dopamine receptors with compounds of formula I bound thereto can also be used generally to elucidate the physiological function of neurotransmitters.

The invention further features pharmaceutical compositions comprising an effective amount of a compound of formula I as described herein; or a pharmaceutically acceptable salt thereof; in combination with a pharmaceutically acceptable diluent or carrier.

Based on the ability of the compounds to bind to and prevent reuptake from both dopamine and serotonin receptors, the invention further features therapeutic methods, comprising administering a therapeutically effective amount of the claimed pharmaceutical compositions to a subject to treat or prevent a disease or condition that involves modulated or defective dopamine or serotonin transmission, including neurodegenerative diseases (including Parkinson's disease and Alzheimer's disease), depression, bipolar disorders, attention deficit disorder (ADD), and substance (e.g. cocaine) addiction.

Other features and advantages of the invention are set forth in the following detailed description and claims.

DETAILED DESCRIPTION OF THE INVENTION

General

Figure 18:
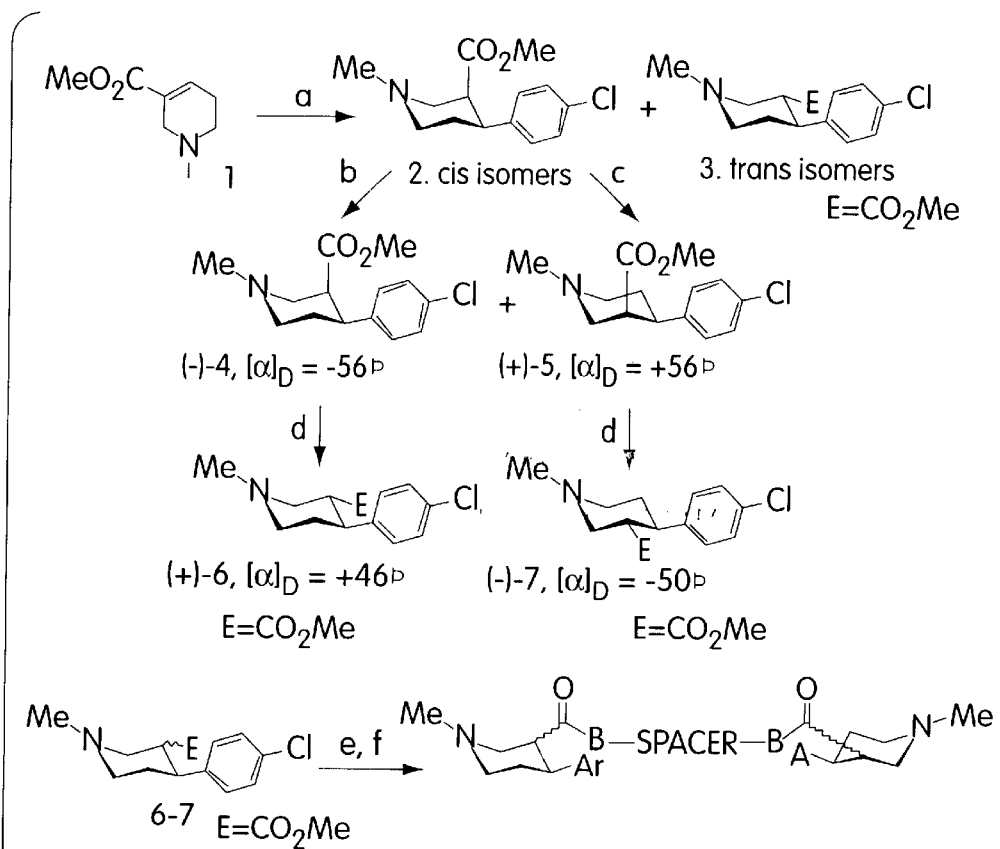
FIG. 18 Illustrates certain synthetic schemes of the present invention.

The instant invention features bivalent compounds that bind to and prevent reuptake from dopamine and serotonin receptors. FIG. 18 delineates the chemistry developed to generate the compounds of the invention. Briefly, the reaction of arecoline as its free base with commercially available 4-chlorophenylmagnesium bromide results in a mixture of cis and trans disubstituted piperidines that are separated by flash chromatography on silica gel. The individual enantiomers of the cis piperidine 4–5 are prepared by cocrystallization of piperidine 2 with (+)- or (−)-dibenzoyltartaric acid to provide pure enantiomers 4 and 5, respectively. The absolute stereochemistry of the (−)-enantiomer 4 as its dibenzoyltartaric acid salt was determined using crystallographic methods. The optically pure (−)-cis- and (+)-cis- enantiomers were converted to their respective trans isomers 6 and 7 using a catalytic amount of NaOMe in MeOH. The esters were hydrolyzed and converted to their respective acid chlorides in two steps, and then reacted without purification with the desired bis-nucleophile to afford the bivalent uptake inhibitors.

Figure 19:
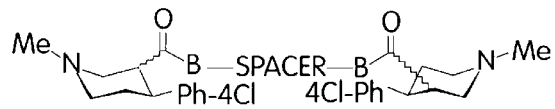
FIG. 19 Illustrates the biological activity of certain compounds of the present invention in assays measuring inhibition of the uptake of DA, NE, and 5-HT.
Figure 20:
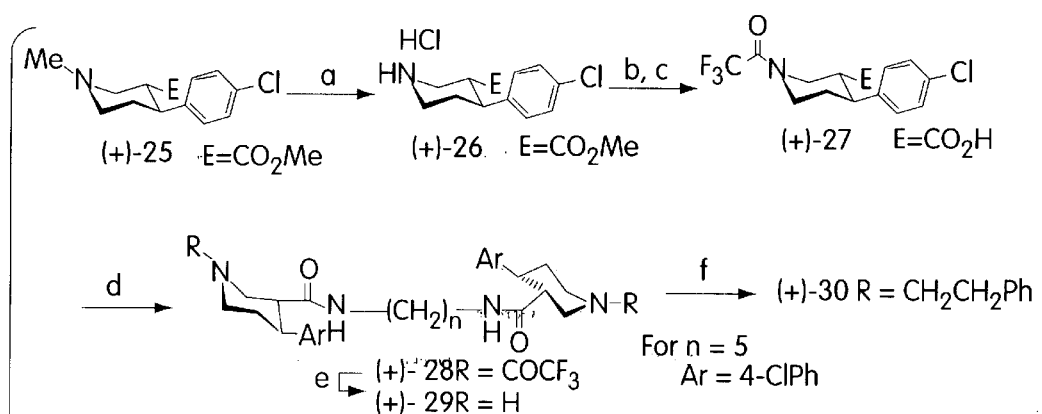
FIG. 20 Illustrates the synthesis of dimeric compound 30.

Selected compounds were tested for their ability to inhibit high affinity uptake of dopaminer (DA), serotonin (5-HT) and norepinephrine (NE) using synaptosomes prepared from striatal midbrain and cortical nerve endings, respectively. The uptake data expressed as Ki's and the selectivity profile (ratio of Ki values) for these compounds are provided in FIG. 19.

The following definitions are used, unless otherwise described: halo is fluoro, chloro, bromo, or iodo. Alkyl, alkoxy, alkenyl, alkynyl, etc. denote both straight and branched groups; but reference to an individual radical such as "propyl" embraces only the straight chain radical, a branched chain isomer such as "isopropyl" being specifically referred to. Aryl denotes a phenyl radical or an ortho-fused bicyclic carbocyclic radical having about nine to ten ring atoms in which at least one ring is aromatic. Heteroaryl encompasses a radical attached via a ring carbon of a monocyclic aromatic ring containing five or six ring atoms consisting of carbon and one to four heteroatoms each selected from the group consisting of non-peroxide oxygen, sulfur, and N(Z) wherein Z is absent or is H, O, ($C_1$–$C_4$) alkyl, phenyl or benzyl, as well as a radical of an ortho-fused bicyclic heterocycle of about eight to ten ring atoms derived therefrom, particularly a benz-derivative or one derived by fusing a propylene, trimethylene, or tetramethylene diradical thereto.

It will be appreciated by those skilled in the art that compounds of the invention having a chiral center may exist in and be isolated in optically active and racemic forms. Some compounds may exhibit polymorphism. It is to be understood that the present invention encompasses any racemic, optically active, polymorphic, or stereoisomeric form, or mixtures thereof, of a compound of the invention, which possess the useful properties described herein, it being well known in the art how to prepare optically active forms (for example, by resolution of the racemic form by recrystallization techniques, by synthesis, from optically active starting materials, by chiral synthesis, or by chromatographic separation using a chiral stationary phase) and how to determine the relevant pharmacological properties of the compound using the standard tests described herein, or using other similar tests which are well known in the art.

Specific values listed below for radicals, substituents, and ranges, are for illustration only and they do not exclude other defined values or other values within defined ranges for the radicals and substituents A specific value for $R^3$ is phenyl, 4-fluorophenyl, 4-methylphenyl, 4-isopropenylphenyl, 4-vinylphenyl, 4-ethyl-3-iodophenyl, 4-ethylphenyl, 4-bromophenyl, 4-(1-naphthyl)phenyl, 4-(2-naphthyl)phenyl, 4-(2-thienyl)phenyl, 4-allylphenyl, 4-trifluoromethylphenyl, or 4-(2-chlorovinyl)phenyl.

Specifically $R^6$ is hydrogen, methyl, ethyl, phenyl($C_1$–$C_4$) alkyl, benzyl, 3-phenylpropyl, or trifluoromethyl.

Specifically $R^1$ and $R^3$ are in a trans configuration.

Although specific linkers L are disclosed and claimed herein, the specific structure of L is not critical, provided L does not interfere with the biological activity of the compounds of formula I. Specifically, L can be any divalent group that separates X and $X^1$ by about 4 to about 25 Å. Preferably L separates X and $X^1$ by about 5 to about 12 Å. One skilled in the art can readily identify such groups L using known chemical bond lengths and angles, or using computer based chemical modeling programs which are well known in the art.

Processes and intermediates useful for preparing compounds of formula I are provided as further embodiments of the invention and are illustrated by the following procedures.

Figure 1:
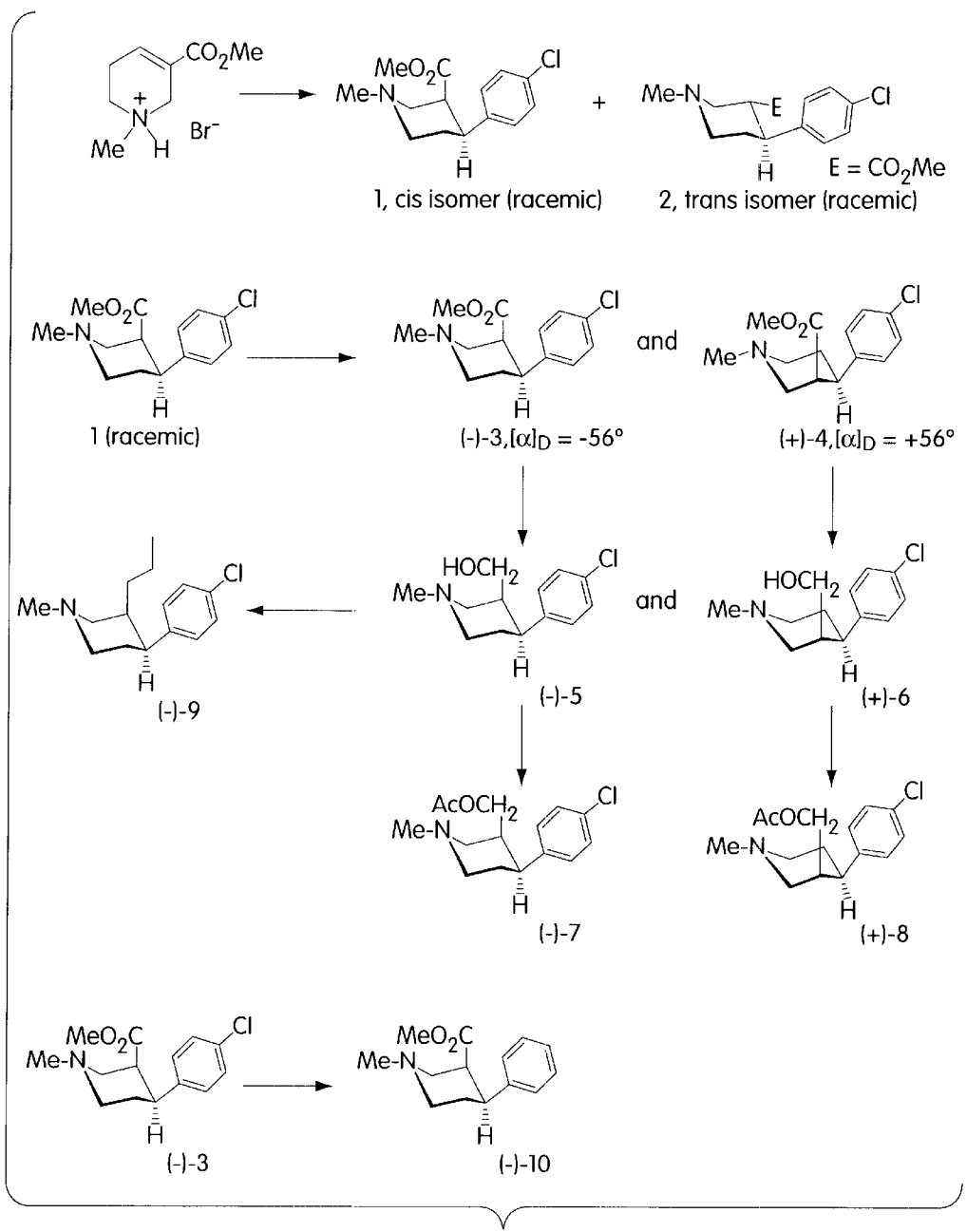
FIGS. 1–16 Illustrate the synthesis of compounds of formula II that can be used to prepare compounds of formula I.

As illustrated in FIG. 1, racemic piperidines 1 and 2 were prepared starting from arecoline hydrobromide using chemistry similar to that reported by Plati for the synthesis of the unsubstituted phenyl bearing piperidine analogs (Plati, J. T.;

Ingberman, A. K.; Wenner, W. Pyrilindene Derivatives. III. Synthesis from Arecoline. *J. Org. Chem.* 1957, 22, 261–265).

Thus, the hydrobromide salt of arecoline was converted to its free base by sodium bicarbonate, and this intermediate subjected to a Grignard reaction using p-chlorophenylmagnesium bromide. A mixture of the cis- and trans-disubstituted piperidines 1 and 2 was produced in a 75/25 ratio. The cis derivative was obtained by crystallization of the crude material using EtOAc/hexane as solvent. The racemic trans piperidine was readily obtained by flash chromatography of the mother liquor.

The cis ester was resolved by use of (+)- and (−)- dibenzoyltartaric acid to provide the pure enantiomers (−)-3 and (+)-4 (Law, H.; Leclerc, G. A.; Neumeyer, J. L. An efficient and inexpensive resolution of the potent dopaminergic substance 3-(3-Hydroxyphenyl)-N-(1-propyl)- piperidine (±)-3-PPP. *Tetrahedron Asymm.* 1991, 2, 989–992). An X-ray structure determination of the salt formed from (−)-dibenzoyltartaric acid and 1 was used to determine the absolute stereochemistry of (−)-3 which is depicted in FIG. 1. As is apparent, the absolute stereochemistry of the (−)-isomer corresponds to that found in the WIN series of structures.

The optically pure (+)- and (−)-cis esters were converted to their respective alcohols (−)-5 and (+)-6 by lithium aluminum hydride reduction, and these alcohols were acylated with acetic anhydride in the presence of pyridine to give acetate derivatives (−)-7 and (+)-8. Compound 9, wherein $R^1$ is propyl, was prepared from alcohol 5 by oxidation to the aldehyde followed by Wittig reaction and catalytic hydrogenation. Compound 10 was prepared from the cis piperidine (−)-3 by hydrogenolysis over 10% palladium on charcoal in methanol at atmospheric pressure.

Figure 2:
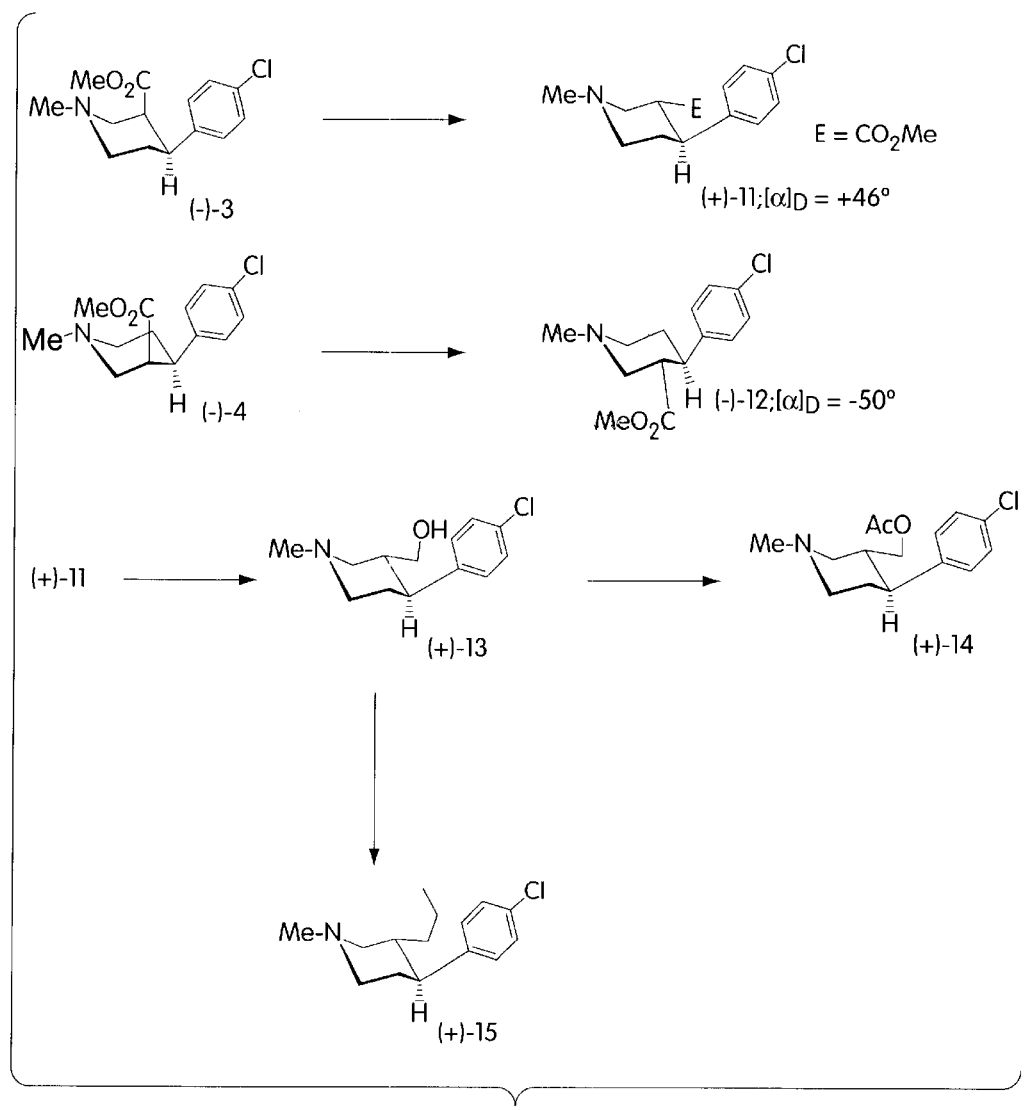

Because it was difficult to obtain satisfactory crystals from (±)-2 and dibenzoyltartaric acid, compounds (+)-11 and (−)-12 were prepared by the base-catalyzed epimerization of compounds (−)-3 and (−)-4 as shown in FIG. 2. The more active isomer (+)-11 was converted to the corresponding alcohol (+)-13 by reduction with lithium aluminum hydride in tetrahydrofuran. Acylation of alcohol (+)-13 with acetic anhydride and pyridine gave the acetate (+)-14. The n-propyl derivative (+)-15 was prepared by oxidation of alcohol (+)-13 followed by Grignard reaction using ethyltriphenyl-phosphonium bromide, and subsequent hydrogenation over 5% platinum on carbon.

Figure 3:
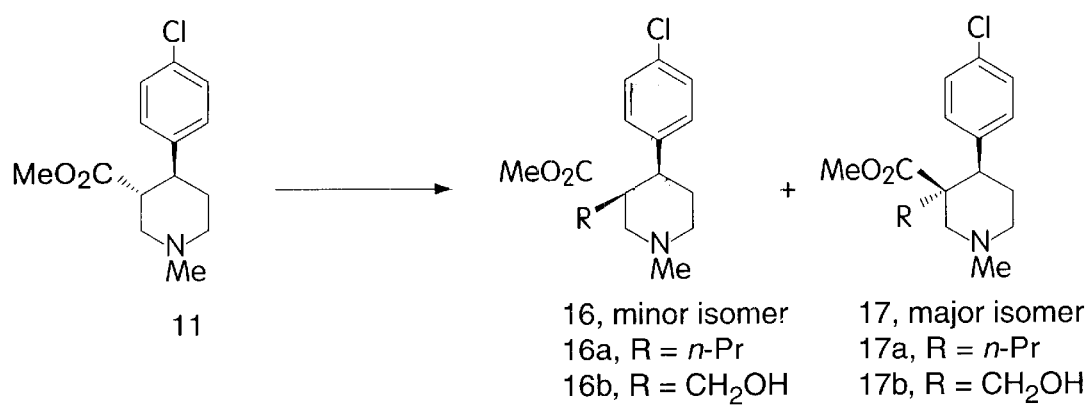

As illustrated in FIG. 3, a compound of formula II wherein is $R^2$ ($C_1$–$C_6$)alkyl and $R^1$ is —C(=O)OR$_a$ or cyano can be prepared from a corresponding compound of formula II wherein $R^2$ is hydrogen by deprotonation followed by alkylation.

Figure 4:
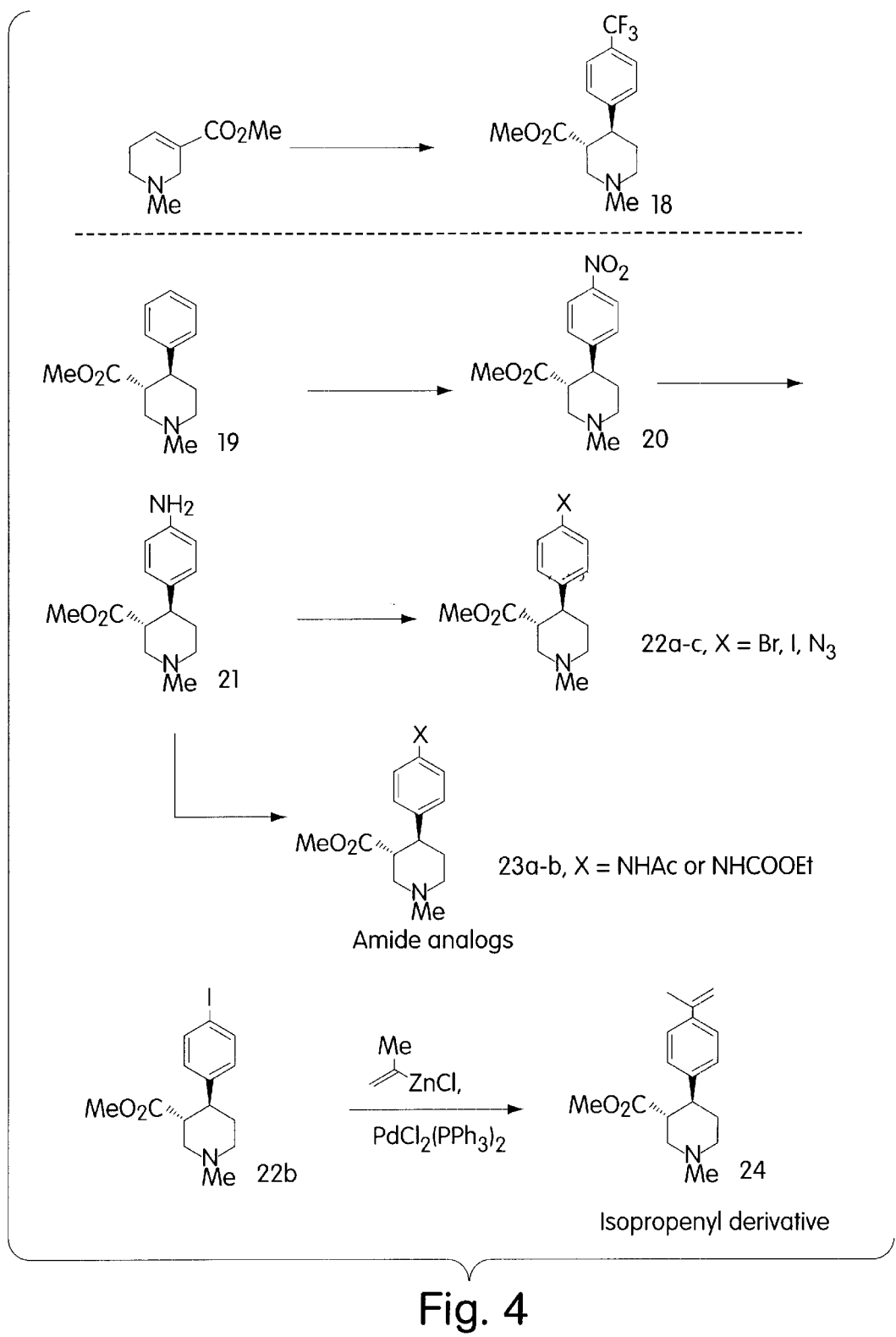
Figure 5:
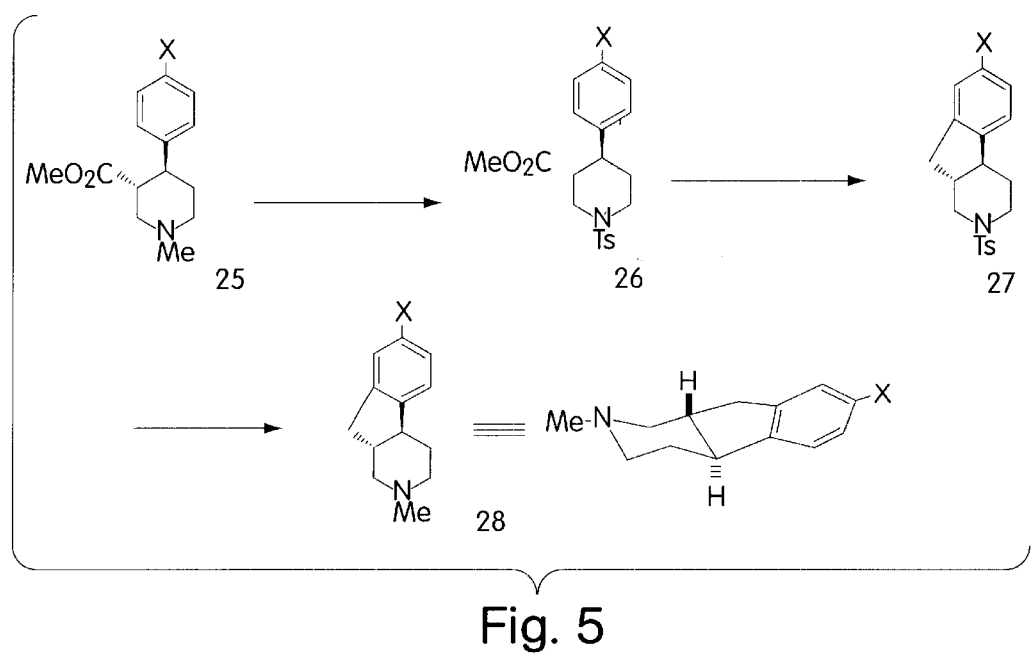

As illustrated in FIG. 4, compounds of formula II wherein $R_3$ is substituted phenyl can be prepared using procedures similar to those described in: Carroll, F. I., Gao, Y., Rahman, M. A., Abraham, P., Parham, K., Lewin, A. H., Boja, J. W., and Kuhar, M. J. (1991) Synthesis, ligand binding, QSAR and CoMFA study of 3b-(p-substituted phenyl)tropane-2β- carboxylic acid methyl esters. *J. Med. Chem.*, 34, 2719–2725; or Blough, B. E., Abraham, P., Lewin, A. H., Kuhar, M. J., Boja, J. W., and Carroll, F. I. (1996) Synthesis and transporter binding properties of 3β-(4'alkyl-, 4'-alkenyl-, and 4'-alkynylphenyl)nortropane-2β-carboxylic acid methyl esters: serotonin transporter selective analogs. *J. Med. Chem.*, 39, 4027–4035. Treatment of arecoline with 4-trifluoromethylphenyl magnesium bromide in ether followed by chromatographic separation of the resulting isomers gives compound 18. Nitration of compound 19 with nitronium tetrafluoroborate gives nitro compound 20, which can be reduced with Rany Ni to give amine 21. Treatment of amine 21 with HONO followed by copper(I) bromide, potassium iodide or sodium azide gives compounds 22a–c. Treatment of amine 21 with acetyl chloride or ethyl chloroformate gives amide 23a or carbamate 23b. Additionally, aryl iodide 22b can be treated with isopropenyl zinc chloride in the presence of a palladium catalyst bis (triphenylphosphine)palladium(II) chloride to yield isoprenyl compound 24. The invention also provides Compounds of formula II wherein $R^3$ is azidophenyl, which are useful intermediates for preparing other compounds of formula II As shown in FIG. 5, compounds of formula II wherein $R^1$ is —$CH_2$—, or —$CH_2CH_2$—, wherein $R^1$ is also attached to a carbon at the ortho position of $R^3$; and $R^3$ is ($C_6$–$C_{10}$)aryl, or 5–10 membered heteroaryl can be prepared from a corresponding compound wherein $R^1$ is —C(=O)OR$_a$. Treatment of methyl amine 25 with 1-chloroethyl chloroformate and methanol, followed by p-toluenesulfonyl chloride in pyridine gives the tosyl amine 26. Reduction of the ester with lithium aluminum hydride followed by treatment with PBr$_3$ and cyclization with AlCl$_3$ gives tricyclic compound 27 which can be deprotected by treatment with HBr/HOAc, and converted to the methyl amine 28 by reatment with sodium hydroxide and formaldehyde, followed by reduction with sodium cyanoborohydride.

Figure 6:
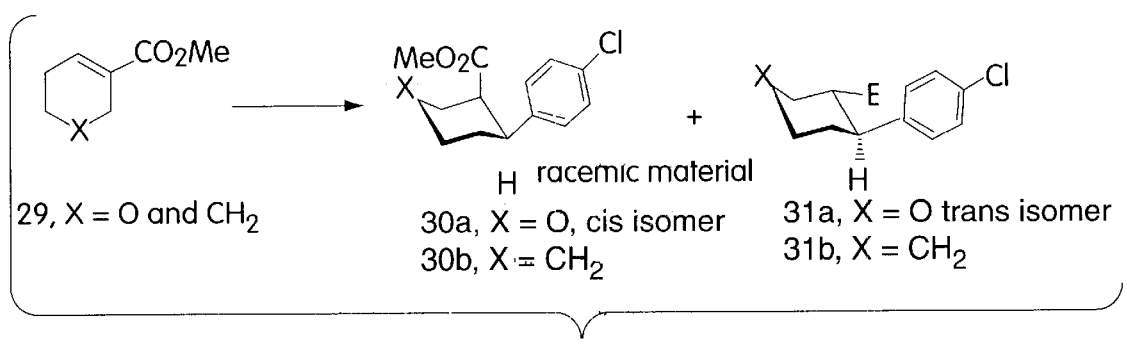

As illustrated in FIG. 6, compounds of formula II wherein Y is —$CH_2$— or —O— may be prepared from the appropriate dihydropyran-3-carboxylate or cyclohexenecarboxylate using procedures similar to those described above for the preparation of the corresponding compounds wherein Y is NR$^6$.

Figure 7:
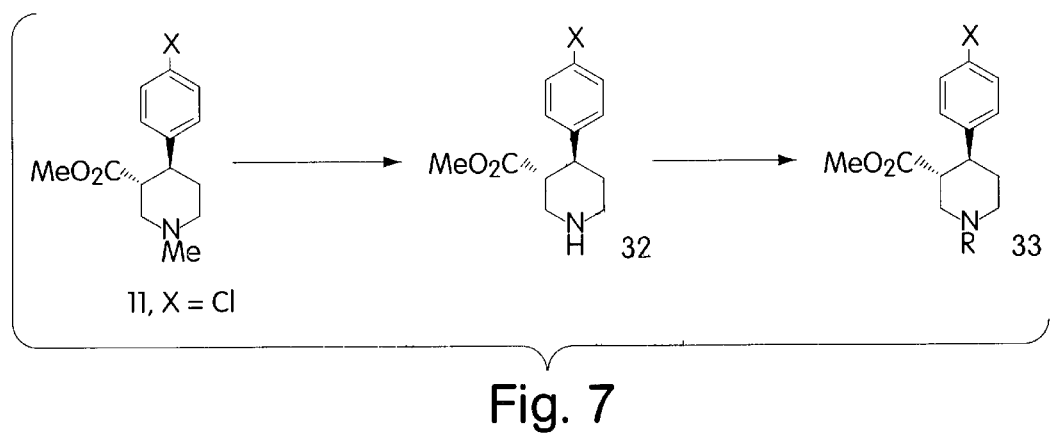

As illustrated in FIG. 7, a compound of formula II wherein $R^6$ is ($C_1$–$C_6$)alkyl or ($C_1$–$C_6$)alkanoyl (33) can be prepared from a corresponding compound of formula II wherein $R^6$ is methyl by treatment with ACECl in refluxing methanol to give amine 32, followed by alkylation or acylation of the amine using standard conditions.

Figure 8:
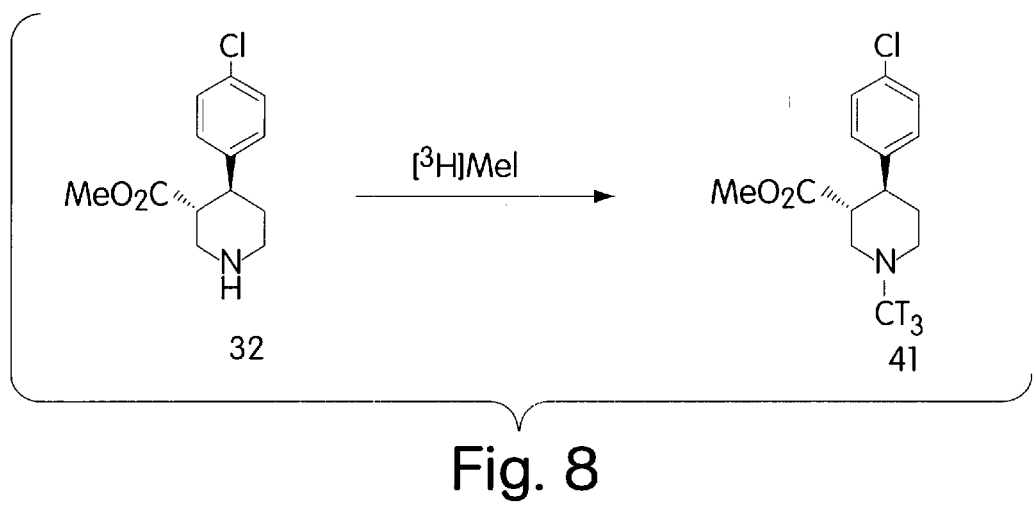

As shown in FIG. 8, a radiolabeled compound of formula II can be prepared by alkylation of an amine of formula 32 with a radiolabeled compound (e.g. IC[$^3$H]).

Figure 9:
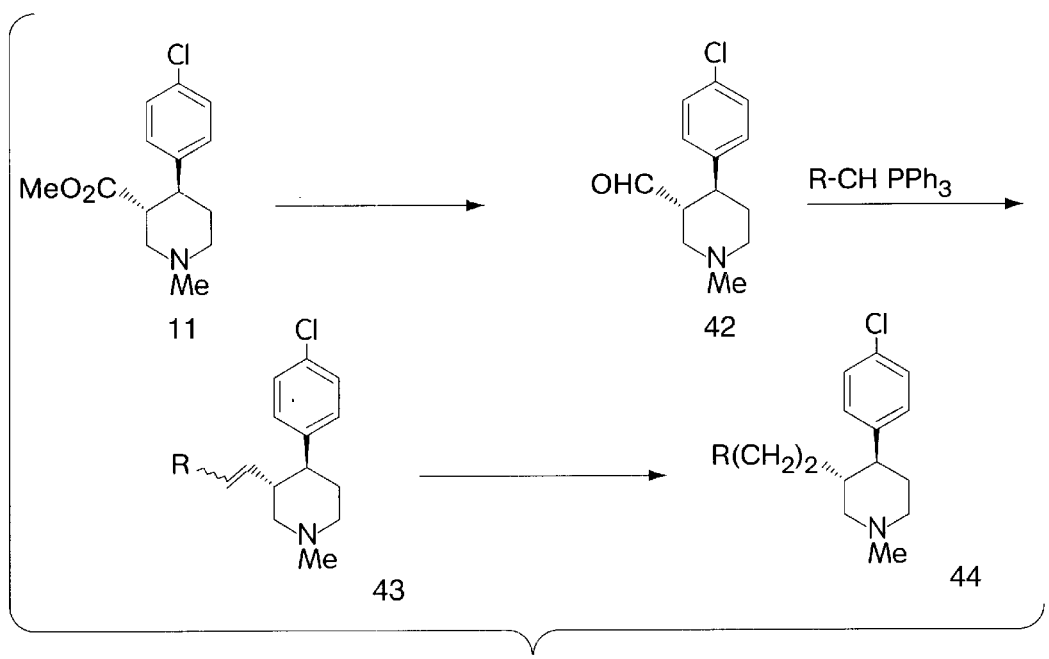

As shown in FIG. 9, compounds of formula II wherein $R^1$ is ($C_1$–$C_6$)alkyl, ($C_2$–$C_6$)alkenyl, or ($C_2$–$C_6$)alkynyl can be prepared using procedures similar to those described in Kozikowski, A. P., Saiah, M. K. E., Johnson, K. M., and Bergmann, J. S. (1995) Chemistry and biology of the 2β-alkyl-3β-phenyl analogues of cocaine: subnanomolar affinity ligands that suggest a new pharmacophore model at the C-2 position. *J. Med. Chem.*, 38, 3086–3093. Reduction of ester 11 with DIBAL followed by oxidation gives aldehyde 42. Treatment of compound 42 with a Grignard reagent gives an alkene of formula 43, which can be reduced with hydrogen over platinum on carbon to give an alkane of formula 44.

Figure 10:
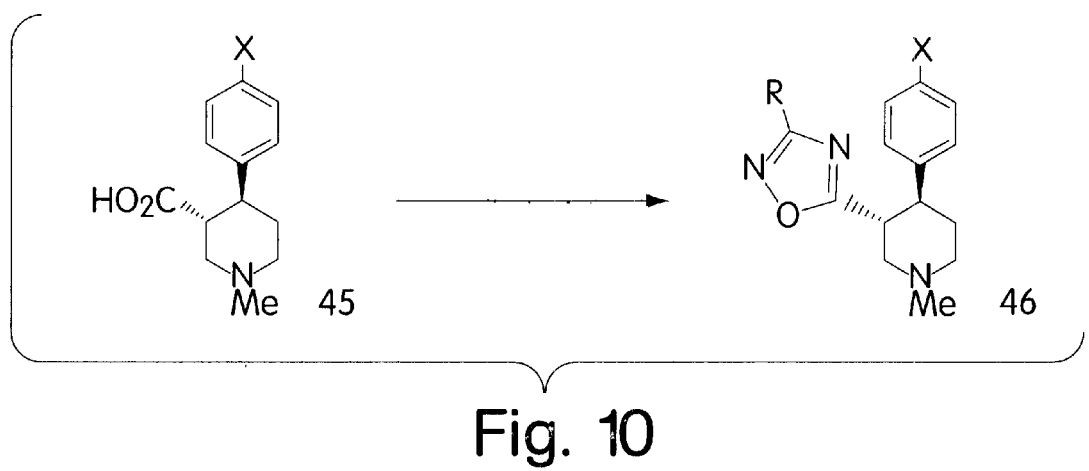
Figure 11:
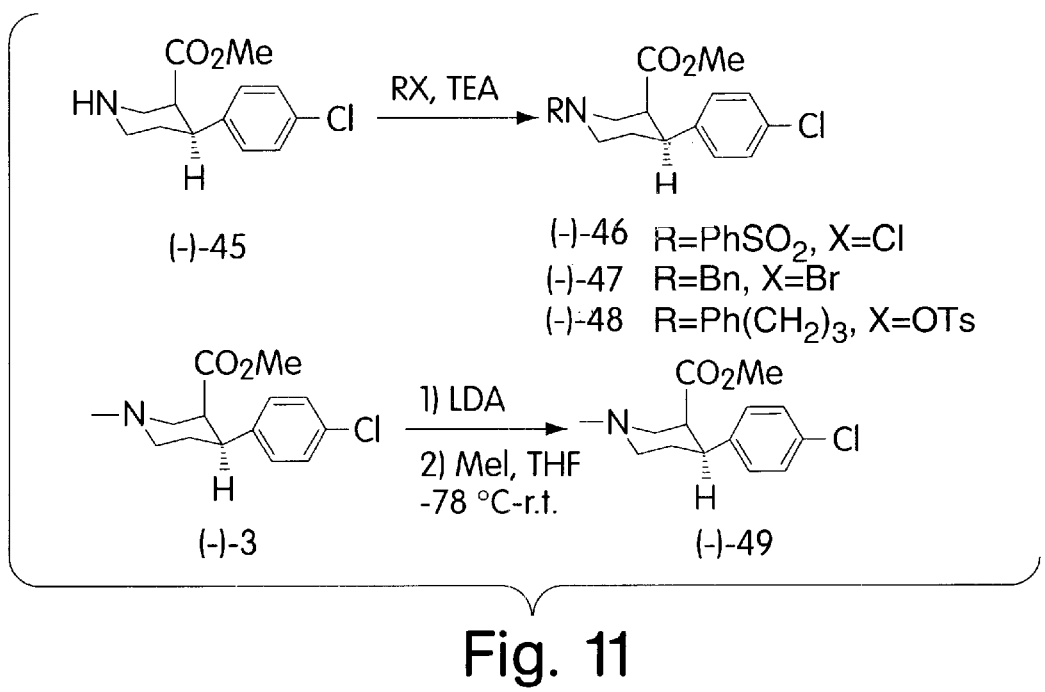
Figure 12:
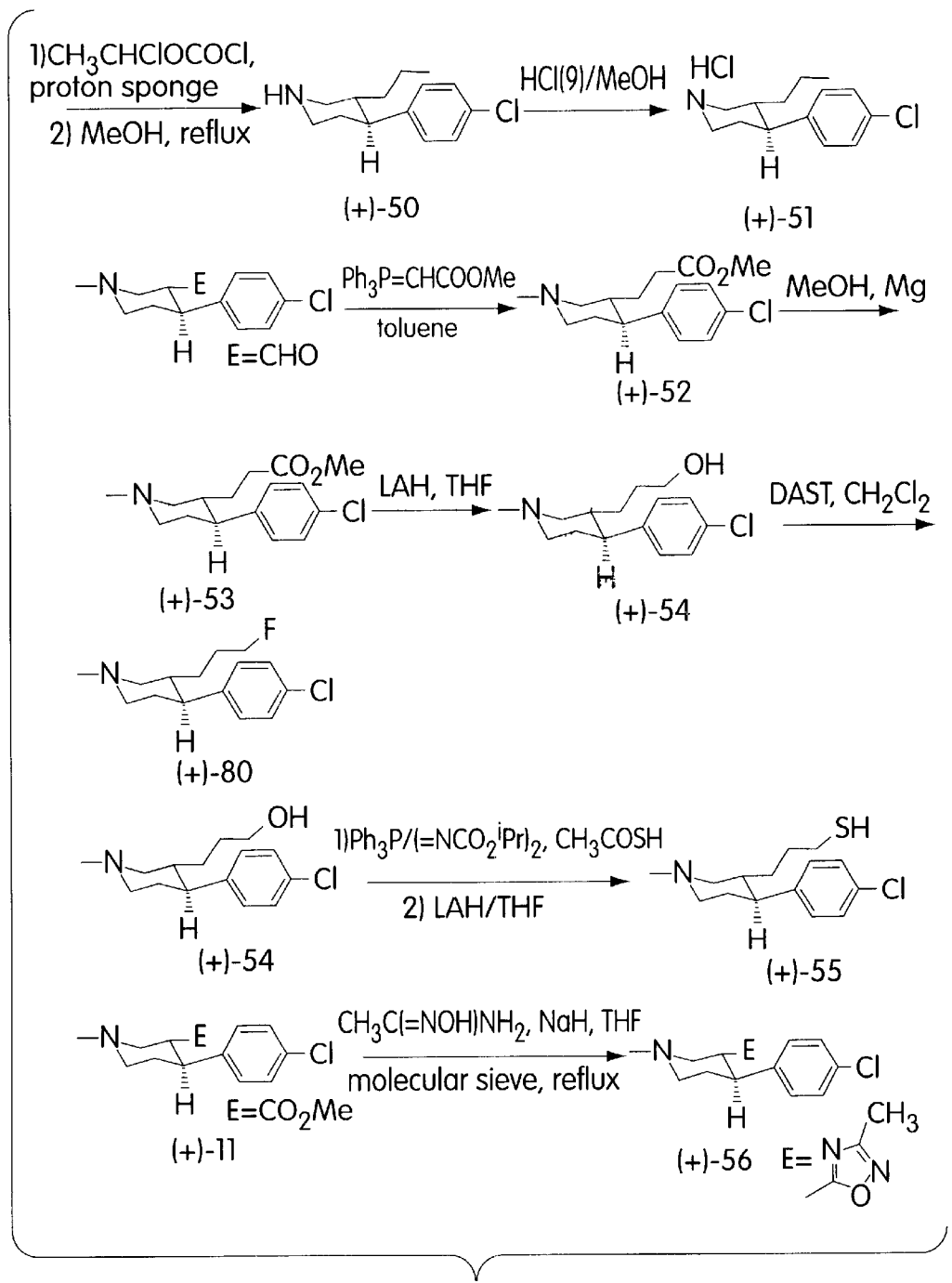
Figure 13:
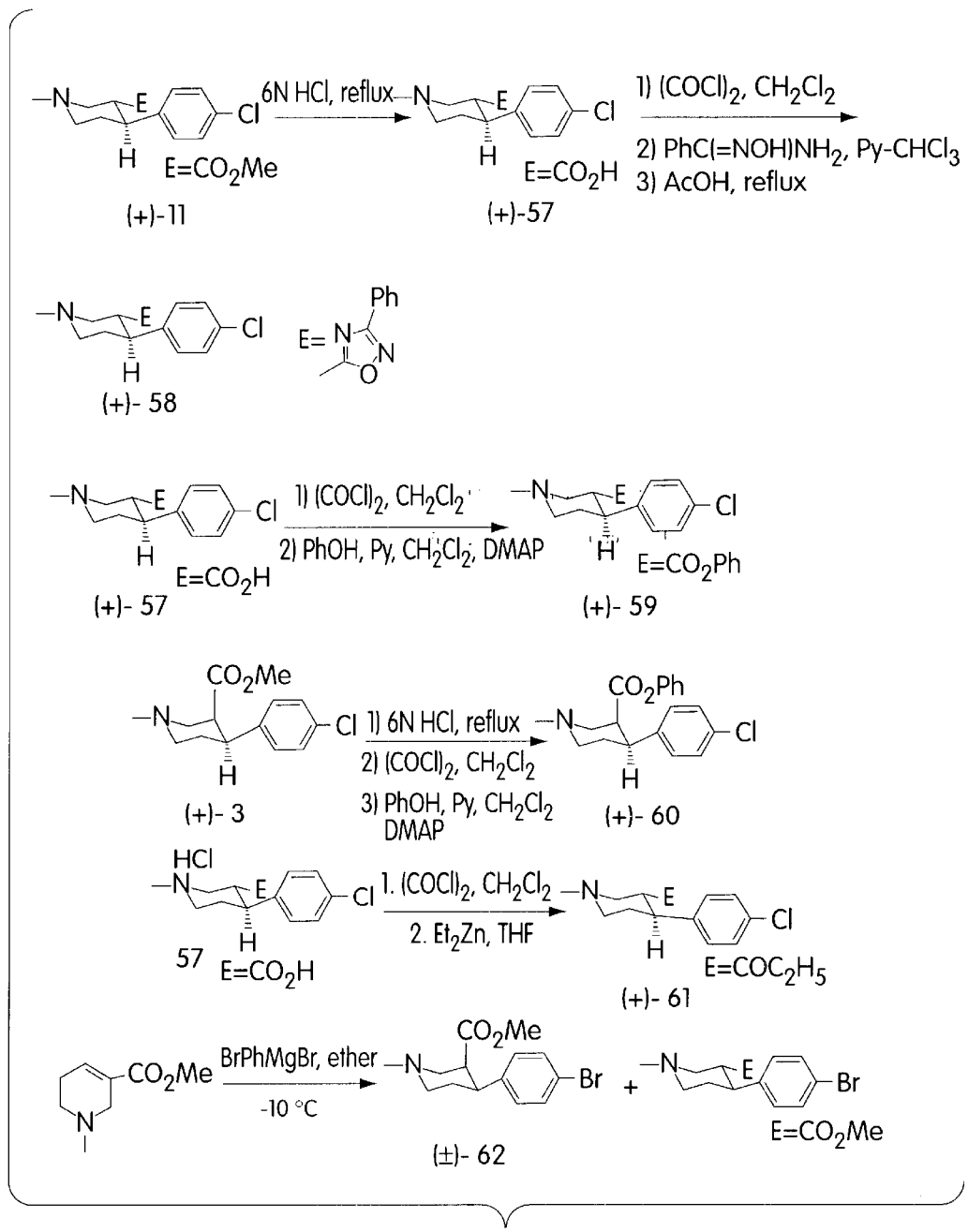
Figure 14:
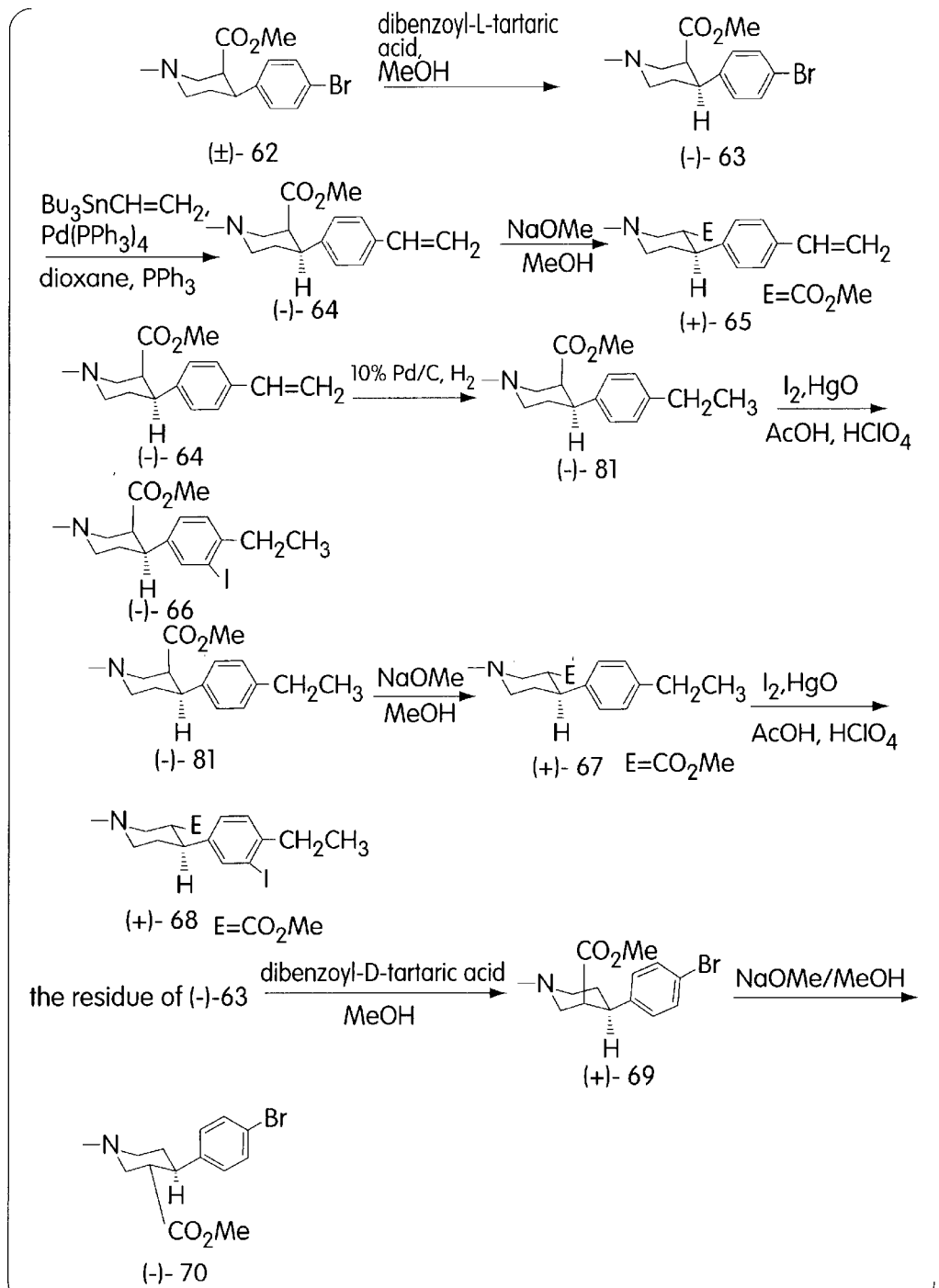
Figure 15:
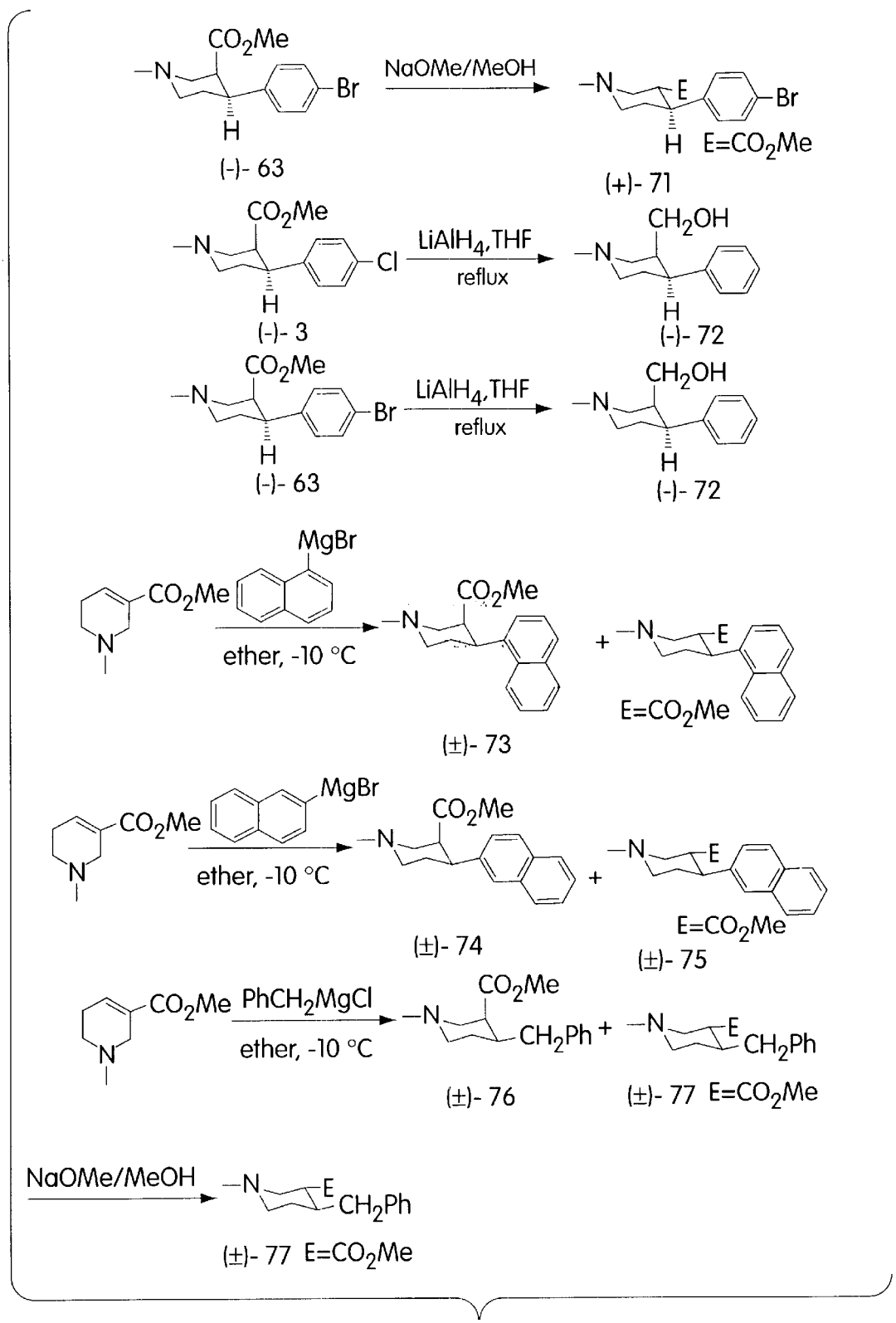
Figure 16:
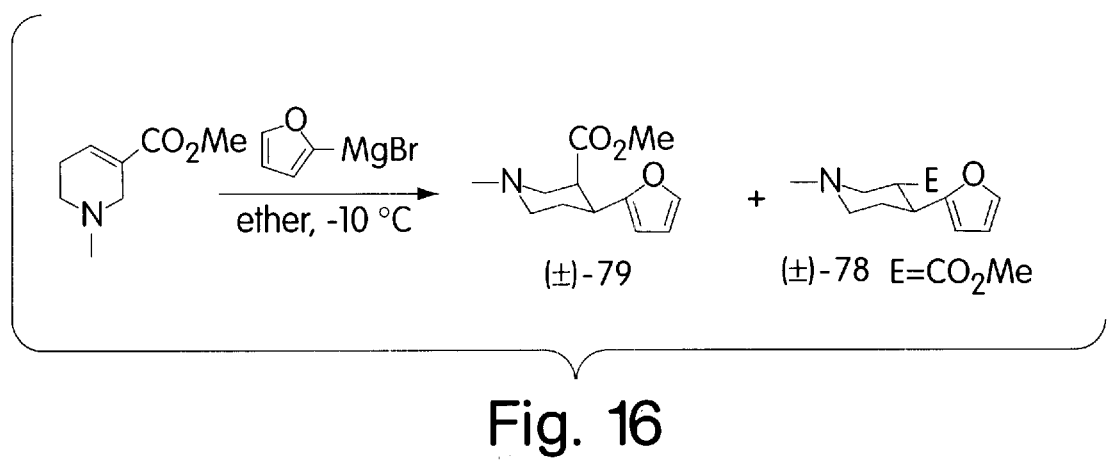

As illustrated in FIG. 10, a compound of formula II wherein $R^1$ is oxadiazolyl can be prepared by conversion of the ester group in a compound of formula II wherein $R^1$ is —C(=O)OR$_a$ to an acid, followed by acid chloride formation, and reaction with the appropriate amide oxime as described in: Kotian, P., Mascarella, S. W., Abraham, P., Lewin, A. H., Boja, J. W., Kuhar, M. J., and Carroll, F. I. (1996) Synthesis, ligand binding, and quantitative structure-activity relationship study of 3β-(4'-substituted phenyl)-2β- heterocyclic tropanes: evidence for an electrostatic interaction at the 2β-position. *J. Med. Chem.*, 39, 2753–2763.

It is noted that many of the starting materials employed in the synthetic methods described above are commercially available or are reported in the scientific literature, and that certain compounds of formula II are useful as intermediates to prepare other compounds of formula II.

Compounds of formula I can be prepared by linking compounds of formula II with a group L using synthetic methods that are well known in the art.

Figure 17:
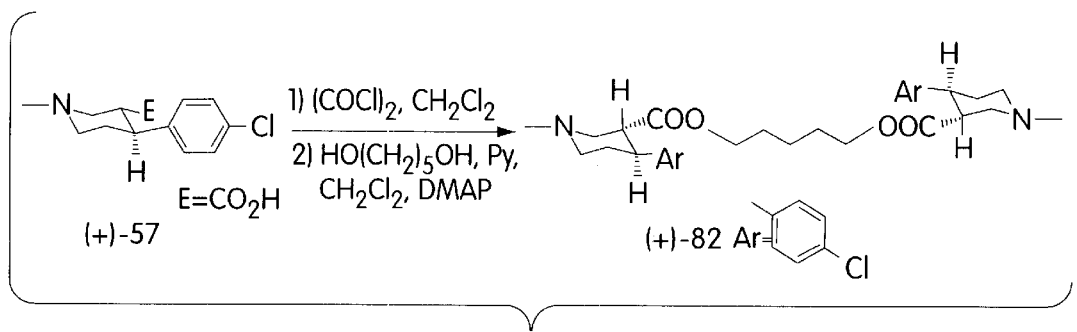
FIG. 17 Illustrates the synthesis of a compound of formula I.

Compounds of formula I wherein X and $X^1$ are linked by L through $R^1$ carboxy groups can conveniently be prepared from compounds of formula II therein $R^1$ is an acid, by conversion to the corresponding acid chloride followed by reaction with a diol of formula HO—L—OH, for example as described in Example 54 and illustrated in FIG. 17.

Compounds of formula I wherein X and $X^1$ are linked by L through piperidino nitrogens can conveniently be prepared from compounds of formula II wherein Y is $NR^6$ and $R^6$ is hydrogen, by alkylation with a compound W—L—W wherein W is a suitable leaving group (e.g. chloro or bromo).

Compounds of formula I wherein X and $X^1$ are linked by L through a carbon of $R^3$ can be prepared using alkylation or acylation methods that are known in the art.

Synthesis of Unsymmetrical Bivalant Ligands

Figure 21:
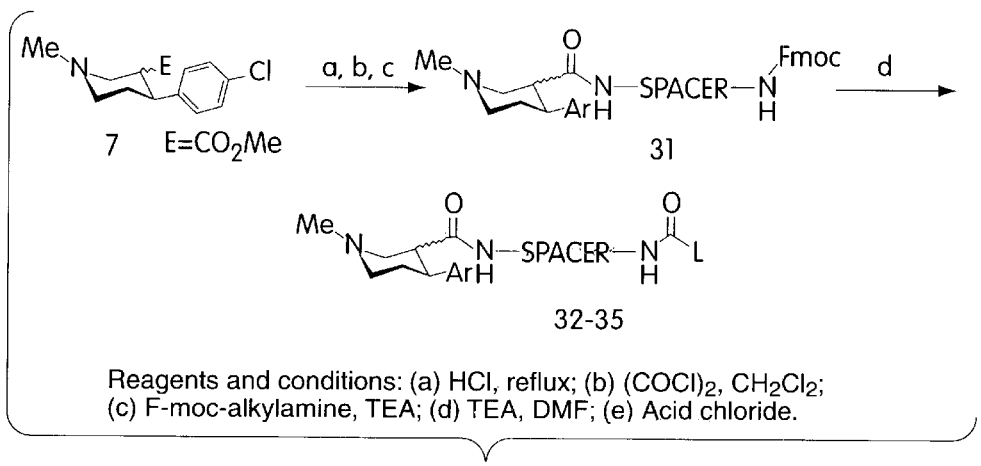
FIG. 21 Illustrates the synthesis of dimeric compounds 32–35.

Our SAR database includes unsymmetrical bivalent ligands. The reaction pathway shown in FIG. 21 was used to prepare a number of unsymmetrical bivalent ligands. The synthesis is short and versatile and is amenable to automated parallel synthesis. Automation will allow rapid development of unsymmetrical series of both cis and trans piperidines.

Synthesis of Ether-linked Bivalant Ligands

Figure 22:
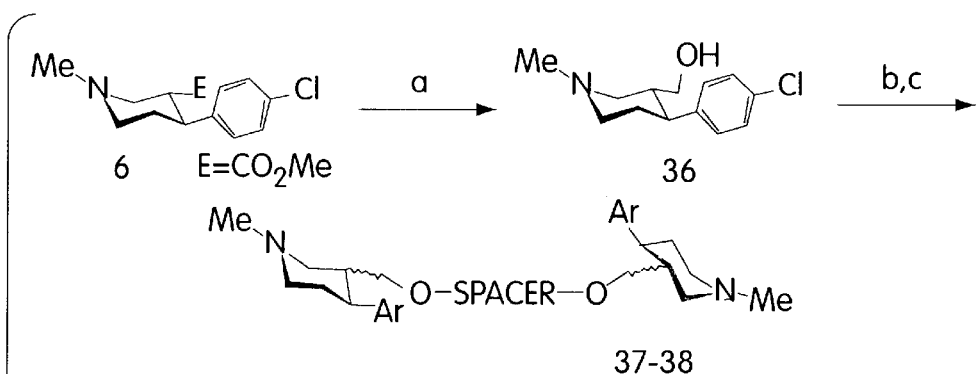
FIG. 22 Illustrates the synthesis of ether-linked dimeric compounds 37 and 38.
Figure 23:
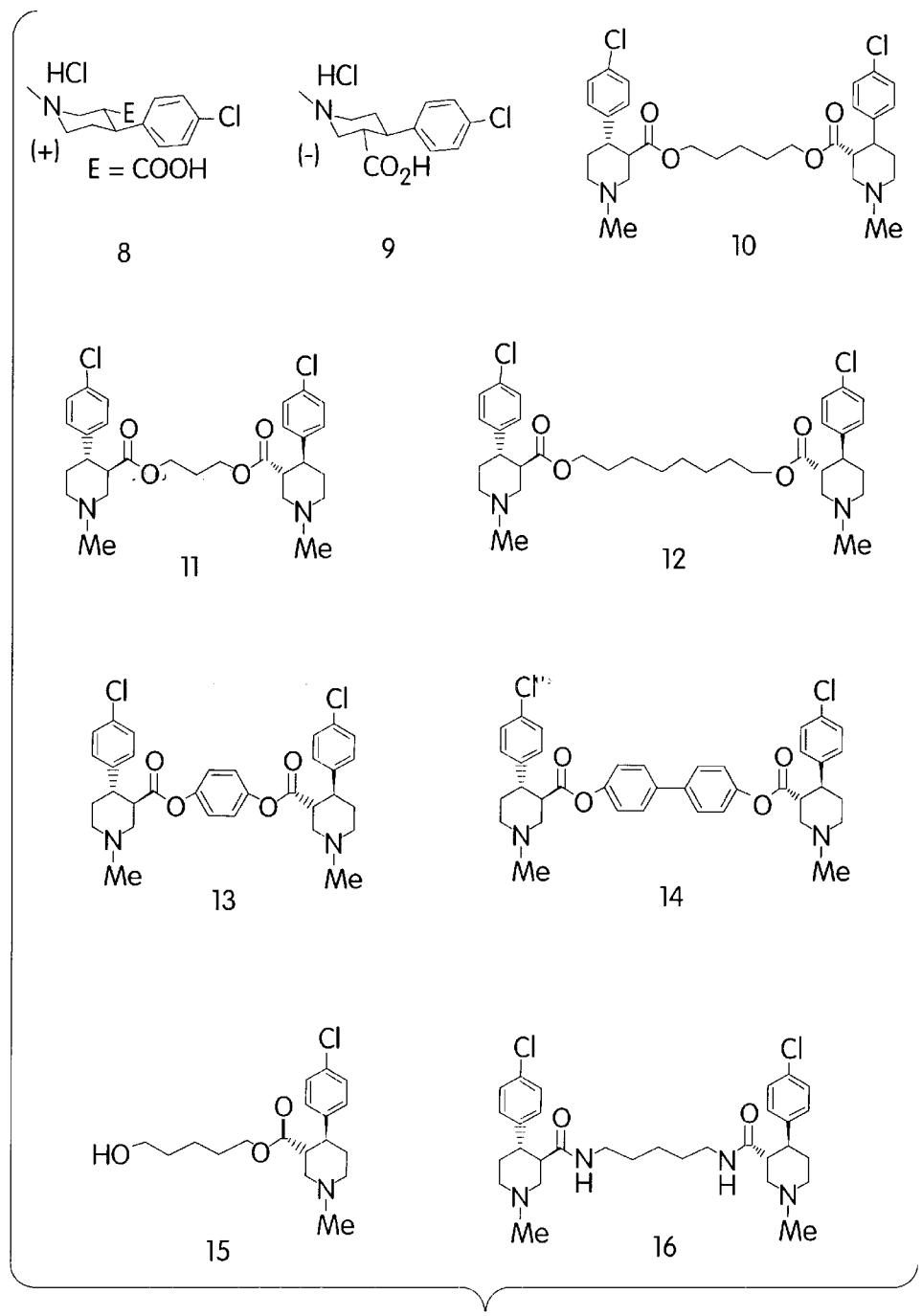
FIG. 23 Illustrates compounds 8–16 of the present invention.
Figure 24:
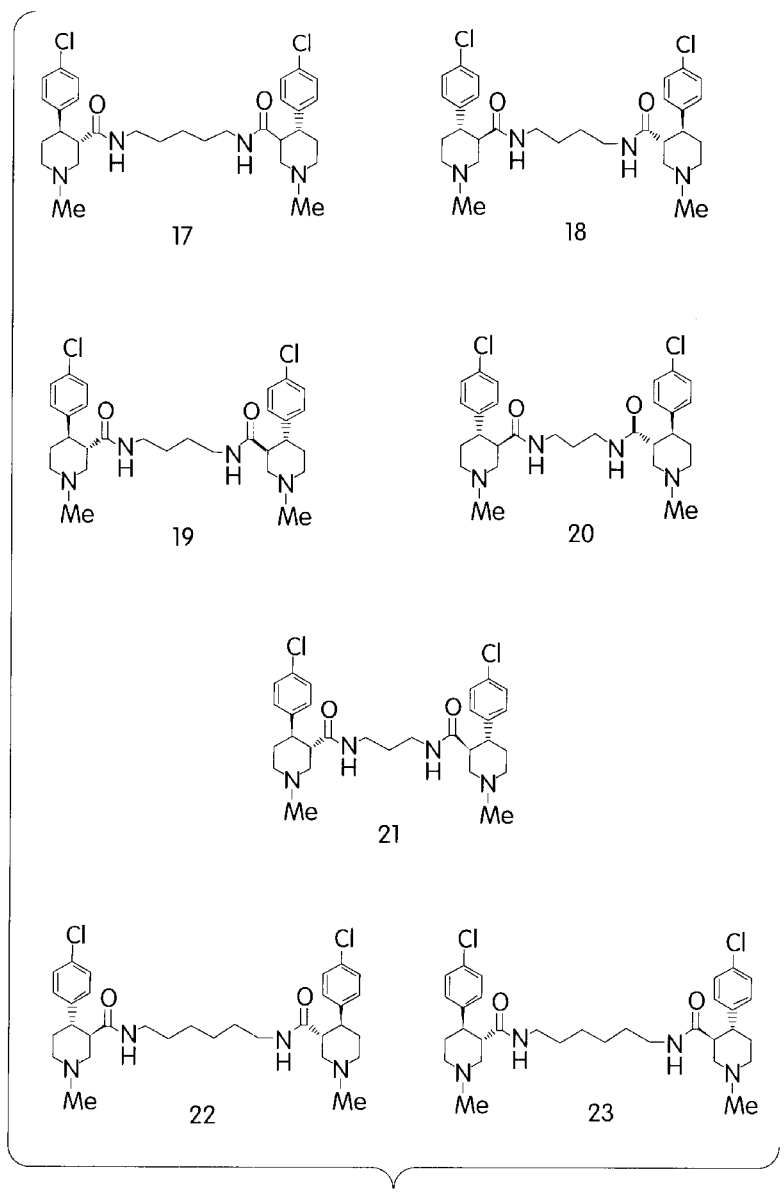
FIG. 24 Illustrates compounds 17–23 of the present invention.
Figure 25:
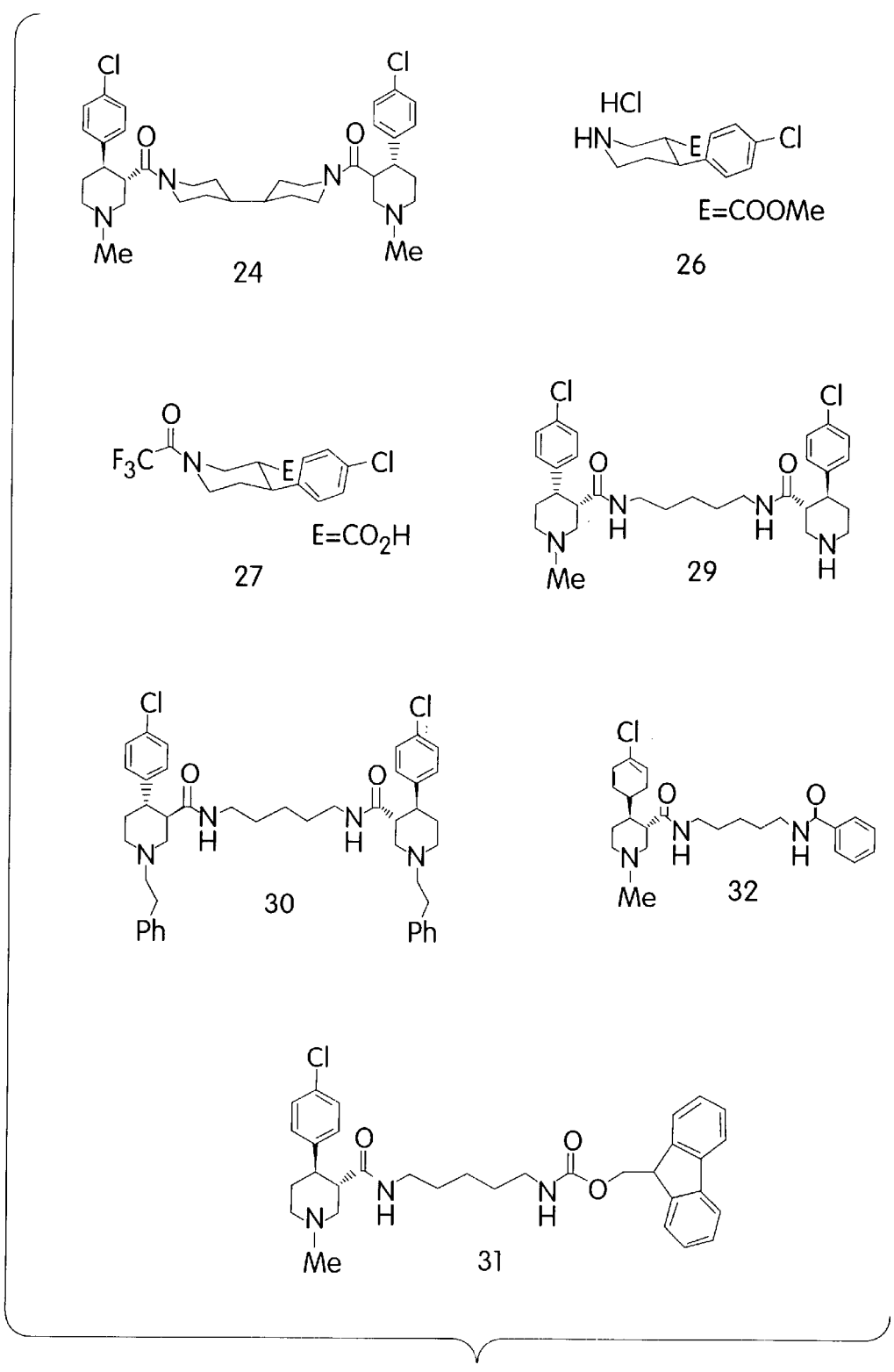
FIG. 25 Illustrates compounds 24, 26, 27, and 29–32 of the present invention.
Figure 26:
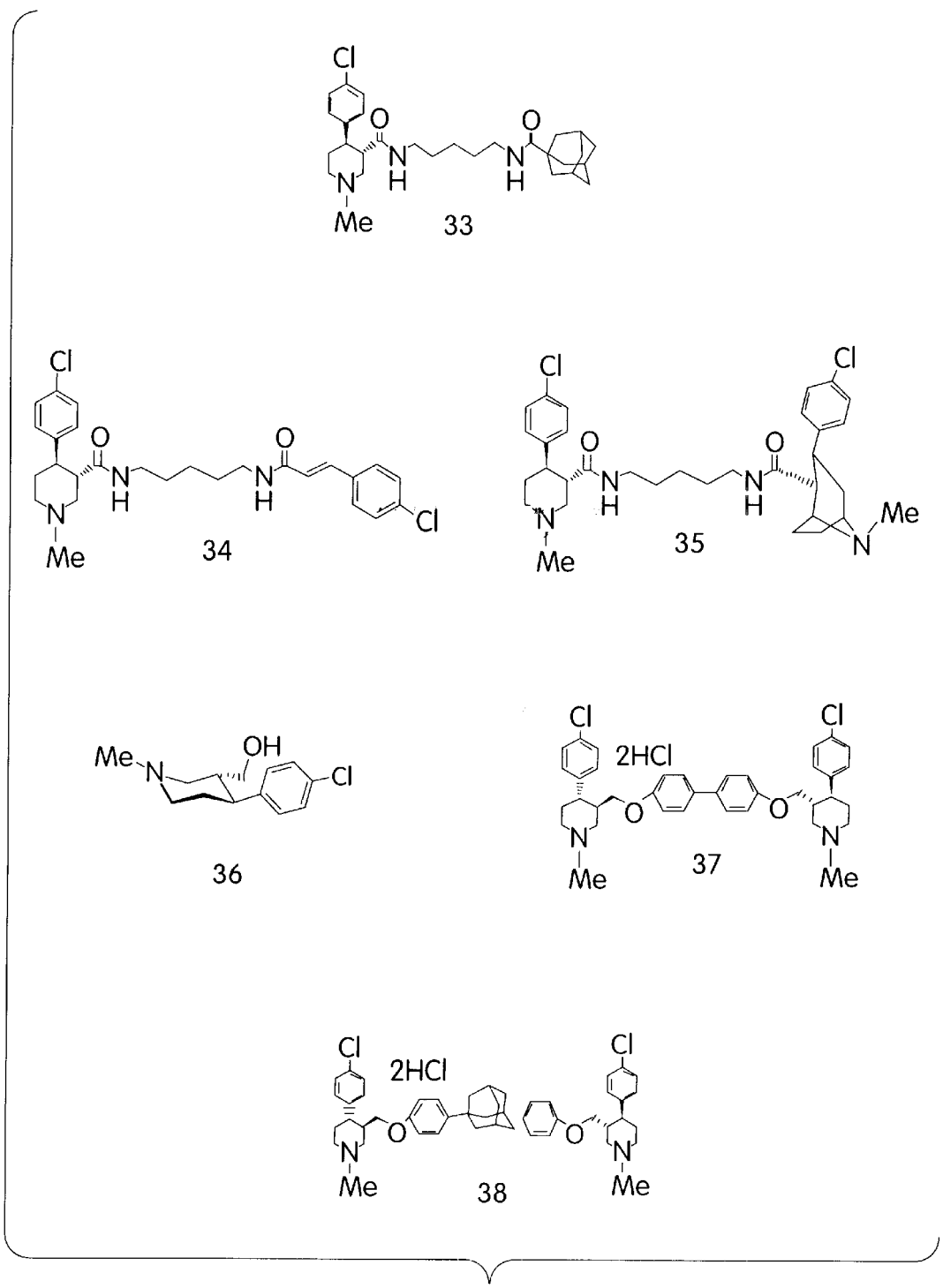
FIG. 26 Illustrates compounds 33–38 of the present invention.

Our SAR database has been expanded by exploring the effect of the substitution of amide groups in the linking chain with ether groups. The reaction pathway shown in FIG. 22 was used to prepare a number of bivalent ligands that mimic SSRIs in their structural connectivity. The synthesis is short and versatile and is amenable to automated parallel synthesis. Again, automation will allow rapid development of unsymmetrical series of both cis and trans ether-linked piperidines.

Formulation

In cases where compounds are sufficiently basic or acidic to form stable nontoxic acid or base salts, administration of the compounds as salts may be appropriate. Examples of pharmaceutically acceptable salts are organic acid addition salts formed with acids which form a physiological acceptable anion, for example, tosylate, methanesulfonate, acetate, citrate, malonate, tartarate, succinate, benzoate, ascorbate, α-ketoglutarate, and α-glycerophosphate. Suitable acid addition salts of inorganic acids may also be formed, including hydrochloride, sulfate, nitrate, bicarbonate, and carbonate salts.

Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

The compounds of formula I can be formulated as pharmaceutical compositions and administered to a mammalian host, such as a human patient in a variety of forms adapted to the chosen route of administration, i.e., orally or parenterally, by intravenous, intramuscular, topical or subcutaneous routes.

Thus, the present compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially nontoxic in the amounts employed. In addition, the active compound may be incorporated into sustained-release preparations and devices.

The active compound may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form must be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compounds may be applied in pure form, i.e., when they are liquids. However, it will generally be desirable to administer them to the skin as compositions or formulations, in combination with a dermatologically acceptable carrier, which may be a solid or a liquid.

Useful dosages of the compounds of formula I can be determined by comparing their in vitro activity, and in vivo activity in animal models. Methods for the extrapolation of effective dosages in mice, and other animals, to humans are known to the art; for example, see U.S. Pat. No. 4,938,949.

Generally, the concentration of the compound(s) of formula I in a liquid composition, such as a lotion, will be from about 0.1–25 wt-%, preferably from about 0.5–10 wt-%. The concentration in a semi-solid or solid composition such as a gel or a powder will be about 0.1–5 wt-%, preferably about 0.5–2.5 wt-%. Single dosages for injection, infusion or ingestion will generally vary between 50–1500 mg, and may be administered, i.e., 1–3 times daily, to yield levels of about 0.5–50 mg/kg, for adults.

Compounds of the invention may also be used as imaging agents when labeled with a radionuclide. As illustrated in FIG. 9, the radionuclide (such as tritium, iodine-125, iodine-131, iodine-123, astatine-210, carbon-11, carbon-14, nitrogen-13, fluorine-18) may be incorporated into X or $X^1$, or attached directly to the core structure, as by halogenation; or the radionuclide (such as Tc-99m, Re-186) may be attached to a linking group or bound by a chelating group which is then attached to the compound of formula II directly, or by means of a linker. Radiolabeling techniques such as these are routinely used in radiopharmaceutical chemistry.

Radiolabeled compounds of the invention are generally useful as imaging agents to diagnose neurological disease (e.g. a neurodegenerative disease) or a mental condition or to follow the progression or treatment of such a disease or condition in a mammal (e.g. a human). The radiolabeled compounds of the invention and can conveniently be used in conjunction with imaging techniques such positron emission tomography (PET) or single photon emission computerized tomography (SPECT).

The pharmacological activity of compounds of the invention can be demonstrated using standard pharmacological models which are known in the art, or can be demonstrated using the models that are described or cited hereinbelow.

Representative compounds of formula II were tested for their ability to displace [$^3$H]WIN-35428 binding from rat striatal membranes and to inhibit the high-affinity uptake of [$^3$H]dopamine into rat striatal nerve endings (synaptosomes) in accordance with protocols previously described by Boja et al. *Mol Pharmacol*. 1991, 39, 339. The results of these assays are provided in Table 1.

TABLE 1

$IC_{50}$ Values for Compounds of Formula II in [$^3$H]WIN 35,428 Binding and in the Inhibition of [$^3$H]Dopamine Uptake

| Compound number | R | X | $IC_{50}$ (nM) [$^3$H]WIN 35,428 binding | $IC_{50}$ (nM) [$^3$H]dopamine uptake |
|---|---|---|---|---|
| cocaine | — | — | 101.6 ± 9.4 | 239.1 ± 1.1 |
| (±)-1 | β-CO$_2$Me | Cl | 53.7 ± 1.9 | 37.8 ± 7.9 |
| (±)-2 | β-CO$_2$Me | Cl | 196.8 ± 7.9 | — |
| (−)-3 | β-CO$_2$Me | Cl | 24.8 ± 1.6 | 85.23 ± 2.6 |
| (+)-4 | β-CO$_2$Me | Cl | 1362 ± 125 | 5092 ± 172 |
| (−)-5 | β-CH$_2$OH | Cl | 75.3 ± 6.2 | 49.0 ± 3.0 |
| (+)-6 | β-CH$_2$OH | Cl | 442 ± 32 | — |
| (−)-7 | β-CH$_2$OAc | Cl | 44.7 ± 10.5 | 62.9 ± 2.7 |
| (+)-8 | β-CH$_2$OAc | CL | 928 ± 43 | 2027 ± 82 |
| (−)-9 | β-nPr | Cl | 3.0 ± 0.5 | 8.3 ± 0.6 |
| (−)-10 | β-CO$_2$Me | H | 769 ± 19 | — |
| (+)-11 | α-CO$_2$Me | Cl | 57.3 ± 8.1 | 34.6 ± 3.2 |
| (−)-12 | α-CO$_2$Me | Cl | 653 ± 38 | 195 ± 8 |
| (+)-13 | α-CH$_2$OH | Cl | 240 ± 18 | 683 ± 47 |
| (+)-14 | α-CH$_2$OAc | Cl | 461 ± 11 | — |
| (+)-15 | α-nPr | Cl | 17.2 ± 0.5 | 23.2 ± 2.2 |

Analog Binding at Neurotransmitters

Determination of inhibitory binding potencies of analogues at dopamine, serotonin, and norepinephrine transporters are carried out using standard receptor binding assays which are known in the art.

A. Dopamine Transporter Binding (DAT)

Dopamine transporters can be assayed using the method described by Boja, J. W., Rahman, M. A., Philip, A., Lewin, A. H., Carroll, F. I. and Kuhar, M. J. (1991) Isothiocyanate derivatives of cocaine: Irreversible of ligand binding at the dopamine transporter. *Mol Pharmacol.*, 39, 339.

B. Serotonin Transporter Binding (5-HTT)

Inhibition of [$^3$H]binding to the serotonin transporter can be assayed according to previously published methods: Boja, J. W., Rahman, M. A., Philip, A., Lewin, A. H., Carroll, F.I. and Kuhar, M. J. (1991) Isothiocyanate derivatives of cocaine: Irreversible of ligand binding at the dopamine transporter. *Mol. Pharmacol.*, 39, 339.

C. Norepinephrine Transporter Binding (NET)

Binding to the norepinephrine transporter can be assayed using a method described by Carroll, F. I., Grey, J., Abraham, P., Kuzemnko, M .A., Lewin, A. H., Boja, J. W., and Kuhar, M. J. (1993) 3-Aryl-2-(3'-substituted-1',2',4'-oxadiazole-5'-yl)tropane analogues of cocaine: Affinities at the cocaine binding site at the dopamine, serotonin, and norepinephrine transporters. *J. Med Chem.*, 36, 2886–2890.

Uptake Studies

A. [³H]Dopamine Uptake Studies

Inhibition of [³H]dopamine uptake can be determined using the method of Boja, J. W., McNeil, R. M., Lewin, A. H., Abraham, P., Carroll, F. I., and Kuhar, M. J. (1992) Selective dopamine transporter inhibition by cocaine analogs. *Neuroreport*, 3, 984.

B. [³H]Serotonin Uptake Studies

Inhibition of [³H]serotonin uptake can be determined in fresh rat hind brain tissue. The assay can be conducted as described above, with some modifications. The final tissue concentration will be approximately 2 mg/mL, and the final [³H]serotonin concentration will be 5.0 nM. Non-specific uptake of [3H]serotonin can be defined using 1 μM citalopram.

C. [³H]Norepinephrine Uptake Studies

Inhibition of [³H]norepinephrine uptake can be determined in fresh rat cortex. The assay can be conducted in a manner similar to that described for [³H]dopamine uptake studies, with some modifications. The final tissue concentration will be approximately 10 mg/mL, and the final [³H]norepinephrine concentration will be 5.0 nM. The non-specific uptake of [³H]norepinephrine can be defined using 1 μM desipramine.

Representative compounds of formula I and II were tested for binding at neurotransmitters and for inhibition of dopamine uptake. The results are shown in Table 2.

TABLE 2

| Compound | DAT IC$_{50}$ (nm) | NET IC$_{50}$ (nm) | 5-HTT IC$_{50}$ (nm) | Dopamine Uptake |
|---|---|---|---|---|
| 11 | 57 | 4196 | 1620 | 34 |
| 3 | 25 | 1634 | — | 85 |
| 5 | 75 | — | — | 49 |
| 7 | 10 | 233 | — | 63 |
| 9 | 3 | — | — | 8 |
| 13 | 240 | — | — | 864 |
| 14 | 461 | — | — | — |
| 15 | 17 | — | — | 23 |
| 4 | 1362 | — | — | 5092 |
| 6 | 442 | — | — | — |
| 8 | 928 | — | — | 2027 |
| 12 | 653 | — | — | 195 |
| 10 | 797 | — | — | — |
| 1 · HCl | 53 | — | — | — |
| 1 | 22 | — | — | — |
| 2 | 196 | — | — | — |
| Cocaine | 101 | 4431 | 1069 | 239 |
| 15 | 55 | 183 | 155 | — |
| 49 | 1966 | — | — | — |
| 46 | 26078 | >10,000 | — | — |
| 47 | 917 | — | — | — |
| 48 | 157 | 1153 | 73,207 | — |
| 73 | 173 | 2704 | 1314 | — |
| 54 | 15 | 563 | 2810 | — |
| 55 | 28 | — | — | — |
| 80 | 28 | — | — | — |
| 56 | 172 | 1130 | >10,000 | — |
| 58 | 289 | — | 7396 | — |
| 59 | 1460 | 56,511 | 25,129 | — |
| 64 | 20 | 65,757 | 13,235 | 212 |
| 65 | 293 | — | 55,682 | — |
| 68 | 1418 | — | — | — |
| 66 | 4406 | — | — | — |
| 81 | 1693 | >10,000 | 15,728 | — |
| 67 | 7344 | — | — | — |
| 60 | 39 | — | — | — |
| 63 | 3 | — | 1099 | — |
| 69 | 406 | 21,568 | 4134 | — |
| 74 | 13 | 2570 | 107 | — |
| 75 | 78 | 607 | 366 | — |
| 83 | 30 | 1336 | 1104 | — |

Generally, compounds of formula II demonstrate an IC$_{50}$ at DAT of 10 μm or less. Additionally, compound 83 was found to demonstrate similar activity and selectivity to the corresponding compound of formula II from which it was prepared. Accordingly, compounds of formula I may be useful as therapeutic agents or as pharmacological tools to further investigate DAT structure and function. In particular, compounds of formula I possessing high potency at DAT and/or high selectivity for DAT over SERT and/or NET may be particularly useful in the methods described herein.

Intravenous Safety

Cocaine and a number of other tropane analogs are potent inhibitors of norepinephrine re-uptake and possess local anesthetic actions. These properties may indicate significant potential for cardiovascular and central nervous system toxicity.

The test compounds with 10 μM or greater affinity for the dopamine transporter can be tested in rats for intravenous safety according to the previously published procedure. Tella, S. R., Korupolu, G. R., Schindler, C. W., and Goldberg, S. R. (1992) Pathophysiological and pharmacological mechanisms of acute cocaine toxicity in conscious rats. *J. Pharmacol. Exp. Ther.*, 262, 936–946.

Behavioral Testing

A. Locomotor activity

The locomotor effects of compound 2 were evaluated using male Swiss Webster mice according to previously published procedures: Izenwasser, S., Terry, P., Heller, B., Witkin, J. M., and Katz, J. L. (1994) Differential relationships among dopamine transporter affinities and stimulant potencies of various uptake inhibitors. *Eur. J. Pharmacol.*, 263, 277–283.

Cocaine (10 mg/kg, i.p.) produced a significant (P<0.05) increase in the distance traveled and stereotypic behavior as compared to saline control responses in Sprague-Dawley rats. In contrast to cocaine, piperidine analog 2 (3–20 mg/kg i.p.) did not alter the distance traveled. However, piperidine 2 at 10 and 20 mg/kg doses produced a small, statistically nonsignificant increase in stereotypic time. The time-course data indicate that this small increase in stereotypic behavior is persistent at 90 minutes following the drug injection, while the stereotypic response to cocaine showed a clear tendency to decline at this time period. Thus the small behavioral responses to the piperidine analog appear to last longer than that of cocaine.

B. Drug-discrimination

Compound 2 was evaluated in the drug discrimination procedure described by: Callahan, P. M., Bryan, S. K., and Cunningham, K. A. (1995) Discriminative stimulus effects of cocaine: antagonism by dopamine D1 receptor blockade in the amygdala. *Pharmacol. Biochem. Behav.*, 51, 759–766.

In Substitution tests, amphetamine administration engendered a dose-dependent and complete substitution for the discriminative stimulus effects of amphetamine, whereas administration of the piperidine analog 2 resulted in a maximum of 53% amphetamine-lever responding. Response rates remained fairly stable across all test doses of amphetamine and piperidine analog 2.

Cocaine (1.25–10 mg/kg) administration resulted in a dose-related increase in cocaine-appropriate responding, whereas piperidine analog 2 (5 and 20 mg/kg) engendered a maximum of 40% cocaine-lever responding. Response rates following piperidine analog 2 (5 and 10 mg/kg) were substantially lower than those observed following cocaine (10 mg/kg) administration. Co-administration of piperidine analog 2 (10 mg/kg) plus cocaine (1.25 and 5 mg/kg) did not significantly alter drug choice [$F(1,7)=1.35$, $p=0.28$] or response rate performance [$F(1,7)=4.84$, $p=0.06$] from that observed following administration of 1.25 and 5 mg/kg of cocaine alone (data not shown). This result is in contrast to other dopamine uptake inhibitors that are known to cause a leftward shift in cocaine's dose-response function. These results suggest that the piperidine analog differs from other uptake inhibitors in lacking the potentiation of cocaine's discriminative stimulus effects.

C. Intravenous Drug Self-administration

Compounds 2 and 3 were evaluated using the intravenous drug self-administration procedures described by: Tella, S. R., Ladenheim, B., Andrews, A. M., Goldberg, S. R., and Cadet, J. L. (1996) Differential reinforcing effects of cocaine and GBR-12909: Biochemical evidence for divergent neuroadaptive changes in the mesolimbic dopaminergic system. *J. Neurosci.*, 16, 7416–7427.

Rats were initially trained to lever press for food pellets in standard operant boxes. Following lever press training, rats were implanted with polyvinyl chloride catheters into femoral veins under halothane anesthesia (2–3% in medical grade oxygen) and were allowed to recover for an additional 7 days before initiation of i.v. drug self-administration testing. During drug self-administration sessions, food pellets were no longer delivered, and instead intravenous injections of drugs were delivered by way of the catheter. Each completion of 10 lever press responses (FR10) resulted in an i.v. infusion of cocaine (1 mg/kg/infusion) delivered over a 1 second period.

Following approximately 3 weeks of cocaine self-administration, the extinction test was done by substituting saline (0.25 ml/kg) for cocaine for 5 days. Following extinction, re-acquisition of cocaine (1 mg/kg/infusion) self-administration was tested for 5 days. Following re-acquisition of cocaine self-administration, the saline extinction test was repeated. Following this second extinction test, self-administration of piperidine analog 2 was studied at doses of 1, 3, and 0.3 mg/kg/infusion in that order. Each dose was tested for five days. During all the re-acquisition test days, a priming infusion was given at the start of the session on each day.

Cocaine maintained significantly ($P<0.05$) higher rates of responding as compared to the responding during the saline extinction test. The substitution of saline for cocaine led to a decline in the response rate. The substitution of piperidine analog 2 (0.3–3 mg/kg/infusion) for saline failed to restore the self-administration responding. The number of infusions of the piperidine analog delivered at all of the doses tested were not significantly different from that of the saline extinction test. These data suggest that the piperidine analog, unlike cocaine, lacks positive reinforcing effects. In contrast, the piperidine analog 3 is cocaine-like in this test, as evidenced by the fact that rats reliably self-administered this compound (0.125–0.5 mg/kg infusion).

D. Effects of Test Compounds on Cocaine Self-administration and Food Reinforcement The effect of pretreatment with test compound on cocaine self-administration can be studied. Five minutes following intravenous injection of test compounds, rats can be tested for cocaine self-administration. The doses that fall on both the ascending and the descending portions of the cocaine dose-response function can be tested following pretreatment with test compounds. This allows for a determination of whether there is a left- or rightward shift or downward shift in the cocaine dose-response function. Compounds showing overall reduction (downward shift) in cocaine self-administration can be further tested for the specificity of this effect. This can be done by studying the effect of test compound on non-drug reinforcers such as food.

PET Evaluation

The cis and trans isomers of 4-(4-chlorophenyl)-3-(carbomethoxy)piperidine were labeled via N-methylation. $^{11}$C-methyl iodide was bubbled into a solution of each of the piperidine isomers (1.5 mg free base in 0.3 cc DMSO) and the mixtures were heated at 110° C. for 7 minutes. The products were purified by HPLC on a C-18 cartridge eluted with MeOH: phosphate/triethylamine buffer, pH 7.2 (60:40). The $^{11}$C-labeled drugs were produced in good radiochemical yield [~15% @EOS]. Radiochemical purities of the final products were >98% and specific activity were routinely >2,000 mCl/μmole [EOS].

After passage through a 0.22 μm filter, the sterile products were administered to three Rhesus monkeys and dynamic PET images were acquired over 90 minutes. Both isomers accumulated rapidly in the striatum with the cis isomer exhibiting greater nonspecific accumulation in the cortex. Studies with low specific activity tracer showed reduced striatal-to-cerebellar ratios compared with high specific activity preparations. When unlabeled CFT was administered 60 minutes after injection of the trans isomers, a selective decrease in the striatal activity was observed; consistent with in vivo binding to the dopamine transporter.

These results establish that both the cis- and trans isomers of 4-(4-chlorophenyl)-3-carbomethoxy-N-methylpiperidine have high levels of specific binding to striatal dopamine transporter sites.

The 3-n-propyl derivative (−)-9 was found to have a binding affinity of 3 nM. Thus compound 9 is 33-fold more potent than cocaine in binding affinity, and 29-fold more potent in its inhibition of dopamine uptake. The above results demonstrate that representative compounds of formula I possess significant binding activity at the dopamine receptor. Accordingly compounds of the invention may be useful as therapeutic agents for the treatment of drug abuse (e.g. cocain addiction). Additionally, compounds of formula I, and in particular, compounds wherein $R^6$ is hydrogen, may also possess activity as serotonin reuptake inhibitors. Accordingly, compounds of formula I may also be useful for inhibiting serotonin reuptake, and thus for treating Parkinson's disease or depression.

The invention will now be illustrated by the following non-limiting examples, wherein unless otherwise stated: starting materials were obtained from Aldrich Chemicals or from other commercial suppliers; diethyl ether and cyclohexane were distilled from phosphorus pentoxide; tetrahydrofuran was freshly distilled under nitrogen from sodium-benzophenone; infrared ("IR") spectra were recorded on an ATI Mattson Genesis spectrometer; proton $^1$H and carbon $^{13}$C nuclear magnetic resonance ("NMR") spectra were obtained with a Varian Unity Inova instrument at 300 and 75.46 MHZ; $^1$H chemical shifts ($\delta$) are reported in ppm downfield from internal TMS; $^{13}$C chemical shifts are referred to CDCl$_3$ (central peak, $\delta$=77.0 ppm), benzene-d$_6$ (central peak, $\delta$=128.0 ppm), or DMSO-d$_6$ (central peak, $\delta$=39.7 ppm); when appropriate NMR assignments were made with the help of COSY, DEPT, and HETCOR experiments; melting points were determined in Pyrex capillaries with a Thomas Hoover Unimelt apparatus and are uncorrected; mass spectra were measured in the EI mode at an ionization potential of 70 eV; thin layer chromatography ("TLC") was performed on Merck silica gel 60F$_{254}$ glass plates; column chromatography was performed using Merck silica gel (60–200 mesh); preparative thin layer chromatography ("PTLC") was performed on silica gel plates; compounds gave satisfactory combustion analysis; and the following abbreviations are used: DMSO=dimethyl sulfoxide; ether=diethyl ether; THF=tetrahydrofuran; and DCM=dichloromethane.

EXAMPLES

The invention now being generally described, it will be more readily understood by reference to the following examples, which are included merely for purposes of illustration of certain aspects and embodiments of the present invention, and are not intended to limit the invention.

Example 1

(±)-cis-Methyl 4-(4-Chlorophenyl)-1-methylpiperidine-3-carboxylate (1)

To a solution of 4-chlorophenylmagnesium bromide (166 mL, 1.0 M in ether) in ether (700 mL) was added dropwise at –10° C. a solution of arecoline free base (12.9 g, 83 mmol, obtained from the hydrobromide by treatment with sodium bicarbonate and extraction into methylene chloride) in ether (300 mL). The mixture was stirred at –10° C. for 30 minutes, then poured onto crushed ice and treated slowly with 10% HCl (200 mL). The aqueous layer was separated, washed with ether (200 mL), and treated, while cooling in an ice bath, with a saturated solution of sodium bicarbonate (100 mL). The mixture was extracted with ether (2×200 mL), and the combined organic phases were washed with brine (200 mL), dried, and concentrated under reduced pressure. The crude mixture was crystallized from EtOAc/hexane to afford the title compound 1 (5.0 g, 22%) as a white solid. Concentration of the mother liquor gave a mixture of compounds 1 and 2 that was separated by flash chromatography on silica gel using ether/Et$_3$N 9/1 as eluent to give additional title compound (total 12.4 g, 56%): mp 98–99° C.; $^1$H NMR (CDCl$_3$) $\delta$ 1.74–1.86 (m, H$_{5eq}$), 2.07 (dt, H$_{6ax}$, J=3.0 and 11.4 Hz), 2.28 (s, 3H), 2.35 (dd, H$_{2'}$, J=3.6 and 11.7 Hz), 2.66 (dq, H$_{5ax}$, J=3.9 and 12.0 Hz), 2.78 (dt, H$_4$, J=3.6 and 12.0 Hz), 2.9–3.06 (m, H$_3$ and H$_{6eq}$), 3.18 (bd, H$_{2''}$, J=12.0 Hz), 3.52 (s, 3H), 6.2–6.35 (m, 4H); $^{13}$C NMR (CDCl$_3$) $\delta$ 26.42 (C$_5$), 41.27 (C$_4$), 46.06 (C$_3$), 46.53 (C$_7$), 51.25 (C$_9$), 55.88 (C$_6$), 58.36 (C$_2$), 128.08 (C$_{11}$, C$_{15}$), 128.95 (C$_{12}$, C$_{14}$), 131.79 (C$_{13}$), 141.54 (C$_{10}$), 172.47 (C$_8$); MS m/z (%) 267 (M$^+$, 7), 208 (14), 128 (6), 70 (29), 44 (100).

Compound 1 was dissolved in a methanolic solution of hydrochloric acid gas and the resulting solid was triturated with ether to give compound 1 HCl: $^1$H NMR (methanol-d$_4$) $\delta$ 2.05 (bd, 1H, J=4.0 Hz), 2.53 (bq, 1H, J=10.8 Hz), 2.94 (s, 3H), 3.14–3.5 (m, 4H), 3.45 (s, 3H), 3.6–3.7 (m, 1H), 3.78 (d, 1H, J=12.9 Hz), 7.22 (d, 2H, J=8.4 Hz), 7.35 (d, 2H, J=8.4 Hz).

Example 2

(±)-trans-Methyl 4-(4-Chlorophenyl)-1-methylpiperidine-3-carboxylate (2)

Concentration of the mother liquor from Example 1 gave a mixture of compounds 1 and 2. Flash chromatography on silica gel using ether/Et$_3$N 9/1 as eluent gave compound 2 (2.0 g, 18%): $^1$H NMR (benzene-d$_6$) $\delta$ 1.4–1.5 (m, 1H), 1.62 (dq, 1H, J=3.9 and 12.6 Hz), 1.75 (dt, 1H, J=2.7 and 12.0 Hz), 2.06 (s, 3H), 2.0–2.15 (m, 1H), 2.54–2.63 (m, 1H), 2.68 (dt, 1H, J=4.2 and 11.7 Hz), 2.86–3.0 (m, 2H), 3.08 (s, 3H), 6.87 (d, 2H, J=8.7 Hz), 7.07 (d, 2H), J=8.7 Hz); $^{13}$C NMR (CDCl$_3$) $\delta$ 33.1, 44.0, 46.1, 49.1, 51.5, 55.7, 58.1, 128.6, 128.7, 132.3, 141.9, 173.4; MS m/z (%) 267 (M$^+$, 17), 208 (30), 128 (16), 114 (16), 43 (100).

Using a procedure similar to that described in Example 1, the hydrochloride salt of compound 2 was prepared: compound 2·HCl: $^1$H NMR (methanol-d$_4$) $\delta$ 2.04–2.16 (m, 2H), 2.97 (s, 3H), 3.0–3.3 (m, 4H), 3.47 (s, 3H), 3.56–3.66 (m, 1H), 3.7–3.8 (m, 1H), 7.25 (d, 2H, J=8.4 Hz), 7.34 (d, 2H, J=8.4 Hz).

Example 3

(–)-Methyl 4$\beta$-(4-Chlorophenyl)-1-methylpiperidine-3$\beta$-carboxylate (3)

To a solution of compound 1 (6.4 g, 24 mmol) in MeOH (200 mL) was added a solution of dibenzoyl-L-tartaric acid (8.9 g, 24 mmol) in MeOH (100 mL). The resulting mixture was stirred at room temperature for 5 hours, filtered, and the white precipitate washed with MeOH (20 mL). This tartrate salt was treated with a saturated solution of NaHCO$_3$ (150 mL) and the mixture extracted with CHCl$_3$ (3×100 mL). The combined organic phases were washed with brine (150 mL), dried, and concentrated under reduced pressure to afford the title compound (2.0 g) as a white solid: mp 98–99° C.; $[\alpha]^{25}_D$ –56° (c 1.0, EtOH).

Using a procedure similar to that described in Example 1, the hydrochloride salt of compound 3 was prepared: compound 3·HCl; $[\alpha]^{25}_D$ –130° (c 1.0, EtOH).

Single Crystal X-Ray Analysis was preformed on the (–)-Dibenzoyltartrate of (3) as described below. A clear rectangular 0.06×0.08×0.52 mm crystal, C$_{14}$H$_{19}$O$_2$ClN$^+$ C$_{18}$H$_{13}$O$_8^-$, FW=626.04, was selected for data collection. Data were collected on a computer controlled Siemens CCD 1K area detector system with a Siemens PLATFORM goniometer using a Rigaku rotating anode source and Gobel mirrors (Cu K$\alpha$ radiation, $\lambda$=1.54178 Å, T=295 K). Data collection nominally covered a hemisphere in reciprocal space by combining six sets of exposures with different 2$\theta$ and $\phi$ angles: each exposure covered a range of 0.75° in $\omega$. The crystal to detector distance was 5.09 cm, and coverage of a unique set was 98% complete to 1.0 Å resolution. The crystal decay was monitored by repeating 50 of the initial frames at the end of data collection and was found to be 2.7%. A least-squares refinement using 176 centered reflections within 16.2<2$\theta$<34.4° gave the orthorhombic P2$_1$2$_1$2$_1$ cell, a=7.752(3), b=14.691(5), c=27.502(8) Å, with V=3132.2 (17) Å$^3$, Z=4, and d$_{calc}$=1.328 gm/cm$^3$. A total of 8342 reflections were to 2$\theta_{max}$=100°, of which there were 2923 independent reflections. Corrections were applied for Lorentz and polarization effects. An empirical absorption correction was applied using equivalent reflections (SADABS), $\mu$=1.577 mm$^{-1}$. Max. and min. transmission were 0.44 and 0.88, respectively. The structure was solved by direct methods with the aid of the program SHELXT1 and refined on $F^2$ with full matrix least-squares. The 398 parameters refined include the coordinates and anisotropic thermal parameters for all non-hydrogen atoms. Hydrogens were included using a riding model. The final R values for the 2244 observed reflections with $F_o>4\sigma(|F_o|)$ were R=0.086 and wR($F^2$)=0.208. The goodness of fit parameter was 1.07, and final difference Fourier excursions were 0.41 and −0.27 e$Å^{-3}$. The absolute configuration determination was based on a method suggested by D. Rogers. The absolute structure parameter which should be near 0.0 for the correct choice of chirality and 1.0 for an incorrect choice was 0.04(6). The compound also contained a chiral anion, (−)-dibenzoyltartaric acid.

Example 4

(+)-Methyl 4β-(4-Chlorophenyl)-1-methylpiperidine-3β-carboxylate (4)

To the mixture of enantiomers derived from the mother liquor of Example 3 (4.2 g, 15.7 mmol) in MeOH (150 mL) was added a solution of dibenzoyl-D-tartaric acid (5.8 g, 15.7 mmol) in MeOH (50 mL). The resulting mixture was stirred at oom temperature 5 hours, filtered, and the white precipitate was washed with MeOH (10 mL). This tartrate salt was treated with a saturated solution of NaHCO$_3$ (100 mL) and the mixture extracted with CHCl$_3$ (3×70 mL). The combined organic phases were washed with brine (150 mL), dried, and concentrated under reduced pressure to afford the title compound (2.2 g) as a white solid: mp 98–99° C.; $[\alpha]^{25}_D$+56° (c 1.0, EtOH).

The hydrochloride salt was prepared by dissolution of the free base of compound 4 in a methanolic solution of HCl(g), concentration, and final trituration of the crude salt with ether: $[\alpha]^{25}_D$+126° (c 1.0, EtOH).

Example 5

(−)-4β-(4-Chlorophenyl)-3β-(hydroxymethyl)-1-methylpiperidine (5)

To a solution of 3 (1.0 g, 3.7 mmol) in THF (30 mL) was added portionwise LiAlH$_4$ (0.3 g, 7.5 mmol). The resulting mixture was stirred at room temperature for 2 hours. A saturated solution of Rochelle salt (30 mL) was added followed by extraction with EtOAc (100 mL). The organic phase was washed with brine (100 mL), dried, and concentrated under reduced pressure to afford the title compound (0.9 g, 98%) as a colorless oil: $[\alpha]^{25}_D$−70° (c 1.0, EtOH); $^1$H NMR (CDCl$_3$) δ 1.64–1.84 (m, H$_3$ and H$_{5eq}$), 2.11 (dt, H$_{6ax}$, J=3.3 and 11.7 Hz), 2.29 (s, 3H), 2.45 (dt, H$_{1'}$, J=2.7 and 11.4 Hz), 2.55 (dq, H$_{5ax}$, J=4.2 and 12.6 Hz), 2.84 (dt, H$_4$, J=4.5 and 13.5 Hz), 3.0–3.1 (m, H$_{6eq}$), 3.14 (br d, H$_{2''}$, J=11.4 Hz), 3.54 (dt, H$_8$, J=2.4 and 10.8 Hz), 3.70 (dd, H$_8$, J=3.3 and 11.1 Hz), 7.24 (d, 2H, J=8.7 Hz), 7.29 (d, 2H, J=8.7 Hz); $^{13}$C NMR (CDCl$_3$) δ 27.9 (C$_4$), 40.2 (C$_2$), 43.5 (C$_3$), 46.3 (C$_6$), 56.2 (C$_1$), 61.4 (C$_5$), 64.5 (C$_8$), 128.4 (C$_{11}$, C$_{15}$), 129.2 (C$_{12}$, C$_{14}$), 131.9 (C$_{13}$), 142.1 (C$_{10}$); MS m/z (%) 239 (M$^+$, 6), 208 (6), 100 (16), 44 (100).

Example 6

(+)-4β-(4-Chlorophenyl)-3β-(hydroxymethyl)-1-methylpiperidine (6)

Using a procedure similar to that described in Example 5, except replacing the compound 3 used therein with compound 4, the title compound 6 was prepared (82%) as a colorless oil; $[\alpha]^{25}_D$+67° (c 1; EtOH).

Example 7

(−)-3β-(Acetoxymethyl)-4β-(4-chlorophenyl)-1-methylpiperidine (7)

To a solution of compound 5 (90 mg, 0.38 mmol) in pyridine (2 mL) was added acetic anhydride (0.5 mL). The resulting solution was stirred at room temperature for 15 hours, concentrated under reduced pressure, diluted with EtOAc (30 mL), and washed with a saturated solution of NH$_4$Cl (2×20 mL). The organic solution was dried and concentrated under reduced pressure to afford the title compound (0.10 g, 95%) as a white solid: mp 76° C.; $[\alpha]^{25}_D$ −109° (c 0.75; EtOH); R$_f$ 0.6 (ether/Et$_3$N 9.5/0.5); $^1$H NMR (benzene-d$_6$) δ 1.21 (br d, 1H, J=11.4 Hz), 1.52 (s, 3H), 1.72 (dq, 1H, J=3.0 and 12.3 Hz), 1.6–1.7 (m, 1H), 1.86 (dd, 1H, J=2.7 and 11.4 Hz), 2.0–2.1 (m, 1H), 2.09 (s, 3H), 2.40 (dt, 1H, J=3.9 and 11.4 Hz), 2.67 (br d, 1H, J=8.1 Hz), 2.91 (d, 1H, J=11.4 Hz), 3.90 (dd, 1H, J=4.5 and 10.8 Hz), 4.47 (dd, 1H, J=9.6 and 10.5 Hz), 6.68 (d, 2H, J=8.4 Hz), 7.09 (d, 2H, J=8.4 Hz); $^{13}$C NMR (CDCl$_3$) δ 20.8, 25.6, 39.6, 41.9, 46.5, 56.2, 57.8, 62.5, 128.4, 128.5, 132.0, 141.5, 170.9; MS m/z (%) 281 (M$^+$, 6), 238 (6), 208 (15), 142 (7), 44 (100).

Example 8

(+)-3β-(Acetoxymethyl)-4β-(4-chlorophenyl)-1-methylpiperidine (8)

Using a procedure similar to that described in Example 7, except replacing compound 5 used therein with compound 6, the title compound 8 was prepared (93%) as a white solid: $[\alpha]^{25}_D$+107° (c 0.35; EtOH); MS m/z (%) 281 (M$^+$, 6).

Example 9

(−) 4β-(4-Chlorophenyl)-1-methyl-3β-n-propylpiperidine (9)

Oxalyl chloride (0.19 mL) was dissolved in anhydrous CH$_2$Cl$_2$ (15 mL), and the solution was cooled to −78° C. Dimethyl sulfoxide (0.32 mL) was added, after 5 minutes, alcohol 5 (0.5 g, 2.08 mmol) was added in CH$_2$Cl$_2$ (5 mL), and stirring was continued for 30 minutes. The reaction mixture was quenched by adding Et$_3$N (2.84 mL), and the resulting solution was warmed to room temperature, diluted with CH$_2$Cl$_2$ (30 mL), washed with NH$_4$Cl (2×30 mL), dried, and concentrated under reduced pressure to provide the intermediate aldehyde (0.45 g, 91%) as a colorless oil used in the next step without further purification: $^1$H NMR (CDCl$_3$) δ 1.9–2.0 (m, 1H), 2.10 (dt, 1H, J=2.4 and 11.4 Hz), 2.29 (s, 3H), 2.2–2.4 (m, 2H), 2.64–2.74 (m, 1H), 2.92 (dt, 1H, J=3.9 and 12.9 Hz), 3.0–3.1 (m, 1H), 3.28 (br d, 1H, J=11.4 Hz), 7.2 (d, 2H, J=8.4 Hz), 7.29 (d, 2H, J=8.4 Hz), 8.7 (s, 1H), $^{13}$C NMR (CDCl$_3$) δ 27.2, 40.9, 46.5, 51.9, 55.9, 57.0, 128.6, 128.7, 132.3, 140.6, 203.9.

A solution of n-BuLi (2.28 mL, 1 M in hexane, 5.7 mmol) was dissolved in THF (10 mL) and cooled to 0° C. Ethyltriphenylphosphonium bromide (2.1 g, 5.7 mmol) was added slowly under nitrogen. The resulting yellow-orange solution was stirred at 0° C. for 30 minutes, and the cooling bath was removed. The crude aldehyde (0.45 g, 1.9 mmol) was added in THF (2 mL), and the reaction mixture was stirred for 15 hours at room temperature, diluted with EtOAc (20 mL), and washed with a saturated solution of NH$_4$Cl (2×30 mL). The organic phase was extracted with 10% HCl (3×10 mL). The combined aqueous phases were washed with EtOAc (30 mL), neutralized with a saturated solution of NaHCO$_3$, and extracted with CH$_2$Cl$_2$ (2×30 mL). The combined organic phases were dried and concentrated under reduced pressure, and the residue was purified by flash chromatography on silica gel using ether/Et$_3$N 9.5/0.5 as eluent to afford an olefin intermediate as a mixture of cis and trans isomers (0.3 g, 63%): MS m/z (%) 248 (M$^+$, 6), 57 (100).

To a solution of the olefins (0.2 g, 0.80 mmol) in cyclohexane (20 mL) was added 5% Pt/C (0.2 g). The mixture was stirred at room temperature for 30 minutes under H$_2$ (40 psi). The solution was filtered over celite and evaporated to dryness. The resulting colorless oil was purified by flash chromatography on silica gel using ether/Et$_3$N 9.5/0.5 as eluent to afford the title compound 9 (0.19 g, 94%) as a colorless oil: $[\alpha]^{25}_D$ −84° (c 0.5, EtOH); $^1$H NMR (benzene-d$_6$) δ 0.71 (t, 3H, J=6.9 Hz), 0.75–1.0 (m, 2H), 1.2–1.4 (m, 2H), 1.52–1.65 (m, 1H), 1.65–1.84 (m, 2H), 1.84–2.0 (m, 2H), 2.14 (s, 3H), 2.47 (dt, 1H, J=3.6 and 12.3 Hz), 2.7–2.84 (m, 1H), 6.77 (d, 2H, J=8.4 Hz), 7.15 (d, 2H, J=8.4 Hz); $^{13}$C NMR (CDCl$_3$) δ 14.0, 21.1, 25.4, 27.6, 40.2, 43.9, 46.8, 56.5, 59.4, 128.1, 128.8, 131.4, 142.9; MS m/z (%) 251 (M$^+$, 8), 208 (8), 112 (24), 44 (100).

The hydrochloride salt was prepared by dissolution of the free base in a methanolic solution of HCl(g), concentration, and final trituration of the crude salt with ether: mp>230° C.; $[\alpha]^{25}_D$ −73° (c 0.25, EtOH); $^1$H NMR (methanol-d$_4$) δ 0.78 (t, 3H, J=6.6 Hz), 0.9–1.1 (m, 2H), 1.28–1.5 (m, 2H), 1.94–2.06 (m, 1H), 2.14–2.38 (m, 2H), 2.92 (s, 3H), 3.04–3.4 (m, 3H), 3.54–3.7 (m, 2H), 7.24 (d, 2H, J=7.8 Hz), 7.35 (d, 2H, J=7.8 Hz).

Example 10

(−)-Methyl 1-Methyl-4β-phenylpiperidine-3β-carboxylate (10)

A mixture of compound 3 (0.7 g, 2.61 mmol) and 10% Pd/C (0.28 g) in MeOH (20 mL) was hydrogenated under 1 atm of H$_2$ for 3 hours. The resulting mixture was filtered over celite and evaporated to dryness. The resulting pale yellow oil was purified by flash chromatography on silica gel using ether/Et$_3$N 9.5/0.5 as eluent to afford the title compound (0.6 g, 98%) as a colorless oil: $[\alpha]^{25}_D$ −54° (c 1; EtOH); $^1$H NMR (CDCl$_3$) δ 1.76–1.9 (m, H$_{5eq}$), 2.09 (dt, H$_{6ax}$, J=2.7 and 11.1 Hz), 2.29 (s, 3H), 2.37 (dd, H$_{2'}$, J=3.6 and 11.7 Hz), 2.70 (dq, H$_{5ax}$, J=3.9 and 12.3 Hz), 2.85 (dt, H$_4$, J=3.9 and 11.7 Hz), 2.92–3.06 (m, H$_3$ and H$_{6eq}$), 3.18 (br d, H$_{2''}$, J=12.0 Hz), 3.50 (s, 3H), 7.1–7.4 (m, 5H); $^{13}$C NMR (CDCl$_3$) δ 26.6, 41.8, 46.2, 46.6, 51.2, 55.9, 58.3, 126.1, 127.6, 128.0, 143.0, 172.7; MS m/z (%) 233 (M$^+$, 13), 232 (6), 174 (17), 70 (26), 44 (100).

The hydrochloride salt was prepared by dissolution of the free base in a methanolic solution of HCl(g), concentration, and final trituration of the crude salt with ether:$[\alpha]^{25}_D$ −130° (c 1.0, EtOH); mp 168–169° C.; $^1$H NMR (methanol-d$_4$) δ 2.0–2.1 (m, 1H), 2.5–2.7 (m, 1H), 2.95 (s, 3H), 3.1–3.5 (m, 4H), 3.42 (s, 3H), 3.6–3.7 (m, 2H), 3.7–3.85 (1H), 7.2–7.4 (m, 5H).

Example 11

(+)-Methyl 4β-(4-Chlorophenyl)-1-methylpiperidine-3α-carboxylate (11)

To a solution of compound 3 (0.5 g, 1.87 mmol) in MeOH (6 mL) was added a 30% methanolic solution of sodium methoxide (0.04 mL). The resulting solution was stirred at reflux for 24 hours and concentrated under reduced pressure. CH$_2$Cl$_2$ and brine were added, and the organic layer was washed with brine. Concentration of the combined organic phase afforded compound 3 and compound 11 in a 1:32 ratio (determined by GC-MS analysis). Purification of the crude product by silica gel flash chromatography using ether/Et$_3$N 9.8/0.2 as eluent afforded the title compound (0.43 g, 86%) as a colorless oil: $[\alpha]^{25}_D$ +46° (c 1.0, EtOH).

The hydrochloride salt was prepared by dissolution of the free base in a methanolic solution of HCl(g), resulting in a direct crystallization of the desired salt: $[\alpha]^{25}_D$ +55° (c 0.5, EtOH); mp>230° C.

Example 12

(−)-Methyl 4β-(4-Chlorophenyl)-1-methylpiperidine-3α-carboxylate (12)

To a solution of compound 4 (0.4 g, 1.49 mmol) in MeOH (3 mL) was added a 30% methanolic solution of sodium methoxide (0.01 mL). The resulting solution was stirred at reflux for 11 hours and concentrated under reduced pressure. CH$_2$Cl$_2$ and a saturated solution of NH$_4$Cl were added. The organic layer was washed with brine, dried over sodium sulfate, and concentrated under reduced pressure to afford compounds 4 and 12 in a 1:5.6 ratio (determined by GC-MS analysis). Purification of the crude product by silica gel flash chromatography using ether/Et$_3$N 9.8/0.2 as eluent afforded the title compound (0.35 g, 85%) as a colorless oil: $[\alpha]^{25}_D$ −50° (c 1.0, EtOH).

Example 13

(+)-4β-(4-Chlorophenyl)-3α-(hydroxymethyl)-1-methylpiperidine (13)

Using a procedure similar to that described in Example 5, except replacing the compound 3 used therein with compound 11, the title compound was obtained (84%) as a colorless oil: $[\alpha]^{25}_D$ +38° (c 0.5; EtOH); mp 148–150° C.; $^1$H NMR (CDCl$_3$) δ 1.4 (br s, OH), 1.7–2.1 (m, 5H), 2.29 (dd, 1H, J=5.4 and 10.5 Hz), 2.36 (s, 3H), 2.95 (d, 1H, J=10.8 Hz), 3.15 (d, 1H, J=10.8 Hz), 3.24 (dd, 1H, J=6.6 and 10.8 Hz), 3.41 (dd, 1H, J=3.0 and 10.8 Hz), 7.14 (d, 2H, J=8.4 Hz), 7.27 (d, 2H, J=8.4 Hz).

Example 14

(+)-3α-(Acetoxymethyl)-4β-(4-chlorophenyl)-1-methylpiperidine (14)

Using a procedure similar to that described in Example 7, except replacing compound 5 used therein with compound 13, the title compound was obtained (80%) as a white solid: $^1$H NMR (CDCl$_3$) δ 1.7–1.9 (m, 3H), 1.97 (s, 3H), 1.95–2.1 (m, 1H), 2.1–2.3 (m, 2H), 2.35 (s, 3H), 2.95 (d, 1H, J=11.4Hz), 3.07 (d, 1H, J=9.6 Hz), 3.63 (dd, 1H, J=7.5 and 11.4 Hz), 3.82 (dd, 1H, J=3.0 and 11.1 Hz), 7.12 (d, 2H, J=8.4 Hz), 7.27 (d, 2H, J=8.4 Hz); $^{13}$C NMR (CDCl$_3$) δ 20.7, 34.4, 41.0, 44.2, 46.4, 56.0, 59.3, 65.2, 128.7, 128.8, 132.2, 142.1, 170.9.

Example 15

(+) 4β-(4-Chlorophenyl)-1-methyl-3α-n-propylpiperidine (15)

To a solution of the olefins prepared in sub-part b below, (550 mg, 2.22 mmol) in 50 mL of cyclohexane was added 825 mg of 5% Pt/C. The mixture was stirred at room temperature for 2 h under a hydrogen atmosphere at 40 psi, and then it was filtered through a Celite column using MeOH as the eluent. Flash chromatography of the residue obtained after concentration of the MeOH washings afforded the title compound (520 mg, 96%): $[\alpha]^{25}_D$ +418 (c 1.0, EtOH); $^1$H NMR (CDCl$_3$) δ 0.73 (t, 3H, J=7.2 Hz), 0.8–1.0 (m, 1H), 1.0–1.2 (m, 2H), 1.2–1.4 (m, 1H), 1.65 (t, 1H, J=10.8 Hz), 1.7–1.9 (m, 3H), 1.9–2.15 (m, 2H), 2.32 (s, 3H), 2.93 (d, 1H, J=11.1 Hz), 3.05 (d, 1H, J=10.8 Hz), 7.10 (d, 2H, J=8.4 Hz), 7.25 (d, J=8.1 Hz); $^{13}$C NMR (CDCl$_3$) d 14.1, 19.7, 33.9, 35.0, 40.8, 46.5, 48.2, 56.3, 61.6, 128.5, 129.0, 131.6, 143.8.

The hydrochloride salt was prepared by dissolution of the free base in a methanolic solution of HCl(g), concentration, and final trituration of the crude salts with ether: $[\alpha]^{25}_D$ +348 (c 0.25, EtOH); mp 216° C. (EtOAc); $^1$H NMR (methanol-d$_4$) δ 0.77 (t, 3H, J=6.9 Hz), 1.0–1.4 (m, 4H), 1.9–2.2 (m, 3H), 2.56 (q, 1H, J=10.8 Hz), 2.86 (t, 1H, J=12.6 Hz), 2.93 (s, 3H), 3.0–3.2 (m, 1H), 3.5–3.7 (m, 2H), 7.23 (d, 2H, J=8.4 Hz), 7.35 (d, 2H, J=8.4 Hz).

The intermediate olefins were prepared as follows.

a. (+)-4β-(4-Chlorophenyl)-3α-formyl-1-methylpiperidine. To a solution of oxalyl chloride (0.28 mL, 3.2 mmol) in 28 mL of anhydrous CH$_2$Cl$_2$ was added DMSO (0.47 mL) at −78° C. After 5 min, the compound of Example 13 (740 mg, 3.1 mmol) in 17 mL of CH$_2$Cl$_2$ was added. The reaction was continued for 2 h at −78° C. and was quenched by adding 4.5 mL of Et$_3$N. The mixture was warmed to room temperature, diluted with CH$_2$Cl$_2$, and washed with NH$_4$Cl, dried and concentrated to afford 740 mg of the aldehyde which was used immediately in the next reaction.

b. (+)-3(-((1-Z) Prop-1-enyl)-4(-(4-chlorophenyl)-1-methylpiperidine and (+)-3(-((1-E) Prop-1-enyl)-4(-(4-chlorophenyl)-1-methylpiperidine. To a solution of n-BuLi (3.8 mL, 2.5 M in hexanes, 9.5 mmol) in THF (17 mL) was added Ph$_3$P—CH$_2$CH$_3$+Br (3.53 g, 9.51 mmol) at 0° C. under nitrogen. The resulting yellow orange solution was stirred at 0° C. for 0.5 h and then was added to the solution of the aldehyde (740 mg) in 18 mL of THF at 0° C. The mixture was stirred at room temperature for 2 h, 50 mL of EtOAc was added, and the resulting solution was washed with NH$_4$Cl. The organic phase was extracted with 10% of HCl, and the aqueous extracts were neutralized with saturated NaHCO$_3$ and extracted with CH$_2$Cl$_2$. The organic extracts were washed with brine, dried and concentrated. Flash chromatography afforded the olefin mixture (560 mg, 72%). This mixture was not characterized further, and was used in the hydrogenation reaction.

Example 16

(−)-Methyl 4β-(4-Chlorophenyl)-piperidine-3β-carboxylate (45)

To a solution of the compound of Example 3 (300 mg, 1.18 mmol) in dichloromethane (30 mL) was added 1,8-bis-(dimethylamino)-naphthalene (proton sponge, 140 mg, 0.66 mmol) and a-chloroethyl chloroformate (1 mL, 9.26 mmol). This mixture was heated under reflux for 1.5 h. After cooling to room temperature, 437 mL of 1 M anhydrous hydrogen chloride in ether solution was added, and the mixture was passed through a silica gel plug and eluted with CH$_2$Cl$_2$. The combined eluents were evaporated. Methanol (26 mL) was added to the residue, and the mixture was stirred at reflux for 1 h. After evaporation 0.5 M KOH was added, and the mixture was extracted with EtOAc, washed with brine, dried, and concentrated. PTLC afforded the title compound (209 mg, 73.5%): $[\alpha]_D$ −143.0 ((c 1.30, CHCl$_3$); $^1$H NMR (CDCl$_3$) d 1.62–1.73 (m, 1H), 2.34 (dq, 1H, J=3.9, 12.6 Hz), 2.68–2.84 (m, 2H), 2.93–3.16 (m, 3H), 3.34 (t, 2H, J=13.5 Hz), 3.45 (s, 3H), 7.12 (d, 2H, J=8.4 Hz), 7.26 (d, 2H, J=8.4 Hz); $^{13}$C NMR (CDCl$_3$) d 26.7, 42.9, 45.7, 46.4, 48.9, 51.3, 128.6, 128.7, 132.5, 141.8, 174.0; MS m/z 43 (25), 57 (100), 194 (41), 253 (M$^+$, 20).

Example 17

(−)-Methyl 4β-(4-Chlorophenyl)-1-phenylsulfonyl-piperidine-3β-carboxylate (46)

To a solution of 45 (42 mg, 0.17 mmol) in 5 mL of CH$_2$Cl$_2$ were added Et$_3$N (48 mL, 0.33 mmol) and PhSO$_2$Cl (25 mL, 0.20 mmol). The reaction mixture was stirred at room temperature for 2 h. After evaporation, the residue was purified by PTLC to afford the title compound (51 mg, 82%): mp 76–78; $[\alpha]_D$ −9.8 ((c 0.44, CHCl$_3$); IR (KBr) 1169, 1236, 1493, 1740, 2853 cm$^{-1}$; $^1$H NMR (CDCl$_3$) d 1.82–1.92 (m, 1H), 2.58 (dt, 1H, J=2.7, 11.1 Hz), 2.72 (dq, 1H, J=3.6, 12.0 Hz), 2.56–2.87 (m, 2H), 2.97–3.04 (m, 1H), 3.55 (s, 3H), 3.86 (dd, 1H, J=1.8, 11.7 Hz), 4.09 (dq, 1H, J=1.8, 12.0 Hz), 7.14 (d, 2H, J=8.4 Hz), 7.24 (d, 2H, J=8.4 Hz), 7.52–7.66 (m, 3H), 7.77–7.84 (m, 2H); $^{13}$C NMR (CDCl$_3$) d 26.1, 41.5, 45.3, 46.3, 48.7, 51.9, 127.8, 128.6, 129.1, 129.3, 132.6, 133.1, 136.7, 140.4, 171.0; MS m/z 42 (22), 220 (15), 252 (100); Anal. (C$_{19}$H$_{20}$ClNO$_4$S) Calcd: C 57.94, H 5.12, N 3.56; Found: C 58.25, H 4.90, N 3.56.

Example 18

(−)-Methyl 4β-(4-Chlorophenyl)-1-benzylpiperidine-3β-carboxylate (47)

To a solution of 45 (37 mg, 0.15 mmol) in acetone (9 mL) was added benzyl bromide (60 mL, 0.50 mmol), Et$_3$N (0.11 mL, 0.77 mmol), and KI (43 mg, 0.26 mmol). The resulting mixture was heated under reflux for 2 h, and then concentrated under reduced pressure. The crude residue was diluted with CH$_2$Cl$_2$ (30 mL), washed with brine, dried, and concentrated. PTLC afforded 42 mg (83%) of the title compound as a white solid: mp 119–121° C.; $[\alpha]_D$ −23.0 ((c 0.56, CHCl$_3$); IR (KBr) 1170, 1492, 1734, 2801 cm$^{-1}$; $^1$H NMR (CDCl$_3$) d 1.76–1.86 (m, 1H), 2.24 (dt, 1H, J=3.0, 11.4 Hz), 2.34 (dd, 1H, J=3.0, 11.4 Hz), 2.62–2.85 (m, 2H), 2.90–2.96 (m, 1H), 3.06 (d, 1H, J=11.1 Hz), 3.22 (d, 1H, J=11.4 Hz), 3.42 (d, 1H, J=13.5 Hz), 3.49 (s, 3H), 3.67 (d, 1H, J=13.2 Hz), 7.30 (m, 9H); $^{13}$C NMR (CDCl$_3$) d 26.7, 42.1, 46.5, 51.3, 54.3, 56.2, 62.7, 127.2, 128.3, 128.9, 129.3, 132.0, 138.7, 142.0, 172.6; MS m/z 42 (8), 91 (100), 252 (26), 343 (M$^+$, 7); Anal. (C$_{20}$H$_{22}$ClNO$_2$) Calcd: C 69.86, H 6.45, N 4.07; Found: C 69.80, H 6.18, N 4.06.

Example 19

(−)-Methyl 4β-(4-Chlorophenyl)-1-(3-phenylpropyl)-piperidine-3β-carboxylate (48)

To a solution of 45 (41 mg, 0.16 mmol) in acetone (10 mL) was added Ph(CH$_2$)$_3$OTs (145 mg, 0.53 mmol), Et$_3$N (0.11 mL, 0.77 mmol) and KI (44 mg, 0.27 mmol). The resulting mixture was heated under reflux for 2 h, and then it was concentrated under reduced pressure. The crude residue was diluted with CH$_2$Cl$_2$ (30 mL), washed with brine, dried and concentrated. PTLC afforded 25 mg (42%) of the title compound as a white solid: mp 73–75° C.; $[\alpha]_D$ −15.6 ((c 0.59, CHCl$_3$); IR (KBr) 700, 1165, 1493, 1742, 2946 cm$^{-1}$; $^1$H NMR (CDCl$_3$) d 1.80 (q, 3H, J=7.5 Hz), 2.15 (dt, 1H, J=2.7, 11.1 Hz), 2.24–2.46 (m, 3H), 2.55–2.72 (m, 3H), 2.80 (dt, 1H, J=3.9, 11.7 Hz), 2.94–3.05 (m, 2H), 3.32 (d, 1H, J=9.6 Hz), 3.53 (s, 3H), 7.20 (m, 9H); $^{13}$C NMR (CDCl$_3$) d 26.8, 28.9, 33.5, 42.2, 46.5, 51.5, 54.6, 56.1, 57.5, 125.9, 128.3, 128.5, 128.7, 129.3, 132.0, 142.0, 142.6, 172.7; MS m/z 84 (100), 266 (44), 371 (M$^+$, 3); Anal. ($C_{22}H_{26}ClNO_2$) C 71.05, H 7.05, N 3.77; Found: C 70.99, H 6.78, N 3.75.

Example 20

(−)-Methyl 4β-(4-Chlorophenyl)-3β-methyl-1-methylpiperidine-3b-carboxylate (49)

To a solution of i-Pr$_2$NH (0.17 mL, 1.2 mmol) in THF (10 mL) was added dropwise n-BuLi (2.5 M in hexanes, 0.48 mL, 1.2 mmol) at −10° C. After 30 min, the LDA solution was added to a solution of the compound of Example 3 (267 mg, 1.0 mmol) in 10 mL of THF at −78° C. The mixture was stirred at −78° C. for 30 min, and then 75 mL (1.2 mmol) of methyl iodide was added. The solution was stirred at −78° C. for 0.5 h and slowly warmed to room temperature. Next, 10 mL of NH$_4$Cl (sat.) was added, and the resulting mixture was extracted with EtOAc. The organic extracts were washed with brine, dried, and concentrated. Flash chromatography afforded the title compound (50 mg, 18%) in addition to unreacted starting material: $[α]_D$ −49.0 ((c 0.50, CHCl$_3$); IR (film) 835, 1142, 1201, 1492, 1740, 2784, 2970 cm$^{-1}$; $^1$NMR (CDCl$_3$) d 1.13 (s, 3H), 1.60–1.73 (m, 1H), 1.90 (d, 1H, J=11.7 Hz), 2.02 (dt, 1H, J=3.0, 11.7 Hz), 2.27 (s, 3H), 2.34 (dd, 1H, J=3.6, 12.9 Hz), 2.73 (dq, 1H, J=4.2, 12.6 Hz), 2.98–3.06 (m, 1H), 3.16 (dd, 1H, J=1.2, 11.4 Hz), 3.60 (s, 3H), 7.22 (d,2H, J=8.4 Hz), 7.32 (d, 2H, J=8.4 Hz); $^{13}$C NMR (CDCl$_3$) d 23.5, 28.7, 46.5, 47.1, 50.8, 51.4, 56.8, 67.2, 127.6, 131.4, 132.2, 140.0, 174.6; MS m/z 43 (100), 222 (16), 281 (M$^+$, 18); Anal. ($C_{15}H_{20}ClNO_2$) Calcd: C 63.94, H 7.15, N 4.97; Found: C 64.14; H 7.06; N 5.00.

Example 21

(+)-4β-(4-Chlorophenyl)-3α-n-propylpiperidine (50)

To a solution of the compound of Example 15 (158 mg, 0.63 mmol) in dichloromethane (16 mL) were added 1,8-bis-(dimethylamino)naphthalene (proton sponge, 74 mg, 0.43 mmol) and α-chloroethyl chloroformate (0.53 mL, 4.9 mmol). This mixture was heated under reflux for 1.5 h. After cooling to room temperature, 232 mL of 1 M anhydrous hydrogen chloride in ether solution was added, and the mixture was passed through a silica gel plug using CH$_2$Cl$_2$ as the eluent. The combined eluents were concentrated, the residue was taken up in MeOH (14 mL), and the resulting mixture was stirred at reflux for 1 h. After evaporation, 0.5 M KOH was added, the mixture was extracted with EtOAc, and the organic extracts were washed with brine, dried and concentrated. Flash chromatography afforded the title compound (145 mg, 97%): $[α]_D$ +43.4 ((c 0.32, CHCl$_3$); $^1$H NMR (CDCl$_3$) d 0.73 (t, 3H, J=6.9 Hz), 0.82–0.94 (m, 1H), 0.96–1.13 (m, 2H), 1.20–1.35 (m, 1H), 1.60–1.78 (m, 3H), 2.24 (dt, 1H, J=4.2, 11.7 Hz), 2.34 (t, 1H, J=11.1 Hz), 2.54 (s, 1H), 2.69 (dt, 1H, J=2.7, 11.7 Hz), 3.15 (d, 1H, J=12.0 Hz), 3.29 (dd, 1H, J=3.6, 12.0 Hz), 7.10 (d, 2H, J=8.4 Hz), 7.25 (d, 2H, J=8.1 Hz); $^{13}$C NMR (CDCl$_3$) d 14.4, 19.8, 34.0, 36.0, 41.8, 47.2, 49.3, 52.2, 128.7, 129.1, 131.8, 144.1; MS m/z 44 (69), 57 (100), 194 (40), 237 (M$^+$, 29); Anal. ($C_{14}H_{20}ClN$) Calcd: C 70.72, H 8.48, N 5.89; Found: C 70.39, H 8.14, N 6.22.

Example 22

(+)-4β-(4-Chlorophenyl)-3α-n-propylpiperidine Hydrochloride (51)

The hydrochloride salt was made by dissolution of the free base in a methanolic solution of HCl and final trituration of the crude salt with ether: $^1$H NMR (D$_2$O) 0.74 (t, 3H, J=6.3 Hz), 0.96–1.20 (m, 3H), 1.31 (t, 2H, J=6.6 Hz), 1.88–2.14 (m, 3H), 2.52–2.69 (m, 1H), 2.81 (t, 1H, J=12.3 Hz), 3.05–3.33 (m, 2H), 3.40–3.60 (m, 2H), 7.22 (d, 2H, J=8.1 Hz), 7.32 (d, 2H, J=8.1 Hz); C NMR (CD$_3$OD) 14.5, 20.3, 32.3, 34.3, 39.5, 45.6, 47.1, 49.5, 130.0, 130.4, 133.7, 143.2

Example 23

(+)-Methyl (2-E)-3-[4(-(4-Chlorophenyl)-1-methyl-3(-piperidyl]prop-2-enoate (52)

Methyl (triphenylphosphoranylidene)acetate (1.1 g, 3.3 mmol) was added to a solution of 635 mg (2.7 mmol, crude) of the compound of Example 15, sub-part a in 25 mL of toluene under nitrogen at 0° C. The resulting mixture was stirred at room temperature overnight, 50 mL of EtOAc was added, and the resulting solution was washed with NH$_4$Cl. The organic phase was extracted with 10% HCl, and the combined aqueous phases were neutralized with saturated NaHCO$_3$ and extracted with CH$_2$Cl$_2$. The organic extracts were washed with brine, dried, and concentrated. Flash chromatography afforded the desired olefin (466 mg, 54% from 3): $^1$H NMR (CDCl$_3$) d 1.78–1.92 (m, 2H), 1.92–2.15 (m, 2H), 2.25–2.42 (m, 4H), 2.68–2.82 (m, 1H), 2.94–3.05 (m, 2H), 3.63 (s, 3H), 5.60 (d, 1H, J=15.9 Hz), 6.59 (dd, 1H, J=8.4, 15.9 Hz), 7.06 (d, 2H, J=8.1 Hz), 7.23 (d, 2H, J=7.8 Hz); $^{13}$C NMR (CDCl$_3$) d 34.5, 45.3, 46.5, 47.0, 51.7, 56.1, 60.7, 122.2, 128.9, 129.0, 132.4, 142.2, 148.9, 166.8; MS m/z 43 (31), 84 (100), 234 (21), 293 (M$^+$, 7).

Example 24

(+)-Methyl 3-[4(-(4-Chlorophenyl)-1-methyl-3(-piperidyl]propanoate (53)

To a solution of 108 mg (0.37 mmol) of 52 in 2 mL of CH$_3$OH was added 28 mg (1.17 mmol) of magnesium turnings under nitrogen. The resulting solution was stirred at room temperature under nitrogen. After 2 h, all the magnesium had dissolved, and 3 mL of saturated NH$_4$Cl was added. The MeOH was evaporated, the residue was extracted with CH$_2$Cl$_2$, and the organic layer was washed with brine, dried and concentrated to give the crude product (130 mg). This compound was used immediately in the next reaction without further purification: MS m/z 44 (100), 58 (60), 208 (25), 295 (M$^+$, 6).

Example 25

(+)-3-[4(-(4-Chlorophenyl)-1-methyl-3(-piperidyl]propan-1-ol (54)

To a solution of 53 (crude, 130 mg, 0.44 mmol) in 5 mL of THF was added portionwise LiAlH$_4$ (35 mg, 0.88 mmol). The mixture was stirred at room temperature for 2 h, and then a saturated solution of Rochelle salt (3.5 mL) was added followed by extraction with EtOAc. The organic phase was washed with brine, dried, and concentrated. Flash chromatography afforded the product (90 mg, 91% overall yield for the two steps): $[α]_D$ +32.4 ((c 0.5, CHCl$_3$); IR (film) 822, 1058, 1492, 2936, 3387 cm$^{-1}$; $^1$H NMR (CDCl$_3$) d 0.90–1.08 (m, 1H), 1.17–1.40 (m, 3H), 1.44–1.62 (m, 1H), 1.74–2.08 (m, 4H), 2.17 (dt, 2H, J=3.3, 11.1 Hz), 2.45 (s, 3H), 3.09 (d, 1H, J=9.9 Hz), 3.22 (d, 1H, J=11.1 Hz), 3.38–3.55 (m, 2H), 7.13 (d, 2H, J=8.1 Hz), 7.28 (d, 2H, J=8.1 Hz); $^{13}$C NMR (CDCl$_3$) d 27.9, 29.7, 34.2, 40.5, 46.1, 47.9, 56.1, 61.1, 62.8, 128.9, 129.2, 132.3, 142.9; MS m/z 44

(100), 208 (35), 267 (M+, 13); Anal. ($C_{15}H_{22}ClNO$) Calcd: C 67.28, H 8.28, N 5.23; Found: C 67.13, H 8.06, N 5.28.

Example 26

(+)-4β-(4-Chlorophenyl)-3α-(3-fluoropropyl)-1-methylpiperidine (80)

A solution of 26 mg (0.10 mmol) of 54 in 1 mL of $CH_2Cl_2$ was added to a solution of 29.6 mL (0.22 mmol) of diethylaminosulfur trifluoride in 0.5 mL of $CH_2C_2$ at −70° C. The resulting solution was stirred overnight from −70° C. to room temperature, 2 mL of water was added, and the organic layer was dried and concentrated. The residue was purified by flash chromatography to afford the pure compound (16 mg, 61%): $[\alpha]_D$ +34.5 ((c 0.15, $CHCl_3$); IR (film) 822, 1014, 1090, 1143, 1283, 1381, 1493, 2935 $cm^{-1}$; $^1H$ NMR ($CDCl_3$) d 0.96–1.10 (m, 1H), 1.14–1.30 (m, 1H), 1.30–1.50 (m, 1H), 1.75–1.95 (m, 5H), 1.95–2.20 (m, 2H), 2.38 (s, 3H), 2.95 (d, 1H, J=11.4 Hz), 3.07 (d, 1H, J=11.1 Hz), 4.13–4.27 (m, 1H), 4.28–4.40 (m, 1H), 7.10 (d, 2H, J=8.4 Hz), 7.26 (d, 2H, J=8.4 Hz); $^{13}C$ NMR ($CDCl_3$) d 27.5 (d, J=5.5 Hz), 27.8 (d, J=19.7 Hz), 35.1, 41.1, 46.7, 48.4, 56.4, 61.6, 83.2 (d, J=164.5 Hz), 128.9, 129.2, 132.1, 143.5; $^{19}F$ NMR ($CFCl_3$) 135.5–135.9 (m); MS m/z 44 (100), 208 (25), 269 (M+, 14); Anal. ($C_{15}H_{21}ClFN$) Calcd: C 66.78, H 7.85, N 5.19; Found: C 66.10, H 7.88, N 5.20.

Example 27

(+)-3-[4(-(4-Chlorophenyl)-1-methyl-3(-piperidyl]propane-1-thiol (55)

Diisopropyl azodicarboxylate (80 mL, 0.40 mmol) was added to an efficiently stirred solution of triphenylphosphine (105 mg, 0.40 mmol) in 1 mL of THF at 0° C. The mixture was stirred at 0° C. for 30 min during which time a white precipitate formed. A mixture of compound 54 (0.20 mmol, 59 mg) and 28.2 μL (0.4 mmol) of thiolacetic acid in 0.5 mL of THF was added dropwise, and the mixture was stirred at 0° C. for 1 h and then at 25° C. for 2 h. The solution was concentrated. Ether (5 mL) was added, and the ether solution was acidified with 10% HCl. The water layer was extracted with ether and neutralized with saturated $NaHCO_3$. The resulting solution was extracted with $CH_2Cl_2$, and the organic layer was washed with brine, dried, and concentrated to give 50 mg of the crude product. To the solution of the crude thioester (crude, 50 mg, 0.15 mmol) in 5 mL of THF was added portionwise $LiAlH_4$(18 mg, 0.45 mmol). The mixture was stirred at room temperature for 2 h then a saturated solution of Rochelle salt (1.8 mL) was added followed by extraction with EtOAc. The organic phase was washed with brine, dried, and concentrated. Flash chromatography of the residue afforded the title compound (17 mg, 26% overall for the two steps): $[\alpha]_D$ +40.0 ((c 1.40, $CHCl_3$) ;$^1H$ NMR ($CDCl_3$) d 0.92–1.08 (m, 1H), 1.10–1.30 (m, 2H), 1.32–1.64 (m, 2H), 1.64–1.90 (m, 4H), 1.93–2.18 (m, 2H), 2.22–2.50 (m, 5H), 2.95 (d, 1H, J=10.8 Hz), 3.06 (d, 1H, J=10.5 Hz), 7.05–7.15 (m, 2H), 7.20–7.32 (m, 2H); $^{13}C$ NMR ($CDCl_3$) 24.8, 30.7, 31.4, 35.1, 41.0, 46.7, 48.3, 56.4, 61.7, 128.9, 129.2, 132.1, 143.6; MS m/z 44 (26), 250 (100), 282 (M+, 2); Anal. ($C_{15}H_{22}ClNS$) Calcd: C 63.47, H 7.81, N 4.93; Found: C 63.85, H 7.89, N 4.76.

Example 28

(+)-5-[4β-(4-Chlorophenyl)-1-methyl-3(-piperidyl]-3-methyl-1,2,4-oxadiazole (56)

A mixture of NaH (60% suspension, 30 mg) and acetamide oxime (56 mg, 0.75 mmol) in dry THF (10 mL) was stirred at reflux under nitrogen for 1.5 h. The mixture was cooled to room temperature, powdered 4 Å molecular sieves (560 mg) and the compound of Example 11 (100 mg, 0.38 mmol) in 2 mL of THF were added, and the resulting solution was heated under reflux overnight. The solid was removed by filtration and washed with THF. The filtrate and washings were combined and evaporated to dryness, and the residue was purified by flash chromatography to give 80 mg (74%) of the product: $[\alpha]_D$ +98.0° (c 0.58, $CHCl_3$); IR (film) 824, 1092, 1336, 1395, 1494, 1580, 2791, 2940 $cm^{-1}$; $^1H$ NMR ($CDCl_3$) d 1.87–1.96 (m, 2H), 2.14–2.42 (m, 8H), 2.84–2.95 (m, 1H), 3.04 (d, 1H, J=11.4 Hz), 3.16 (dd, 1H, J=2.4, 11.1 Hz), 3.50 (dt, 1H, J=3.9, 11.4 Hz), 7.07 (d, 1H, J=8.7 Hz), 7.20 (d, 1H, J=8.7 Hz); $^{13}C$ NMR ($CDCl_3$) (11.7, 33.9, 42.0, 45.7, 46.3, 55.8, 59.4, 128.8, 129.0, 132.9, 141.0, 167.0, 179.3; MS m/z 43 (80), 96 (73), 204 (100), 233 (23); Anal. ($C_{15}H_{18}ClN_3O$) Calcd: C 61.75, H 6.22, N 14.40; Found: C 61.65, H 6.17, N 14.39.

Example 29

(+)-4β-(4-Chlorophenyl)-1-methylpiperidine-3α-carboxylic Acid (57)

A solution of 840 mg of the compound of Example 11 in 18 mL of 6N HCl was heated under reflux for 6 h then concentrated to afford the hydrochloride salt which was neutralized with saturated $NaHCO_3$ (aq) to afford the free base (800 mg, 98%): $^1H$ NMR ($D_2O$) d 1.97–2.25 (m, 2H), 2.86–3.11 (m, 5H), 3.14–3.24 (m, 1H), 3.68 (d, 1H, J=12.9 Hz), 3.77 (d, 1H, J=12.3 Hz), 7.33 (d, 2H, J=8.7 Hz), 7.45 (d, 1H, J=8.4 Hz).

Example 30

(+)-5-[4β-(4-Chlorophenyl)-1-methyl-3(-piperidyl]-3-phenyl-1,2,4-oxadiazol (58)

To a stirred suspension of 100 mg (0.40 mmol) of 57 in 3 mL of dichloromethane was added dropwise 65 mL (0.75 mmol) of oxalyl chloride. The mixture was stirred for 1.5 h and evaporated to dryness. A solution of benzamidoxime (60 mg, 0.44 mmol) in 4.5 mL of pyridine was added to the acid chloride solution in $CHCl_3$ (1.5 mL) and the mixture was heated under reflux overnight, then evaporated. The residue was dissolved in 4 mL of HOAc. The mixture was stirred at reflux for 4 h, and concentrated. Flash chromatography gave the product (20 mg, 14%): $[\alpha]_D$ +147.0° (c 0.28, $CHCl_3$); IR (film) 701, 1070, 1360, 1445, 1568, 1594, 2790, 2939 $cm^{-1}$; $^1H$ NMR ($CDCl_3$) d 1.90–2.01 (m, 2H), 2.18–2.29 (m, 1H), 2.36–2.48 (m, 4H), 2.98–3.12 (m, 2H), 3.22 (dd, 1H, J=2.7, 11.4 Hz), 3.58 (dt, 1H, J=3.9, 11.7 Hz), 7.12 (d, 2H, J=8.7 Hz), 7.20 (d, 2H, J=8.4 Hz), 7.39–7.51 (m, 3H), 7.93–8.03 (m, 2H); $^{13}C$ NMR ($CDCl_3$) d 33.8, 42.2, 45.6, 46.3, 55.8, 59.5, 126.9, 127.6, 128.8, 128.98, 129.0, 131.3, 132.9, 141.0, 168.2, 179.5; MS m/z 44 (100), 204 (30), 233 (9).

Example 31

(+)-Phenyl 4β-(4-Chlorophenyl)-1-methylpiperidine-3α-carboxylate (59)

To a solution of 62 mg (0.22 mmol) of acid chloride which was made from 57 in 3 mL of dichloromethane was added 13.8 mg (0.15 mmol) of phenol, a little bit of pyridine and catalytic amount of DMAP. The resulting mixture was stirred at room temperature overnight and evaporated. Flash chromatography afforded the product (20 mg, 28%): $[\alpha]_D$ +72.0 ((c 1.02, $CHCl_3$); IR (film) 821, 1123, 1195, 1493, 1754, 2791, 2938 cm$^{-1}$; $^1$H NMR (CDCl$_3$) d 1.86–1.96 (m, 2H), 2.14–2.24 (m, 1H), 2.36 (t, 1H, J=11.7 Hz), 2.43 (s, 3H), 2.81–2.94 (m, 1H), 3.02 (d, 1H, J=11.1 Hz), 3.13 (dt, 1H, J=3.6, 11.1 Hz), 3.29 (dd, 1H, J=2.1, 11.1 Hz), 6.67 (d, 2H, J=7.8 Hz), 7.18 (t, 1H, J=7.8 Hz), 7.23–7.37 (m, 6H); $^{13}$C NMR (CDCl$_3$) d 33.4, 44.7, 46.4, 49.4, 55.9, 58.1, 121.5, 126.0, 129.0, 129.2, 129.5, 132.8, 141.8, 150.4, 171.8; MS m/z 42 (27), 70 (100), 208 (33), 236 (38), 329 (M$^+$, 7); Anal. (C$_{19}$H$_{20}$ClNO$_2$) Calcd: C 69.19, H 6.11, N 4.25; Found: C 69.20, H 5.86, N 4.20.

Example 32

(−)-Phenyl 4β-(4-Chlorophenyl)-1-methylpiperidine-3b-carboxylate (60)

A solution of 213 mg of the compound of Example 3 in 6 mL of 6 N HCl was heated under reflux for 6 h then concentrated to afford the hydrochloride salt which was neutralized with saturated NaHCO$_3$ (aq) to afford the free base: 180 mg. To a solution of 79 mg (0.31 mmol) of this acid in 3 mL of CH$_2$Cl$_2$ was added 54 mL (0.62 mmol) of oxalyl chloride at 0° C., the resulting solution was stirred at room temperature for 1 h then dried in vacuo. To the acid chloride in 3 mL of dichloromethane were added 57 mg (0.31 mmol) of phenol, a little bit of pyridine and catalytic amount of DMAP. The resulting mixture was stirred at room temperature overnight and evaporated. Flash chromatography afforded the product (30 mg, 30%): [α]$_D$ −60.0 ((c 0.98, CHCl$_3$); IR (film) 745, 1198, 1493, 1765, 2786, 2941 cm$^{-1}$; $^1$H NMR (CDCl$_3$) d 1.84 (dd, 1H, J=3.3, 12.9 Hz), 2.14 (dt, 1H, J=3.0, 11.1 Hz), 2.36 (s, 3H), 2.50 (dd, 1H, J=3.6, 11.7 Hz), 2.67 (dq, 1H, J=3.9, 11.7 Hz), 2.86–3.04 (m, (2H), 3.22 (d, 1H, J=3.6 Hz), 3.37 (dd, 1H, J=2.1, 11.4 Hz), 6.84 (d, 2H, J=7.5 Hz), 7.14 (t, 1H, J=7.5 Hz), 7.24–7.32 (m, 6H); $^{13}$C NMR (CDCl$_3$) d 26.8, 41.5, 46.6, 46.8, 56.0, 58.6, 121.8, 125.8, 128.5, 129.4, 129.5, 132.3, 141.5, 150.7, 170.9; MS m/z 44 (27), 70 (100), 236 (42), 329 (M$^+$, 6).

Example 33

(+)-1-[4(-(4-Chlorophenyl)-1-methyl-3(-piperidyl]propan-1-one (61)

To a stirred suspension of 150 mg (0.52 mmol) of the hydrochloride salt of 57 in 5 mL of dichloromethane was added dropwise 0.1 mL (1.15 mmol) of oxalyl chloride. The mixture was stirred for 2 h and evaporated to dryness. Then to the solution of Et$_2$Zn (2 mL, 1.0 M in hexane) and catalytic amount of Pd(PPh$_3$)$_4$ in 5 mL of THF was added the acid chloride in 10 mL of THF at 0 (C. the resulting solution was stirred at 0 (C for 2 h and stirred at room temperature overnight. The reaction was quenched by adding 10 mL of 10% HCl when cooled with an ice bath. The aqueous layer was extracted with EtOAc one time and was neutralized with NaHCO$_3$ (sat.), then extracted with CH$_2$Cl$_2$. The organic extracts were washed with brine, dried and concentrated. Flash chromatograph gave the product (30 mg, 22%): [α]$_D$ +52.0 ((c 0.45, CHCl$_3$); IR (film) 822, 1014, 1492, 1711, 2790, 2937 cm$^{-1}$; $^1$H NMR (CDCl$_3$) d 0.77 (t, 3H, J=7.2 Hz), 1.76–1.98 (m, 4H), 2.01–2.15 (m, 2H), 2.21–2.40 (m, 4H), 2.75 (dt, 1H, J=5.4, 11.4 Hz), 2.90–3.00 (m, 2H), 3.05 (dt, 1H, J=3.6, 11.1 Hz), 7.11 (d, 2H), J=8.7 Hz), 7.24 (d, 2H, J=8.4 Hz); $^{13}$C NMR (CDCl$_3$) d 7.3, 33.1, 37.6, 44.1, 46.4, 55.7, 55.9, 58.1, 128.9, 129.0, 132.5, 142.2, 212.3; MS m/z 43 (23), 98 (100), 236 (1), 265 (M$^+$, 6).

Example 34

(+)-Methyl 4β-(4-Bromophenyl)-1-methylpiperidine-3β-carboxylate (62)

To a solution of 3.5 g (145 mmol) of Mg in 11 mL of dry ether was added a little bit of I$_2$ and about 10 mL of the solution of 34.1 g (145 mmol) of p-dibromobenzene in 200 mL of ether. The mixture was stirred until the color of I$_2$ disappeared. Then the reminder was added at the rate that the reaction went vigorously. Then the resulting solution was stirred at room temperature until all the Mg disappeared. Another 300 mL of dry ether was added to the Grignard reagent solution and it was cooled to −15° C., the arecoline (11.7 g, 75.5 mmol) in 250 mL of dry ether was added dropwise to it. The resulting mixture was stirred at −15° C. for another 0.5 h. then treated slowly with 10% HCl (200 mL) at −40° C. The aqueous layer was separated, extracted with ether (200 mL), and then basified with a saturated solution of sodium bicarbonate when cooled in an ice bath. The mixture was extracted with ether and the combined organic extracts were washed with brine, dried and concentrated under reduced pressure. Flash chromatography (ether/Et$_3$N, 10:1) and then recrystalization afforded the cis isomer 62 (5.2 g, 22%) as a white solid: IR (KBr) 774, 843, 1008, 1175, 1244, 1380, 1488, 1732, 2788, 2957 cm$^{-1}$; $^1$H NMR (CDCl$_3$) d 1.74–1.86 (m, 1H), 2.07 (dt, 1H, J=3.0, 11.1 Hz), 2.28 (s, 3H), 2.35 (dd, 1H, J=3.6, 11.4 Hz), 2.58–2.82 (m, 2H), 2.92–3.04 (m, 2H), 3.18 (d, 1H, J=11.7 Hz), 3.52 (s, 3H), 7.17 (d, 1H, J=8.4 Hz), 7.40 (d, 1H, J=8.1 Hz); $^{13}$C NMR (CDCl$_3$) d 26.7, 41.6, 46.3, 46.8, 51.6, 56.2, 58.7, 120.2, 129.7, 131.3, 142.4, 172.8; MS m/z 44 (100), 252 (20), 311 (M$^+$-1, 11).

Example 35

(−)-Methyl 4β-(4-Bromophenyl)-1-methylpiperidine-3β-carboxylate (63)

To a solution of 62 (4.3 g, 13.7 mmol) in 70 mL of MeOH was added a solution of dibenzoyl-L-tartaric acid (5.2 g, 13.7 mmol) in MeOH (35 mL). The resulting mixture was stirred at room temperature for 5 h. After filtration, the white precipitate was washed with MeOH (5 mL). This tartrate salt was treated with a saturated solution of NaHCO$_3$ (50 mL) and extracted with CHCl$_3$ (3×50 mL). The combined organic extracts were washed with brine, dried and concentrated under reduced pressure to afford the title compound (1.6 g) as a white solid: mp 121–122° C.; [α]$_D$ −24.7 ((c 0.53, CHCl$_3$); IR (KBr) 774, 843, 1018, 1180, 1244, 1380, 1489, 1729, 2786, 2955 cm$^{-1}$; $^1$H NMR (CDCl$_3$) d 1.74–1.86 (m, 1H), 2.07 (dt, 1H, J=3.0, 11.1 Hz), 2.28 (s, 3H), 2.35 (dd, 1H, J=3.6, 11.4 Hz), 2.58–2.82 (m, 2H), 2.92–3.04 (m, 2H), 3.18 (d, 1H, J=11.7 Hz), 3.52 (s, 3H), 7.17 (d, 1H, J=8.4 Hz), 7.40 (d, 1H, J=8.1 Hz); $^{13}$C NMR (CDCl$_3$) d 26.7, 41.6, 46.3, 46.8, 51.6, 56.2, 58.7, 120.2, 129.7, 131.3, 142.4, 172.8; MS m/z 44 (100), 252 (13), 311 (M$^+$-1, 6); Anal. (C$_{14}$H$_{18}$BrNO$_2$) Calcd: C 53.86, H 5.81, N 4.49; Found: C 54.15, H 5.52, N 4.61.

Example 36

(−)-Methyl 4β-(4-Vinylphenyl)-1-methylpiperidine-3β-carboxylate (64)

To a solution of 223 mg (0.72 mmol) of 63 in 7 mL of dioxane was added a few crystals of 4-tert-butylcatechol, 18 mg of triphenylphosphine, 0.24 mL (0.80 mmol) of vinyl-tributyltin and 30 mg (0.026 mmol) of Pd(PPh$_3$)$_4$. The mixture was heated under reflux for 6 h and was cooled to room temperature then 2 mL of 1 M Py-HF solution was added. The resulting solution was stirred at room temperature for 16 h and was diluted with ether, filtered through a small pad of Celite. The filtrate was washed with NH$_4$Cl (sat.), water and brine, dried and concentrated. Flash chromatography gave the product (100 mg, 54%): mp 68–69° C.;

[α]$_D$ −27.6 ((c 0.46, CHCl$_3$); IR (KBr) 850, 1016, 1165, 1241, 1629, 1745, 2783, 2942 cm$^{-1}$; $^1$H NMR (CDCl$_3$) d 1.78–1.88 (m, 1H), 2.09 (dt, 1H, J=2.7, 11.1 Hz), 2.29 (s, 3H), 2.37 (dd, 1H, J=3.3, 11.4 Hz), 2.68 (dq, 1H, J=3.6, 12.0 Hz), 2.78–2.87 (m, 1H), 2.93–3.02 (m, 2H), 3.18 (dd, 1H, J=1.5, 11.1 Hz), 3.52 (s, 3H), 5.20 (d, 1H, J=10.8 Hz), 5.71 (d, 1H, J=17.4 Hz), 6.68 (dd, J=10.8, 17.4 Hz), 7.25 (d, 2H, J=8.1 Hz), 7.34 (d, 2H, J=8.1 Hz); $^{13}$C NMR (CDCl$_3$) d 26.9, 41.8, 46.4, 46.9, 51.5, 56.2, 58.6, 113.4, 126.2, 128.0, 135.7, 136.8, 143.0, 172.9; MS m/z 44 (100), 200 (16), 259 (M$^+$, 14); Anal. (C$_{16}$H$_{21}$NO$_2$) Calcd: C 74.10, H 8.16, N 5.40; Found: C 73.81, H 8.20, N 5.37.

Example 37

(+)-Methyl 4β-(4-Vinylphenyl)-1-methylpiperidine-3α-carboxylate (65)

To a solution of 64 (15 mg) in 2 mL of MeOH was added a little bit of 30% methanolic solution of sodium methoxide. The resulting solution was stirred at reflux overnight and concentrated under pressure, CH$_2$Cl$_2$ and NH$_4$Cl were added and the organic layer was washed with brine, dried and concentrated. Flash chromatography gave the product (10 mg, 67%): [α]$_D$ +62.6 ((c 0.50, CHCl$_3$); IR (film) 837, 908, 1159, 1629, 1736, 2787, 2940 cm$^{-1}$; $^1$H NMR (CDCl$_3$) d 1.78–1.90 (m, 2H), 2.05–2.13 (m, 1H), 2.18 (t, 1H, J=11.1 Hz), 2.35 (s, 3H), 2.50–2.83 (m, 1H), 2.93 (dt, 2H, J=3.9, 11.1 Hz), 3.10 (dd, 1H, J=2.1, 11.1 Hz), 3.43 (s, 3H), 5.20 (d, 1H, J=10.8 Hz), 5.71 (d, 1H, J=17.4 Hz), 6.68 (dd, 1H, J=10.8, 17.4 Hz), 7.16 (d, 2H, J=8.4 Hz), 7.32 (d, 2H, J=8.1 Hz); $^{13}$C NMR (CDCl$_3$) 33.3, 44.5, 46.4, 49.3, 51.7, 56.0, 58.4, 113.5, 126.6, 127.7, 136.2, 136.8, 143.3, 173.8; MS m/z 44 (100), 200 (31), 259 (M$^+$, 25).

Example 38

(−)-Methyl 4β-(4-Ethylphenyl)-1-methylpiperidine-3β-carboxylate (81)

A solution of 200 mg of 64 in 10 mL of methanol and 20 mg of 10% Pd/C was stirred at room temperature and 1 atm of H$_2$ for two hours. The mixture was filtered through a short Celite pad and concentrated to afford the product (195 mg, 97%): [α]$_D$ −26.3 ((c 0.48, CHCl$_3$); IR (film) 778, 843, 1017, 1164, 1241, 1379, 1515, 1746, 2782, 2963 cm$^{-1}$; $^1$H NMR (CDCl$_3$) d 1.21 (t, 3H, J=7.5 Hz), 1.76–1.87 (m, 1H), 2.08 (dt, 1H, J=2.7, 11.1 Hz), 2.28 (s, 3H), 2.37 (dd, 1H, J=3.6, 11.7 Hz), 2.61 (q, 2H, J=7.5 Hz), 2.64–2.75 (m, 1H), 2.76–2.86 (m, 1H), 2.92–3.04 (m, 2H), 3.16 (d, 1H, J=11.4 Hz), 3.52 (s, 3H), 7.11 (d, 2H, J=8.1 Hz), 7.21 (d, 2H, J=8.1 Hz); $^{13}$C NMR (CDCl$_3$) d 15.6, 27.0, 28.5, 41.6, 46.4, 46.8, 51.3, 56.2, 58.5, 127.7, 140.4, 142.1, 173.0; MS m/z 44 (75), 70 (100), 202 (25), 261 (M$^-$, 22).

Example 39

(−)-Methyl 4β-(4-Ethyl-3-iodophenyl)-1-methylpiperidine-3β-carboxylate (66)

To a stirred slurry of 295 mg (1.36 mmol) of mercuric oxide in 2.3 mL of glacial acetic acid was added 0.7 mL of perchloric acid. The slurry was stirred until all of the orange solid dissolved. To this stirred solution was added 177 mg (0.68 mmol) of 81 as a solution in 1.5 mL of acetic acid. After 15 min, a solution of 433 mg (1.7 mmol) of iodine in 1.5 mL of acetic acid with a small amount of methylene chloride was introduced dropwise and the resulting slurry was stirred for 3 h. The yellow and red solids were then filtered through a plug of Celite and the acetic acid was neutralized by cooling the solution to 0° C. and adding concentrated ammonium hydroxide dropwise. The mixture was extracted with methylene chloride. The combined extracts were dried over sodium sulfate and concentrated. The resulting oil was purified by flash chromatography on silica gel to afford 150 mg (57%) of the title compound: [α]$_D$ −28.0 ((c 0.39, CHCl$_3$); IR (film): 1166, 1240, 1378, 1463, 1743, 2784, 2964 cm$^{-1}$; $^1$H NMR (CDCl$_3$) d 1.18 (t, 3H, J=7.5 Hz), 1.73–1.85 (m, 1H), 2.07 (dt, 1H, J=2.7, 11.1 Hz), 2.28 (s, 3H), 2.34 (dd, 1H, J=3.3, 11.4 Hz), 2.54–2.80 (m, 4H), 2.92–3.02 (m, 2H), 3.18 (d, 1H, J=10.2 Hz), 3.55 (s, 3H), 7.11 (d, 1H, J=7.8 Hz), 7.21 (d, 1H, J=7.8 Hz), 7.70 (d, 1H, J=1.2 Hz); $^{13}$C NMR (CDCl$_3$) d 14.7, 26.8, 33.8, 41.2, 46.3, 46.8, 51.5, 56.2, 58.6, 100.5, 127.8, 128.2, 138.8, 142.9, 144.4, 172.8; MS m/z 44 (80), 70 (100), 328 (17), 387 (M$^-$, 14); Anal. (C$_{16}$H$_{22}$INO$_2$) Calcd: C 49.62, H 5.73, N 3.62; Found: C.49.62, H 5.43, N 3.50.

Example 40

(+)-Methyl 4β-(4-Ethylphenyl)-1-methylpiperidine-3α-carboxylate (67)

To a solution of 81 (163 mg) in 4 mL of MeOH was added 30% methanolic solution of sodium methoxide (40 mL). The resulting solution was stirred at reflux overnight and was concentrated under reduced pressure, CH$_2$Cl$_2$ and NH$_4$Cl were added and the organic layer was washed with brine, dried and concentrated. Flash chromatography gave the product (140 mg, 86%): [α]$_D$ +62.4 ((c 0.42, CHCl$_3$); IR (film) 827, 1158, 1379, 1737, 2787, 2938 cm$^{-1}$; $^1$H NMR (CDCl$_3$) d 1.21 (t, 3H, J=7.5 Hz), 1.78–1.89 (m, 2H), 2.05–2.16 (m, 1H), 2.18 (t, 1H, J=11.1 Hz), 2.35 (s, 3H), 2.61 (q, 2H, J=7.5 Hz), 2.68–2.80 (m, 1H), 2.85–3.00 (m, 2H), 3.04–3.13 (m, 1H), 3.41 (s, 3H), 7.03–7.16 (m, 4H); $^{13}$C NMR (CDCl$_3$) d 15.6, 28.6, 33.4, 44.3, 46.3, 49.5, 51.6, 56.1, 58.5, 127.3, 128.1, 140.7, 142.6, 173.9; MS m/z 44 (59), 70 (100), 202 (34), 261 (M$^+$, 25).

Example 41

(+)-Methyl 4β-(4-Ethyl-3-iodophenyl)-1-methylpiperidine-3α-carboxylate (68)

To a stirred slurry of 39 mg (0.18 mmol) of mercuric oxide in 0.3 mL of glacial acetic acid was added 0.093 mL of perchloric acid. The slurry was stirred until all of the orange solid dissolved. To this stirred solution was added 23 mg (0.09 mmol) of 67 as a solution in 0.2 mL of acetic acid. After 15 min, a solution of 57.3 mg (0.23 mmol) of iodine in 0.2 mL of acetic acid with a small amount of methylene chloride was introduced dropwise and the resulting slurry was stirred for 3 h. The yellow and red solids were then filtered through a plug of Celite and the acetic acid was neutralized by cooling the solution to 0° C. and adding concentrated ammonium hydroxide dropwise. The mixture was extracted with methylene chloride. The combined extracts were dried over sodium sulfate and concentrated. The resulting oil was purified by flash chromatography on silica gel to afford 15 mg (51%) of the title compound: [α]$_D$ +32.2 ((c 0.27, CHCl$_3$); IR (film) 828, 1160, 1737, 2787, 2938 cm$^{-1}$; $^1$H NMR (CDCl$_3$) d 1.18 (t, 3H, J=7.5 Hz), 1.75–1.85 (m, 2H), 2.03–2.12 (m, 1H), 2.16 (t, 1H, J=10.8 Hz), 2.35 (s, 3H), 2.67 (q, 3H, J=7.5 Hz), 2.82–2.98 (m, 2H), 3.09 (dd, 1H, J=2.4, 11.1 Hz), 3.45 (s, 3H), 7.12 (s, 2H), 7.65 (s, 1H); $^{13}$C NMR (CDCl$_3$) d 14.7, 33.3, 33.9 43.6, 46.3, 49.2, 51.8, 55.9, 58.3, 100.7, 127.4, 128.6, 138.5, 143.1, 144.9, 173.6; MS m/z 44 (59), 70 (100), 328 (11), 387 (M$^+$, 10).

Example 42

(+)-Methyl 4β-(4-Bromophenyl)-1-methylpiperidine-3β-carboxylate (69)

To a solution of the free base of the residue of 63 (6.1 g, 19.5 mmol) in 110 mL of MeOH was added a solution of dibenzoyl-L-tartaric acid (7.4 g, 19.5 mmol) in MeOH (55 mL). The resulting mixture was stirred at room temperature for 5 h. After filtration, the white precipitate was washed with MeOH (10 mL). This tartrate salt was treated with a saturated solution of NaHCO$_3$ (50 mL) and extracted with CHCl$_3$ (3×50 mL). The combined organic phase was washed with brine, dried and concentrated to afford the title compound (3.45 g) as a white solid: mp 125–126° C.; [α]$_D$ +23.3 ((c 0.92, CHCl$_3$); IR (KBr) 774, 843, 1180, 1244, 1380, 1489, 1729, 2786, 2934 cm$^{-1}$; $^1$H NMR (CDCl$_3$) d 1.74–1.86 (m, 1H), 2.07 (dt, 1H, J=2.7, 11.1 Hz), 2.28 (s, 3H), 2.35 (dd, 1H, J=3.6, 11.4 Hz), 2.58–2.82 (m, 2H), 2.92–3.04 (m, 2H), 3.18 (d, 1H, J=11.7 Hz), 3.52 (s, 3H), 7.17 (d, 2H, J=8.4 Hz), 7.40 (d, 2H, J=8.4 Hz); $^{13}$C NMR (CDCl$_3$) d 26.7, 41.7, 46.3, 46.8, 51.6, 56.2, 58.7, 120.2, 129.7, 131.3, 142.4, 172.8; MS m/z 44 (100), 70 (74), 252 (29), 311 (M$^-$, 14).

Example 43

(−)-Methyl 4β-(4-bromophenyl)-1-methylpiperidine-3α-carboxylate (70)

To a solution of 69 (43 mg) in 3 mL of MeOH was added 50 mL of 30% methanolic solution of sodium methoxide. The resulting solution was stirred at reflux overnight and concentrated, CH$_2$Cl$_2$ and NH$_4$Cl were added and the organic layer was washed with brine, dried and concentrated. Flash chromatography gave the product (40 mg, 93%): [α]$_D$ −44.0 ((c 1.34, CHCl$_3$); IR (film) 818, 1010, 1160, 1491, 1735, 2787, 2941 cm$^{-1}$; $^1$H NMR (CDCl$_3$) d 1.76–1.86 (m, 2H), 2.04–2.13 (m, 1H), 2.18 (t, 1H, J=11.1 Hz), 2.35 (s, 3H), 2.68–2.80 (m, 1H), 2.84–3.00 (m, 2H), 3.10 (dd, 1H, J=2.4, 11.1 Hz), 3.43 (s, 3H), 7.08 (d, 2H, J=8.1 Hz), 7.40 (d, 2H, J=8.1 Hz); $^{13}$C NMR (CDCl$_3$) d 33.3, 44.2, 46.3, 49.1, 51.8, 55.9, 58.3, 120.6, 129.3, 131.8, 142.6, 173.5; MS m/z 43 (100), 70 (61), 252 (28), 313 (M$^-$+1, 16).

Example 44

(+)-Methyl 4β-(4-Bromophenyl)-1-methylpiperidine-3α-carboxylate (71)

To a solution of 63 (34 mg) in 2 mL of MeOH was added 50 mL of 30% methanolic solution of sodium methoxide. The resulting solution was stirred at reflux overnight. The solution was concentrated under reduced pressure, CH$_2$Cl$_2$ and NH$_4$Cl were added and the organic layer was washed with brine, dried and concentrated. Flash chromatography gave the product (22 mg, 65%): [α]$_D$ +45.6 ((c 1.00, CHCl$_3$); IR (film) 819, 1010, 1160, 1491, 1734, 2788, 2941 cm$^{-1}$; $^1$H NMR (CDCl$_3$) d 1.76–1.86 (m, 2H), 2.04–2.13 (m, 1H), 2.17 (t, 1H, J=10.8 Hz), 2.35 (s, 3H), 2.68–2.80 (m, 1H), 2.84–3.00 (m, 2H), 3.10 (dd, 1H, J=2.1, 10.8 Hz), 3.43 (s, 3H), 7.08 (d, 2H, J=8.4 Hz), 7.40 (d, 2H, J=8.1 Hz); $^{13}$C NMR (CDCl$_3$) d 33.3, 44.2, 46.3, 49.2, 51.8, 55.9, 58.3, 120.6, 129.3, 131.8, 142.6, 173.5; MS m/z 43 (100), 70 (88), 252 (28), 311 (M$^+$−1, 17).

Example 45

(−)-1-Methyl-3-hydroxymethyl-4-phenylpiperidine (72)

To the solution of the compound of Example 3 (63 mg, 0.24 mmol) in 5 mL of THF was added portion wisely LiAlH$_4$ (25 mg, 0.63 mmol). The mixture was stirred at reflux overnight then a saturated solution of Rochelle salt (2.5 mL) was added followed by extraction with EtOAc. The organic phase was washed with brine, dried and concentrated. Flash chromatography afforded the product (30 mg): [α]$_D$ −62.0 ((c 0.89, CHCl$_3$).

Example 46

(−)-1-Methyl-3-hydroxymethyl-4-phenylpiperidine (72)

To the solution of 63 (37 mg, 0.12 mmol) in 5 mL of THF was added portionwisely LiAlH$_4$ (15 mg, 0.36 mmol). The mixture was stirred at reflux overnight then a saturated solution of Rochelle salt (1.5 mL) was added followed by extraction with EtOAc. The organic phase was washed with brine, dried and concentrated. Flash chromatography afforded the product (25 mg): [α]$_D$ −63.0 ((c 0.63, CHCl$_3$).

Example 47

(±)-Methyl 4β-(1-Naphthyl)-1-methylpiperidine-3β-carboxylate (73)

To a solution of 480 mg (20.0 mmol) of Mg in 20 mL of dry ether was added a little bit of 12 and several drops of a-bromonaphthalene (about 0.5 mL, 3.6 mmol). the mixture was heated until the color of I$_{12}$ disappeared. Then the other 2.3 mL (16.4 mmol) of 1-bromonaphthalene in 20 mL of ether was added at the rate that the reaction went vigorously. Then the resulting solution was refluxed until all the Mg disappeared. Another 30 mL of dry ether was added to the Grignard reagent solution and it was cooled to −15° C., the arecoline (1.5 g, 9.7 mmol) in 20 mL of dry ether was added dropwise to it. The resulting mixture was stirred at −15° C. for another one hour. then poured onto cracked ice and treated slowly with 10% HCl (22 mL). The aqueous layer was separated, extracted with ether (20 mL), and then basified with saturated sodium bicarbonate solution when cooled in an ice bath. The mixture was extracted with ether and the combined organic phase was washed with brine, dried and concentrated. Flash chromatography afforded the cis isomer 73 (700 mg, 26%) as a white solid: mp 108–109° C.; IR (KBr) 776, 1157, 1379, 1747, 2792, 2931 cm$^{-1}$; $^1$H NMR (CDCl$_3$) d 1.78–1.87(m, 1H), 2.21 (dt, 1H, J=2.7, 11.1 Hz), 2.35 (s, 3H), 2.54 (dd, 1H, J=3.3, 11.1 Hz), 2.92–3.18 (m, 2H), 3.18–3.32 (m, 2H), 3.41 (s, 3H), 3.51–3.63 (m, 1H), 7.40–7.56 (m, 3H), 7.61 (d, 1H, J=6.9 Hz), 7.72 (d, 1H, J=8.1 Hz), 7.86 (dd, 1H, J=1.5, 7.2 Hz), 7.97 (d, 1H, J=8.4 Hz); $^{13}$C NMR (CDCl$_3$) d 22.5, 33.7, 40.6, 42.2, 46.6, 52.2, 54.3, 118.0, 120.6, 120.9, 121.0, 121.4, 122.5, 124.8, 126.8, 129.3, 133.5, 168.1; MS m/z 44 (83), 70 (100), 283 (M$^+$, 44); Anal. (C$_{18}$H$_{21}$NO$_2$) Calcd: C 76.30, H 7.47, N 4.94; Found: C 76.24; H 7.31; N 4.94.

Example 48

(±)-Methyl 4β-(2-Naphthyl)-1-methylpiperidine-3β-carboxylate (74)

A solution of 2-bromonaphthalene (2.07 g, 10 mmol) was added to 240 mg (10 mmol) of Mg and 1,2-dibromoethane (140 mg, 0.75 mmol) in 3 mL of dry ether with stirring and heating under reflux. The resulting solution was heated under reflux until all the Mg disappeared. Another 10 mL of dry ether was added to the Grignard reagent solution and it was cooled to −20° C., the arecoline (630 mg, 4.1 mmol) in 15 mL of dry ether was added dropwise to it. The resulting mixture was stirred at −15° C. for another 0.5 hour. The mixture was cooled to about −40° C. and treated slowly with 10% HCl (15 mL). The aqueous layer was separated, extracted with ether (20 mL), and then basified with saturated sodium bicarbonate solution when cooled in an ice bath. The mixture was extracted with ether and the combined organic phase was washed with brine, dried and concentrated under reduced pressure. Flash chromatography afforded the cis isomer 74 (259 mg, 20%): mp 100–101° C.; IR (KBr) 758, 1019, 1165, 1743, 2783, 2941 cm$^{-1}$; $^1$H NMR (CDCl$_3$) d 1.92 (dd, 1H, J=3.0, 12.6 Hz), 2.11 (dt, 1H, J=2.7, 11.1 Hz), 2.30 (s, 3H), 2.41 (dd, 1H, J=3.6, 11.4Hz), 2.81 (dq, 1H,J=3.6 11.7 Hz), 2.96–3.08 (m, 2H), 3.12 (d, 1H, J=3.3 Hz), 3.23 (dd, 1H, J=1.8, 11.4 Hz), 3.45 (s, 3H), 7.38–7.48 (m, 3H), 7.70–7.83 (m, 4H); $^{13}$C NMR (CDCl$_3$) d 22.3, 37.4, 41.7, 42.1, 4.68 51.4, 53.9, 120.9, 121.3, 121.6, 121.9, 123.0, 123.1, 123.4, 127.6, 128.8, 136.0, 168.2; MS m/z 44 (63), 70 (100), 252 (2), 283 (M$^+$, 16); Anal. (C$_{18}$H$_{21}$NO$_2$) Calcd: 4.94; Found: C 76.41, H 7.40, N 5.03.

Example 49

(±)-Methyl 4-(2-Naphthyl)-1-methylpiperidine-3-carboxylate (75)

The chromatography column from Example 48 was further eluted to give 224 mg of a mixture of trans isomer 75 and starting material. This material was separated by column with 90:10:5 of hexane/EtOAc/Et$_3$N as the eluent to give the title compound: IR (film) 746, 819, 1194, 1733, 2789, 2939 cm$^{-1}$; $^1$H NMR (CDCl$_3$) d 1.85–2.10 (m, 2H), 2.18 (dt, 1H, J=3.3, 11.1 Hz), 2.26 (t, 1H, J=10.5 Hz), 2.40 (s, 3H), 2.90–3.20 (m, 4H), 3.38 (s, 3H), 7.36–7.48 (m, 3H), 7.65 (s, 1H), 7.74–7.82 (m, 3H); $^{13}$C NMR (CDCl$_3$) d 33.4, 44.9, 46.4, 49.2, 51.7, 56.1, 58.4, 125.6, 125.9, 126.1, 127.8, 127.9, 128.3, 132.7, 133.7, 141.1, 173.8; MS m/z 44 (33), 70 (100), 224 (8), 283 (M$^-$, 12).

Example 50

(±)-Methyl 4-Benzyl-1-methylpiperidine-3-carboxylate (76,77)

To a solution of 480 mg of Mg in 2 mL of dry ether was added a little bit of I$_2$ and several drops of benzyl chloride (about 0.5 mL) of the solution of 2.3 mL (20 mmol) of benzyl chloride in 10 mL of ether. The mixture was gentle stirred, as soon as the reaction sets in, the reminder of benzyl chloride in ether was added at the rate that the reaction went vigorously by cooling the flask with water. Then the resulting solution was stirred at gentle reflux for fifteen minutes after all the benzyl chloride has been added. Another 5 mL of dry ether was added to the Grignard reagent solution and it was cooled to −15° C., the arecoline (1.5 g) in 20 mL of dry ether was added dropwise to it. The resulting mixture was stirred at −15° C. for another 0.5 hour. The mixture was cooled to about −40° C. and treated slowly with 10% HCl (22 mL). The aqueous layer was separated, extracted with ether (20 mL), and then basified with saturated sodium bicarbonate solution when cooled in an ice bath. The mixture was extracted with ether and the combined organic extracts were washed with brine, dried and concentrated under reduced pressure. Flash chromatography afforded a mixture of cis isomer 76 and trans isomer 77 (500 mg, 21%).

Example 51

(±)-Methyl 4β-Benzyl-1-methylpiperidine-3α-carboxylate (77)

To a solution of the mixture of 76 and 77 from Example 50 (90 mg) in 2 mL of MeOH was added 30% methanolic solution of sodium methoxide (50 mL). The resulting solution was stirred at reflux overnight and concentrated, CH$_2$Cl$_2$ and NH$_4$Cl were added and the organic layer was washed with brine, dried and concentrated. Flash chromatography gave the product (72 mg, 80%): IR (film) 701, 747, 1156, 1734, 2787, 2938 cm$^{-1}$; $^1$H NMR (CDCl$_3$) d 1.26 (dq, 1H, J=3.9, 12.0 Hz), 1.59 (dq, 1H, J=3.3, 13.2 Hz), 1.79–1.95 (m, 2H) 2.07 (t, 1H, J=11.1 Hz), 2.22–2.35 (m, 4H), 2.49 (dt, 1H, J=3.9, 11.7 Hz), 2.70–2.84 (m, 2H), 2.96 (dd, 1H, J=2.1, 10.8 Hz), 3.65 (s, 3H), 7.10–7.30 (m, 5H); $^{13}$C NMR (CDCl$_3$) d 30.1, 39.0, 40.9, 46.3, 48.9, 51.8, 55.5, 58.2, 126.2, 128.4, 129.5, 139.8, 174.7; MS m/z 44 (100), 91 (41), 232 (5), 247 (M$^+$, 20); Anal. (C$_{15}$H$_{21}$NO$_2$) Calcd: C 72.84, H 8.56, N 5.66; found: C 72.22, H 8.29, N 6.17.

Example 52

(±)-Methyl 4β-(2-Furyl)-1-methylpiperidine-3α-carboxylate (78)

To a solution of 0.91 mL (12.5 mmol) of furan was added dropwise 6 mL of 2.5 M of n-BuLi (15 mmol) in hexanes at −40° C. The resulting solution was stirred from −40 ° C. to −20° C. for 4 h. To this furyllithium solution was added 1.5 eq of the solution of MgBr$_2$ in ether dropwise at −78° C. The resulting solution was stirred at −78° C. for 1 h and warmed to 10° C. gradually and then the arecoline (450 mg, 2.9 mmol) in 20 mL of dry ether was added dropwise to it at −20 (C. The resulting mixture was stirred at −15° C. for another 1 h. The mixture was cooled to about −40° C. and treated slowly with 10% HCl (15 mL). The aqueous layer was separated, extracted with ether (20 mL), and then basified with saturated sodium bicarbonate solution when cooled in an ice bath. The mixture was extracted with ether and the combined organic phase was washed with brine, dried and concentrated under reduced pressure. Flash chromatography gave the trans compound, 78: 185 mg (14%) and a mixture of cis and two other impurities (200 mg, 50% is cis). 79: IR (film) 733, 1012, 1160, 1736, 2790, 2943 cm$^{-1}$; $^1$H NMR (CDCl$_3$) d 1.75–1.92 (m, 1H), 1.99 (dq, 1H, J=3.3, 13.5 Hz), 2.09 (dt, 1H, J=2.7, 12.0 Hz), 2.20 (t, 1H, J=10.8 Hz), 2.32 (s, 3H), 2.81–3.06 (m, 4H), 3.60 (s, 3H), 6.02 (d, 1H, J=3.0 Hz), 6.16 (dd, 1H, J=2.1, 3.0 Hz), 7.28–7.31 (m, 1H); $^{13}$C NMR (CDCl$_3$) d 30.2, 37.4, 46.3, 47.5, 51.9, 55.2, 57.8, 104.7, 110.2, 141.4, 156.9, 173.9; MS m/z 44 (47), 70 (100), 223 (M$^+$, 45).

Example 53

Using procedures similar to those described herein, the following compounds of formula I can be prepared:

Methyl 4β-(4-allylphenyl)-1-methylpiperidine-3α-carboxylate;

Methyl 4β-(4-allylphenyl)-1-methylpiperidine-3β-carboxylate;

Methyl 4β-[4-(2-chlorovinyl)phenyl]-1-methylpiperidine-3α-carboxylate;

Methyl 4β-[4-(2-chlorovinyl)phenyl]-1-methylpiperidine-3β-carboxylate; and

Methyl 4β-(4-trifluoromethylphenyl)-1-methylpiperidine-3β-carboxylate.

Example 54

(+)-5-[4'β-(4-Chlorophenyl)-1-methylpiperid-3'α-ylcarbonyloxy]pentyl 4β-(4-Chlorophenyl)-1-methylpiperidine-3α-carboxylate (82)

To a solution of 110 mg (0.39 mmol) of acid chloride prpared from compound 57, under standard conditions, in 6 mL of dichloromethane was added 13.6 mL (0.13 mmol) of 1,5-pentanediol, a little bit of pyridine and a catalytic amount of DMAP. The resulting mixture was stirred at room temperature overnight, and evaporated. Flash chromatography afforded the product (48 mg, 22%): $[\alpha]_D$ +30.3 ( (c 1.65, $CHCl_3$); IR (film) 822, 1159, 1493, 1728, 2791, 2937 $cm^{-1}$; $^1H$ NMR ($CDCl_3$) d 0.81 (q, 2H, J=7.5 Hz), 1.10–1.34 (m, 4H), 1.72–1.90 (m, 4H), 2.00–2.24 (m, 4H), 2.36 (s, 6H), 2.66–2.78 (m, 2H), 2.85 (dt, 2H, J=3.9, 11.1 Hz), 2.95 (d, 2H, J=11.4 Hz), 3.08 (dd, 2H, J=2.1, 11.1 Hz), 3.65–3.95 (m, 4H), 7.13 (d, 4H, J=8.4 Hz), 7.23 (d, 4H, J=8.4 Hz); $^{13}C$ NMR ($CDCl_3$), 22.0, 28.1, 33.4, 44.4, 46.3, 49.3, 55.9, 58.2, 64.2, 128.7, 129.0, 132.5, 142.1, 173.1; MS m/z 49 (30), 84 (100), 252 (2); Anal. ($C_{31}H_{40}Cl_2N_2O_4$) Calcd: C 64.69, H 7.00, N 4.87; Found: C 64.69, H 6.86, N 4.74.

Example 55

The following illustrate representative pharmaceutical dosage forms, containing a compound of formula I ('Compound X'), for therapeutic or prophylactic use in humans.

| (i) Tablet 1 | mg/tablet |
|---|---|
| 'Compound X' | 100.0 |
| Lactose | 77.5 |
| Povidone | 15.0 |
| Croscarmellose sodium | 12.0 |
| Microcrystalline cellulose | 92.5 |
| Magnesium stearate | 3.0 |
| | 300.0 |

| (ii) Tablet 2 | mg/tablet |
|---|---|
| 'Compound X' | 20.0 |
| Microcrystalline cellulose | 410.0 |
| Starch | 50.0 |
| Sodium starch glycolate | 15.0 |
| Magnesium stearate | 5.0 |
| | 500.0 |

| (iii Capsule | mg/capsule |
|---|---|
| 'Compound X' | 10.0 |
| Colloidal silicon dioxide | 1.5 |
| Lactose | 465.5 |
| Pregelatinized starch | 120.0 |
| Magnesium stearate | 3.0 |
| | 600.0 |

| (iv) Injection 1 (1 mg/ml) | mg/ml |
|---|---|
| 'Compound X' (free acide form) | 1.0 |
| Dibasic sodium phosphate | 12.0 |
| Monobasic sodium phosphate | 0.7 |
| Sodium chloride | 4.5 |
| 1.0 N Sodium hydroxide solution (pH adjustment to 7.0–7.5) | q.s. |
| Water for injection | q.s. ad 1 mL |

| (v) Injection 2 (10 mg/ml) | mg/ml |
|---|---|
| 'Compound X' (free acid form) | 10.0 |
| Monobasic sodium phosphate | 0.3 |
| Dibasic sodium phosphate | 1.1 |
| Polyethylene glycol 400 | 200.0 |
| 01 N Sodium hydroxide solution (pH adjustment to 7.0–7.5) | q.s. |
| Water for injection | q.s. ad 1 mL |

| (vi) Aerosol | mg/can |
|---|---|
| 'Compound X' | 20.0 |
| Oleic acid | 10.0 |
| Trichloromonofluoromethane | 5,000.0 |
| Dichlorodifluoromethane | 10,000.0 |
| Dichlorotetrafluoroethane | 5,000.0 |

The above formulations may be obtained by conventional procedures well known in the pharmaceutical art.

Example 56

Synaptosomal Uptake of [$^3$H]Dopamine

The effect of candidate compounds in antagonizing dopamine high-affinity uptake was determined using a method previously employed. For [$^3$H]DA uptake, dissected rat striata were homogenized with a Teflon-glass pestle in ice-cold 0.32 M sucrose and centrifuged for 10 min at 1000×g. The supernatant was centrifuged at 17,500×g for 20 min. This $P_2$ synaptosomal pellet was resuspended in 30 volumes of ice-cold modified KRH buffer. An aliquot of the synaptosomal suspension was preincubated with the buffer and drug for 30 min at 37° C., and uptake initiated by the addition of [$^3$H]dopamine (5 nM, final concentration). After 5 min, uptake was terminated by adding 5 mL of cold buffer containing glucosamine as a substitute for NaCl and then finally by rapid vacuum filtration over GF-C glass fiber filters, followed by washing with two 5 mL volumes of ice-cold, sodium-free buffer. Radioactivity retained on the filters was determined by liquid scintillation spectrometry. Specific uptake was defined as that which is sensitive to inhibition by 30 μM cocaine. It is identical to that calculated by subtracting the mean of identical tubes incubated at 0° C.

Example 57

Synaptosomal Uptake of [$^3$H]5-Hydroxytryptamine and [$^3$H]Norepinephrine

[$^3$H]5-HT and [$^3$H]NE uptake were measured as outlined in Example 56 using synaptosomes prepared from rat midbrain or parietal and occipital cortices, respectively. The specific uptake of [$^3$H]5-HT and [$^3$H]NE were defined with 10 μM fluoxetine or 3 μM desipramine, respectively.

Example 58

(+)-4β-(4-Chlorophenyl)-1-methylpiperidine-3α-carboxylic Acid Hydrochloride (8)

A solution of 6 (1.0 g, 3.73 mmol) in HCl (6N, 10 mL) was stirred at reflux for 6 h then concentrated to give a white powder corresponding to the title compound (1.0 g, 95%): mp 77–78° C.; [α]D +62° (c 1.0, EtOH); $^1$H NMR (CD$_3$OD) δ 1.98–2.12 (m, 2H), 2.93 (s, 3H), 2.97–3.30 (m, 4H), 3.58 (d, J=12.0 Hz, 1H), 3.75 (d, J=11.7 Hz, 1H), 7.23 (d, J=8.7 Hz, 2H), 7.29 (d, J=8.7 Hz, 2H).

Example 59

(−)-4β-(4-Chlorophenyl)-1-methylpiperidine-3α-carboxylic Acid Hydrochloride (9)

A solution of 7 (800 mg, 2.99 mmol) in HCl (6N, 10 mL) was stirred at reflux for 6 h then concentrated to give a white powder corresponding to the title compound (819 mg, 95%): mp 77–78° C.; [α]D −61° (c 1.0, EtOH); $^1$H NMR (CD$_3$OD) δ 1.98–2.12 (m, 2H), 2.93 (s, 3H), 2.97–3.30 (m, 4H), 3.58 (d, J=12.0 Hz, 1H), 3.75 (d, J=11.7 Hz, 1H), 7.23 (d, J=8.7 Hz, 2H), 7.29 (d, J=8.7 Hz, 2H).

Example 60

(+)-5-[4β-(4-Chlorophenyl)-1-methyl-3α-piperidylcarbonyloxy]pentyl 4β-(4-Chlorophenyl)-1-methylpiperidine-3α-carboxylate (10)

To a stirred suspension of 8 (376 mg, 1.29 mmol) in CH$_2$Cl$_2$ (5 mL) was added oxalyl chloride (0.23 mL, 2.64 mmol) and the suspension was stirred for 2 h until all of the solid had dissolved. The solvent was evaporated to give a white solid as the acid chloride intermediate. The solid was dissolved in CH$_2$Cl$_2$ (10 mL) and treated with TEA (500 μL) followed by 1,5-pentanediol (54 μL, 0.52 mmol), and catalytic amount of DMAP. The resulting solution was stirred at rt overnight. The reaction mixture was diluted with CH$_2$Cl$_2$ (20 mL) washed with aq. NaHCO$_3$ (2×10 mL) dried over Na$_2$SO$_4$ and concentrated. Flash chromatography (CH$_2$Cl$_2$/MeOH/TEA, 90:5:5) gave a solid. The solid was triturated in ether (10 mL) and removed by filtration to give the title compound as an oil (240 mg, 81%): [α]D +30° (c 1.65, CHCl$_3$); $_1$H NMR (CDCl$_3$) δ 0.81 (q, J=7.5 Hz, 2H), 1.10–1.34 (m, 4H), 1.72–1.90 (m, 4H), 2.00–2.24 (m, 4H), 2.36 (s, 6H), 2.66–2.78 (m, 2H), 2.85 (dt, J=3.9, 11.1 Hz, 2H), 2.95 (d, J=11.4 Hz, 2H), 3.08 (dd, J=2.1, 11.1 Hz, 2H), 3.65–3.95 (m, 4H), 7.13 (d, J=8.4 Hz, 4H), 7.23 (d, J=8.4 Hz, 4H). Anal. (C$_{31}$H$_{40}$Cl$_2$N$_2$O$_4$) Calcd: C 64.69, H 7.00, N 4.87; Found: C 64.69, H 6.86, N 4.74.

Example 61

(+)-3-[4β-(4-Chlorophenyl)-1-methyl-3α-piperidylcarbonyloxy]propyl 4β-(4-Chlorophenyl)-1-methylpiperidine-3α-carboxylate (11)

11 was prepared using the general procedure outlined in Example 60. From (+)-4β-(4-chlorophenyl)-1-methylpiperidine-3α-carboxylic acid Hydrochloride (0.20 g, 0.69 mmol) and 1,3-propanediol (22 mL, 0.30 mmol) was obtained the title compound as an oil (135 mg, 82%): [α]D +40.9° (c 0.89, CHCl$_3$); $^1$H NMR (CDCl$_3$) d 1.37 (p, J=6.3 Hz, 2H), 1.73–1.84 (m, 4H), 2.04–2.21 (m, 4H), 2.35 (s, 6H), 2.63–2.75 (m, 2H), 2.84 (dt, J=3.6, 11.4 Hz, 2H), 2.94 (d, J=11.4 Hz, 2H), 3.05 (dd, J=2.1, 11.1 Hz, 2H), 3.50–3.70 (m, 4H), 7.11 (d, J=8.4 Hz, 4H), 7.23 (d, J=8.4 Hz, 4H); Calcd: C 63.62, H 6.63, N, 5.12; Found: C 63.65, H 6.55, N 5.08.

Example 62

(+)-8-[4β-(4-Chlorophenyl)-1-methyl-3α-piperidylcarbonyloxy]octyl 4β-(4-Chlorophenyl)-1-methylpiperidine-3α-carboxylate (12)

12 was prepared using the general procedure outlined in Example 60. From (+)-4β-(4-chlorophenyl)-1-methylpiperidine-3α-:-carboxylic acid Hydrochloride (0.20 g, 0.69 mmol) and 1,8-octanediol (44 mg, 0.30 mmol) was obtained the title compound as an oil (140 mg, 75%): [α]D +40.1° (c 1.02, CHCl$_3$); $^1$H NMR (CDCl$_3$) δ 0.95–1.15 (m, 8H), 1.24–1.38 (m, 4H), 1.74–1.86 (m, 4H), 2.04–2.12 (m, 2H), 2.18 (t, J=11.1 Hz, 2H), 2.35 (s, 6H), 2.67–2.78 (m, 2H), 2.86 (dt, J=3.6, 11.1 Hz, 2H), 2.94 (d, J=11.1 Hz, 2H), 3.09 (dd, J=2.1, 11.1 Hz, 2H), 3.75–3.92 (m, 4H), 7.14 (d, J=8.1 Hz, 4H), 7.24 (d, J=8.7 Hz, 4H); MS m/z 43 (100), 616 (M+, 1); Anal. (C$_{34}$H$_{46}$Cl$_2$N$_2$O$_4$) Calcd: C 66.12, H 7.51, N 4.54; Found: C 66.00, H 7.52, N 4.56.

Example 63

(+)-4-[4β-(4-Chlorophenyl)-1-methyl-3α-piperidylcarbonyloxy]phenyl 4β-(4-Chlorophenyl)-1-methylpiperidine-3α-carboxylate (13)

13 was prepared using the general procedure outlined in Example 60. From (+)-4β-(4-chlorophenyl)-1-methylpiperidine-3α-carboxylic acid Hydrochloride (0.20 g, 0.69 mmol) and hydroquinone (33 mg, 0.30 mmol) was obtained the title compound as an oil (120 mg, 69%): [α]D +97° (c 0.40, CHCl$_3$); $^1$H NMR (CDCl$_3$) δ 1.80–1.92 (m, 4H), 2.06–2.20 (m, 2H), 2.30 (t, J=11.1 Hz, 2H), 2.38 (s, 6H), 2.74–2.86 (m, 2H), 2.98 (d, J=12.0 Hz, 2H), 3.06 (dt, J=3.6, 11.4 Hz, 2H), 3.09 (dd, J=2.4, 11.1 Hz, 2H), 6.53 (s, 4H), 7.18 (d, J=8.4 Hz, 4H), 7.28 (d, J=8.4 Hz, 4H); MS m/z 58 (100), 236 (38), 582 (M+, 0.5); Anal. (C$_{32}$H$_{34}$Cl$_2$N$_2$O$_4$) Calcd: C 66.09, H 5.89, N 4.82; Found: C 66.33, H 5.96, N 4.84.

Example 64

(+)4-{4-[4β-(4-Chlorophenyl)-1-methyl-3α-piperidylcarbonyloxy]phenyl}Phenyl 4β-(4-Chlorophenyl)-1-methylpiperidine-3α-carboxylate (14)

14 was prepared using the general procedure outlined in Example 60. From (+)-4β-(4-chlorophenyl)-1-methylpiperidine-3α-carboxylic acid Hydrochloride (0.20 g, 0.69 mmol) and 4,4'-biphenol (44 mg, 0.23 mmol) was obtained the title compound as an oil (140 mg, 71%): [α]D +127° (c 0.24, CHCl$_3$); 1H NMR (CDCl$_3$) δ 1.84–1.95 (m, 4H), 2.11–2.24 (m, 2H), 2.35 (t, J=11.1 Hz, 2H), 2.41 (s, 6H), 2.80–2.92 (m, 2H), 3.01 (d, J=11.1 Hz, 2H), 3.12 (dt, J=3.3, 11.1 Hz, 2H), 3.28 (dd, J=2.1, 11.4 Hz, 2H), 6.68 (d, J=8.4 Hz, 4H), 7.24 (d, J=8.4 Hz, 4H), 7.31 (d, J=8.4 Hz, 4H), 7.38 (d, J=8.4 Hz, 4H).

Example 65

(+)-5-Hydroxypentyl 4β-(4-Chlorophenyl)-1-methylpiperidine-3α-carboxylate (15)

15 was prepared using the general procedure outlined in Example 60. From (+)-4β-(4-chlorophenyl)-1-methylpiperidine-3α-carboxylic acid Hydrochloride (0.20 g, 0.69 mmol) and 1,5-propanediol (91 μL, 0.87 mmol) was obtained the title compound as a transparent oil (43 mg, 71%): [α]D +24.3° (c 0.64, CHCl$_3$); IR (film) 822, 1729, 2937, 3387 cm−1; 1H NMR (CDCl$_3$) δ 1.05–1.20 (m, 2H), 1.30–1.50 (m, 5H), 1.65–1.85 (m, 2H), 2.05–2.15 (m, 1H), 2.19 (t, J=11.1 Hz, 1H), 2.35 (s, 3H), 2.65–2.78 (m, 1H), 2.85 (dt, J=3.3, 11.4 Hz, 1H), 2.95 (d, J=11.7 Hz, 1H), 3.09 (dd, J=2.1, 11.1 Hz, 1H), 3.58 (t, J=6.6 Hz, 2H), 3.78–3.93 (m, 2H), 7.14 (d, J=8.1 Hz, 2H), 7.24 (d, J=8.4 Hz, 2H); $^{13}$C NMR (CDCl3) 22.1, 28.4, 32.4, 33.2, 44.4, 46.2, 49.2, 55.8, 58.1, 62.7, 64.5, 128.7, 129.0, 132.4, 142.1, 173.2; MS m/z 44 (100), 208 (20), 339 (M+, 3); Anal. ($C_{18}H_{26}ClNO_3$) Calcd: C 63.61, H 7.71, N 4.12; Found: C 63.09, H 7.31, N 4.22.

Example 66

(+)-1,5-{bis-[(4β-(4-Chlorophenyl)-1-methyl-3α-piperidamido]}pentane (16)

16 was prepared using the general procedure outlined in Example 60. From (+)-4β-(4-chlorophenyl)-1-methylpiperidine-3α-carboxylic acid Hydrochloride (600 mg, 2.08 mmol) and 1,5-diaminopentane (116 μL, 0.988 mmol) was obtained the title compound as a white solid (530 mg, 93%): [α]D +56° (c 0.5, EtOH); $^1$H NMR (CDCl$_3$) δ 0.57 (p, J=7.2 Hz, 2H), 1.02 (p, J=7.9 Hz, 4H), 1.6–2.2 (m, 8H), 2.21 (td, J=11.1, 3.9 Hz, 2H), 2.4 (s, 6H), 2.4–2.6 (m, 2H), 2.8 (m, 4H), 2.9–3.1 (m, 4H), 5.13 (bs, 2H), 7.13 (d, J=8.1 Hz, 4H), 7.25 (d, J=8.4 Hz, 4H).

Example 67

(−)-1,5-{bis-[(413-(4-Chlorophenyl)-1-methyl-3α-pipendamido]}pentane (17)

17 was prepared using the general procedure outlined in Example 60. From (−)-4β-(4-chlorophenyl)-1-methylpiperidine-3α-carboxylic acid Hydrochloride (0.20 g, 0.69 mmol) and 1,5-diaminopentane (43 μL, 0.36 mmol) was obtained the title compound as a white solid (90 mg, 43%): [α]D −56° (c 0.5, EtOH); $^1$H NMR (CDCl$_3$) δ 0.57 (p, J=7.2 Hz, 2H), 1.06 (p, J=7.9 Hz, 4H), 1.6–2.2 (m, 8H), 2.29 (td, J=11.1, 3.9 Hz, 2H), 2.4 (s, 6H), 2.4–2.6 (m, 2H), 2.8 (m, 4H), 2.9–3.1 (m, 4H), 5.13 (bs, 2H), 7.13 (d, J=8.1 Hz, 4H), 7.25 (d, J=8.4 Hz 4H); Anal. ($C_{31}H_{42}Cl_2N_4O_2$) Calcd: C 64.91, H 7.38, N 9.77; Found: C 64.95, H 7.32, N 9.50.

Example 68

(+)-1,4-{bis-[(4β-(4-Chlorophenyl)-1-methyl-3α-piperidamido]}butane (18)

18 was prepared using the general procedure outlined in Example 60. From (+)-4β-(4-chlorophenyl)-1-methylpiperidine-3α-carboxylic acid Hydrochloride (0.10 g, 0.35 mmol) and 1,4-diaminobutane (15 μL, 0.15 mmol) was obtained the title compound as a white solid (48 mg, 57%): [α]D +51° (c 0.25, EtOH); $^1$H NMR (CDCl$_3$) δ 0.63 (m, 4H), 1.8–2.0 (m, 8H), 2.15 (td, J=11, 3.0 Hz, 2H), 2.35 (s, 6), 2.3–2.6 (m, 2H), 2.78 (m, 2H), 2.9–3.1 (m, 6H), 5.29 (bs, 2H), 7.14 (d, J=8.7 Hz, 4H), 7.25 (d, J=8.7 Hz, 4H).

Example 69

(−)-1,4-{bis-[(4β-(4-Chlorophenyl)-1-methyl-3α-piperidamido]}butane (19)

19 was prepared using the general procedure outlined in Example 60. From (−)-4β-(4-chlorophenyl)-1-methylpiperidine-3α-carboxylic acid Hydrochloride (0.20 g, 0.69 mmol) and 1,4-diaminobutane (43 μL, 0.36 mmol) was obtained the title compound as a white solid (50 mg, 66%): [α]D −51° (c 0.25, EtOH); $^1$H NMR (CDCl$_3$) δ 0.70 (m, 4H), 1.8–2.0 (m, 8H), 2.15 (td, J=11, 3.0 Hz, 2H), 2.49 (s, 6), 2.3–2.6 (m, 2H), 2.9–3.1 (m, 6H), 5.29 (bs, 2H), 7.14 (d, J=8.7 Hz, 4H), 7.25 (d, , J=8.7 Hz, 4H). Anal. ($C_{30}H_{40}Cl_2N_4O_2$–0.6HCl) Calcd: C 61.97, H 6.95, N 9.64; Found: C 61.76, H 6.96, N 9.87

Example 70

(+)-1,3-{bis-[(4β-(4-Chlorophenyl)-1-methyl-3α-piperidamido]}propane (20)

20 was prepared using the general procedure outlined in Example 60. From (+)-4β-(4-chlorophenyl)-1-methylpiperidine-3α-carboxylic acid Hydrochloride (0.10 g, 0.35 mmol) and 1,3-diaminopropane (15 μL, 0.15 mmol) was obtained the title compound as a white solid (45 mg, 55%): [α]D +58° (c 0.25, EtOH); $^1$H NMR (CDCl$_3$) δ 1.0 (p, J=6.3, 2H), 1.8–2.0 (m, 8H), 2.15 (td, J=11, 3.6 Hz, 2H), 2.35 (s, 6), 2.3–2.6 (m, 4H), 2.78 (m, 2H), 2.9–3.0 (m, 4H), 5.71 (bs, 2H), 7.14 (d, J=8.7 Hz, 4H), 7.25 (d, J=8.7 Hz, 4H).

Example 71

(−)-1,3-{bis-[(4β-(4-Chlorophenyl)-1-methyl-3α-piperidamido]}propane (21)

21 was prepared using the general procedure outlined in Example 60. From (−)-4β-(4-chlorophenyl)-1-methylpiperidine-3α-carboxylic acid Hydrochloride (0.10 g, 0.35 mmol) and 1,3-diaminopropane (13 μL, 0.16 mmol) was obtained the title compound as a white solid (56 mg, 56%): [α]D −66° (c 0.25, EtOH); $^1$H NMR (CDCl$_3$) δ 1.0 (p, J=6.3, 2H), 1.8–2.0 (m, 8H), 2.15 (td, J=11, 3.6 Hz, 2H), 2.35 (s, 6), 2.3–2.6 (m, 4H), 2.78 (m, 2H), 2.9–3.0 (m, 4H), 5.71 (bs, 2H), 7.14 (d, J=8.7 Hz, 4H), 7.25 (d, J=8.7 Hz, 4H. Anal. ($C_{29}H_{38}Cl_2N_4O_2$–0.5HCl) Calcd: C 61.78, H 6.90, N 9.94; Found: C 61.76, H 6.93, N 9.87.

Example 72

(+)-1,6-{bis-[(4β-(4-Chlorophenyl)-1-methyl-3α-piperidamido]}hexane (22)

22 was prepared using the general procedure outlined in Example 60. From (+)-4β-(4-chlorophenyl)-1-methylpiperidine-3α-carboxylic acid Hydrochloride (0.10 g, 0.35 mmol) and 1,6-diaminohexane (19 mg, 0.16 mmol) was obtained the title compound as a white solid (68 mg, 75%): [α]D +50° (c 0.25, EtOH); $^1$H NMR (CDCl$_3$) δ 0.76 (m, 4H), 1.00 (m, 4H), 1.8–2.0 (m, 6H), 2.15 (td, J=11, 3.0 Hz, 2H), 2.35 (s, 6H), 2.3–2.6 (m, 2H), 2.82 (m, 4H), 2.9–3.1 (m, 6H), 5.21 (bs, 2H), 7.14 (d, J=8.7 Hz, 4H), 7.25 (d, J=8.7 Hz, 4H).

Example 73

(−)-1,6-{bis-[(4β-(4-Chlorophenyl)-1-methyl-3α-piperidamido]}hexane (23)

23 was prepared using the general procedure outlined in Example 60. From (−)-4β-(4-chlorophenyl)-1-methylpiperidine-3α-carboxylic acid Hydrochloride (0.10 g, 0.35 mmol) and 1,6-diaminohexane (17 mg, 0.15 mmol) was obtained the title compound as a white solid (50 mg, 57%): [α]D −51° (c 0.25, EtOH); $^1$H NMR (CDCl$_3$) δ 0.78 (m, 4H), 1.02 (m, 4H), 1.8–2.0 (m, 6H), 2.15 (td, J=11, 3.0 Hz, 2H), 2.35 (s, 6H), 2.3–2.6 (m, 2H), 2.82 (m, 4H), 2.9–3.1 (m, 6H), 5.21 (bs, 2H), 7.14 (d, J=8.7 Hz, 4H), 7.25 (d, J=8.7 Hz, 4H). Anal. ($C_{32}H_{44}Cl_2N_4O_2$–0.3HCl) Calcd: C 64.21, H 7.47, N 9.36; Found: C 64.16, H 7.46, N 9.23.

Example 74

(−)-4,4'-{bis-[(4β-(4-Chlorophenyl)-1-methyl-3α-piperidamido]}bispiperidine (24)

24 was prepared using the general procedure outlined in Example 60. From 4β-(4-chlorophenyl)-1-methylpiperidine-3α-carboxylic acid Hydrochloride (0.10 g, 0.35 mmol) and 4,4'-bispiperidine dihydrochloride (40 mg, 0.16 mmol) was obtained the title compound as a white solid (45 mg, 43%): mp 184–185° C.; $^1$H NMR (CDCl3) δ 0.6–1.5 (m, 10H), 1.7–2.3 (m, 10H), 2.35 (m, 6H), 2.6–3.1 (m, 10H), 3.71 (m, 2H), 4.48 (m, 2H), 7.11 (d,J=8.2 Hz, 4H), 7.19 (d, , J=8.2 Hz, 4H).

Example 75

(−)-Methyl 4β-(4-Chlorophenyl)-piperidine-3β-carboxylate (26)

A suspension of (−)-methyl 4β-(4-chlorophenyl)-1-methylpiperidine-3β-carboxylate (300 mg, 1.18 mmol), 1,8-bis-(dimethylamino)-naphthalene (proton sponge, 140 mg, 0.66 mmol) and α-chloroethyl chloroformate (1.0 mL, 9.26 mmol) in $CH_2Cl_2$ (30 mL) was stirred at reflux for 2 h. After cooling to rt, the reaction mixture was diluted with HCl/ether (1M, 20 mL) and the mixture was passed through a silica gel plug and chased with $CH_2Cl_2$ The combined eluents were evaporated to give an oil. This oil was dissolved in MeOH (20 mL) and stirred at reflux for 3 h. The solvent was removed in vacuo, diluted with $CH_2Cl_2$ (20 mL) and washed with $NaHCO_3$ (20 mL). The solvent was dried over $Na_2SO_4$ and evaporated in vacuo to give the title compound as an oil (209 mg, 73.5%): [α]D −143.0° (c 1.30, CHCl3); $^1$H NMR (CDCl3)d 1.62–1.73 (m, 1H), 2.34 (dq, J=3.9, 12.6 Hz, 1H), 2.68–2.84 (m, 2H), 2.93–3.16 (m, 3H), 3.34 (t, J=13.5 Hz, 2H), 3.45 (s, 3H), 7.12 (d, J=8.4 Hz, 2H), 7.26 (d, J=8.4 Hz, 2H); MS m/z 43 (25), 57 (100), 194 (41), 253 (M+, 20).

Example 76

(+)-4β-(4-Chlorophenyl)-1-trifluoroacetamidopiperidine-3α-carboxylic Acid (27)

A solution of (−)-Methyl 4β-(4-chlorophenyl)-piperidine-3β-carboxylate (200 mg, 787 mmol) in HCl (6M, 10 mL) was stirred at reflux for 6 h. The solvent was removed in vacuo to give a white solid as the acid intermediate. This solid was added to a stirred solution of TFAA (1.0 mL) in $CH_2Cl_2$ (5 mL) and the mixture was stirred at rt for 3 h. The solution was diluted with $H_2O$ (20 mL) and extracted with $CH_2Cl_2$ (3×30 mL) dried over $Na_2SO_4$, and removed in vacuo to give an oil. Column Chromatography (MeOH/$CH_2Cl_2$, 1:30) gave the title compound as white foam 230 mg (95%). mp 170–172° C.; $^1$H NMR (CDCl3) δ 1.6 (m, 1H), 1.9 (m, 1H), 2.64–3.0 (m, 3H), 3.1–3.3 (m, 2H), 4.17 (dd, J=14.1, 38 Hz, 1H), 4.63 (dd, J=14.1, 38 Hz, 1H), 7.02 (d, J=8.4 Hz, 2H), 7.19 (d, J=8.4 Hz, 2H) 11.95 (bs, 1H).

Example 77

(+)-1,5-{bis-[(4β-(4-Chlorophenyl)-3α-piperidamido]}pentane (29)

29 was prepared using the general procedure outlined in Example 60. From (+)-4β-(4-chlorophenyl)-1-trifluoroacetamidopiperidine-3α-carboxylic acid (0.13 g, 0.39 mmol) and 1,5-diaminopentane (19 μL, 0.16 mmol) was obtained a yellow solid (90 mg, 75%) as the N-trifluoroacetyl protected intermediate 28: mp 199–203° C. This solid was dissolved in a suspension of $K_2CO_3$ (200 mg) in $H_2O$ (0.5 mL) and MeOH (6.0 mL) and the mixture was stirred for overnight. The solvent was evaporated to half the volume and diluted with $K_2CO_3$ (10% in $H_2O$, 10 mL), and extracted with $CH_2Cl_2$ (3×10 mL). The combined extracts were dried over $Na_2SO_4$ and the solvent was removed in vacuo to give a solid. This solid was triturated in hexanes (10 mL) to give the title compound as a white solid (118 mg, 80%) [α]D +58° (c 0.5, EtOH); mp 207–208° C.; $^1$H NMR (CDCl3) δ 0.60 (p, J=7.2 Hz, 2H), 1.01 (p, J=7.9 Hz, 4H), 1.6–2.2 (m, 4H), 2.28 (td, J=11.1, 3.6 Hz, 2H), 2.8 (m, 4H), 2.95 (m, 6H), 3.21 (m, 4H), 5.10 (bs, 2H), 7.13 (d, J=8.1 Hz, 4H), 7.22 (d, J=8.4 Hz, 4H).

Example 78

(+)-1,5-{bis-[(4β-(4-Chlorophenyl)-1-(2-phenylethyl)-3α-piperidamido]}pentane (30)

A solution of (+)-1,5-{bis-[(4β-(4-chlorophenyl)-3α-piperidamido]}pentane (15 mg, 0.028 mmol), (2-bromoethyl)benzene (15 μL, 0.11 mmol) and TEA (200 mL) in $CH_3CN$ (5 mL) was stirred at reflux for 6 h. The reaction mixture was diluted with $NaHCO_3$ (10 mL) and extracted with $CH_2Cl_2$ (3×10 mL). The combined extracts were dried over $Na_2SO_4$ and the solvent removed in vacuo to give an oil. Column chromatography ($CH_2Cl_2$/MeOH, 20:1) gave the title compound as a white solid (5.0 mg, 24%). $^1$H NMR (CDCl3) δ 0.58 (p, J=7.2 Hz, 2H), 0.99 (p, J=7.9 Hz, 4H), 1.8–2.2 (m, 4H), 2.45 (td, J=11.1, 3.6 Hz, 2H), 2.5 (m, 4H), 2.6–2.9 (m, 12H), 3.0 (m, 2H), 3.10 (m, 4H), 5.21 (bs, 2H), 7.1–7.4 (m, 18H).

Example 79

(−)-1-[9-Fluorenyl-methoxycarbonyl]-5-[4β-(4-chlorophenyl)-1-methylpiperidine-3α-amido]pentyl-1-amine (31)

Oxalyl chloride (1.0 mL) was added dropwise to a stirred suspension of 9 (300 mg, 0.987 mmol) in $CH_2Cl_2$ (5 mL) and the solution was stirred for 2 h until all of the solid had dissolved. The solvent was evaporated to give a white solid as the acid chloride intermediate. The solid was dissolved in $CH_2Cl_2$ (10 mL) and treated with TEA (500 μL) followed by F-moc-1,5-diaminopentane (356 mg, 0.987 mmol). The resulting solution was stirred at rt overnight. The reaction mixture was diluted with $CH_2Cl_2$ (20 mL) washed with aq. $NaHCO_3$ (2×10 mL) dried over $Na_2SO$ and concentrated. Flash chromatography ($CH_2Cl_2$/MeOH, 9:1) gave the title compound as white solid (355 mg, 64%): mp 144–145° C.; [α]D −53° (c 0.25, EtOH); $^1$H NMR (CDCl3) δ 0.8–1.4 (m, 6H ), 1.67 (m, 2H), 2.24 (m, 2H), 2.50 (s, 3H), 2.73 (m, 3H), 2.87 (m, 4H), 4.2 (bm, 2H), 7.2–7.5 (m, 8H), 7.67 (d, J=7.5 Hz, 2H), 7.88 (d, J=7.5 Hz, 2H).

Example 80

(−)-1-(Benzamido)-5-[4β-(4-chlorophenyl)-1-methylpiperidine-3α-amido]pentane (32)

A solution of (−)-1-[9-fluorenyl-methoxycarbonyl]-5-[4β-(4-chlorophenyl)-1-methylpiperidine-3α-amido]-pentyl-1-amine (100 mg, 0.179 mmol) and TEA (2.0 mL) in DMF (4.0 mL) was stirred at rt for 12 h. Benzoyl chloride (25 μL, 0.215 mmol) was added to the reaction mixture and the resulting solution was stirred at rt for 24 h. The solvent was evaporated to give a white solid. The solid was dissolved in CH$_2$Cl$_2$ (10 mL) and washed with aq. NaHCO$_3$ (2×10 mL) dried over Na$_2$SO$_4$ and concentrated. Flash chromatography (CH$_2$Cl$_2$/MeOH, 9:1) gave a solid. The solid was triturated in ether (10 mL) and removed by filtration to give the title compound as a white solid (35 mg, 44%): mp 179–180° C.; $^1$H NMR (CDCl$_3$) δ 1.03 (p, J 7.2 Hz, 2H), 1.21 (p, J=7.2 Hz, 2H), 1.50 (p, J=7.2 Hz, 2H), 2.0–2.4 (m, 8H), 2.8–3.2 (m, 5H), 3.38 (m, 2H), 5.28 (s, 1H), 6.25 (m, 1H), 7.0–7.2 (m, 4H), 7.49 (m, 3H), 7.83 (d, 2H, J=7.5 Hz).

Example 81

(–)-1-(1-Adamantaneamido)-5-[4β-(4-chlorophenyl)-1-methylpiperidine-3α-amido]pentane (33)

33 was prepared using the general procedure outlined in Example 60. From (–)-1-[9-fluorenyl-methoxycarbonyl]-5-[4β-(4-chlorophenyl)-1-methylpiperidine-3α-amido]pentyl-1-amine (0.10 mg, 0.18 mmol) and 1-adamantanecarbonyl chloride (71 mg, 0.36 mmol) was obtained the title compound as white solid (55 mg, 82): mp>220° C.; $^1$H NMR (CDCl$_3$) δ 0.96 (p, J=7.2 Hz, 2H), 1.21 (m, 4H), 1.32 (p, J=6.9 Hz, 2H), 1.6–2.0 (m, 11H), 2.0–2.4 (m, 4H), 2.3–2.5 (m, 5H), 2.84 (m, 2H), 2.98 (m, 2H), 3.11 (m, 3H), 3.47 (m, 1H), 5.23 (bs, 1H), 5.62 (bs, 1H), 7.15 (d, J=7.5 Hz, 2H), 7.26 (d, J=7.5 Hz, 2H).

Example 82

(–)-1-(4-Chlorocinnamido)-5-[4β-(4-chlorophenyl)-1-methylpiperidine-3α-amido]pentane (34)

34 was prepared using the general procedure outlined in Example 60. From (–)-(–)-1-[9-fluorenyl-methoxycarbonyl]-5-[4β-(4-chlorophenyl)-1-methylpiperidine-3α-amido]pentyl-1-amine (100 mg, 0.179 mmol) and 4-chlorocinnamoyl chloride (100 mg, 0.546 mmol) was obtained the title compound as white solid (48 mg, 53%): mp 188–190° C.; $^1$H NMR (CDCl$_3$) δ 0.98 (p, J=7.2 Hz, 2H), 1.19 (p, J=7.2 Hz, 2H), 1.45 (p, J=6.9 Hz, 2H), 1.8–2.2 (m, 4H), 2.34 (s, 3H), 2.49 (m, 1H), 2.8–3.0 (m, 4H), 3.10 (m, 1H), 3.29 (m, 2H), 5.40 (bs, 1H), 6.00 (bs, 1H), 6.49 (d, J=15.6 Hz, 1H), 7.13 (d, J=7.5 Hz, 2H), 7.23 (d, J=7.5 Hz, 2H), 7.33 (d, J=7.5 Hz, 2H), 7.46 (d, J=7.5 Hz, 2H), 7.57 (d, J=15.6 Hz, 1H). Anal. (C$_{27}$H$_{22}$Cl$_2$N$_3$O$_2$-0.25HCl) Calcd: C 63.41, H 6.57, N 8.22; Found: C 63.34, H 6.57, N 8.18.

Example 83

(–)-1-[4β-(4-Chlorophenyl)-1-methylpiperidine-3α-amido]-5-[(+)-3β-(4-chlorophenyl)tropane-2α-amido)pentane (35)

35 was prepared using the general procedure outlined in Example 60. From (–)-1-[9-fluorenyl-methoxycarbonyl]-5-[4β-(4-chlorophenyl)-1-methylpiperidine-3α-amido]pentyl-1-amine (0.10 g, 0.18 mmol) and (–)-3α-(4-chlorophenyl)tropane-2α-acetyl chloride (50 mg, 0.16 mmol) was obtained the title compound as white solid (48 mg, 53%): mp 137–139° C.; $^1$H NMR (CDCl$_3$) δ 0.61 (p, J=7.2 Hz, 2H), 1.2 (m, 4H), 1.8–2.2 (m, 11H), 2.14 (s, 3H), 2.22 (s, 3H), 2.8–3.0 (m, 4H), 3.0–3.2 (m, 5H), 3.35 (m, 2H), 5.40 (bs, 1H), 5.42 (br, 1H), 7.0–7.4 (m, 8H).

Example 84

(+)-4β-(4-Chlorophenyl)-1-methyl-3β-piperidinyl)methanol (36)

LiAlH$_4$ was added to a solution of (+)-4β-(4-chlorophenyl)-1-methylpiperidine-3β-carboxylate (350 mg, 1.31 mmol) in THF (10 mL) and the mixture was stirred at reflux for 8 h. The reaction mixture was diluted dropwise with aq. NaHCO$_3$ (5 mL) and the resulting solid was removed by filtration. The mother liquor was diluted with CH$_2$Cl$_2$ (20 mL), and washed with NaHCO$_3$ (20 mL) and brine (20 mL). The solvent was dried over Na$_2$SO$_4$ and evaporated to give an oil (332 mg, 100%; purity>95% by NMR).; [α]D +60° (c 1.0, CHCl3); $^1$H NMR (CDCl$_3$) δ 1.15 (bs, 1H), 1.7–2.1 (m, 4H), 2.2–2.3 (m, 2H), 2.35 (s, 3H), 2.96 (m, 1H), 3.16 (m, 1H), 3.25 (m, 1H), 3.99 (m, 1H), 7.13 (d, 2H, J=8.7 Hz), 7.20 (d, 1H, J=8.7 Hz).

Example 85

(+)-4,4'-[bis-4β-(4-Chlorophenyl)-1-methyl-3β-piperidinyl)methyl]biphenyl Ether Hydrochloride (37)

A solution of (+)-4β-(4-chlorophenyl)-1-methyl-3β-piperidinyl) methanol (100 mg, 0.394 mmol), MsCl (92 mL, 1.18 mmol) and TEA (119 mL, 1.18 mmol) in CH$_2$Cl$_2$ (10 mL) was stirred at rt for 16 h. The solvent was removed in vacuo to give an oil as the mesyl intermediate. In a separate flask a suspension of KHMDSi (0.5 M, 900 mL, 0.450 mmol) and 4,4'-biphenol (33 mg, 0.180 mmol) in DMF (2 mL) was stirred at rt for 1 h. The solution of 4,4'-biphenol disodium salt was added to the mesyl intermediate and the mixture was stirred at reflux for 3 h. The solvent was diluted with NaOH (1M, 10 mL) and extracted with CH$_2$Cl$_2$ (3×10 mL). The combined extracts were dried over Na$_2$SO$_4$ and evaporated to give an oil. Column chromatography (CH$_2$Cl$_2$/MeOH, 20:1) gave an oil as the title compound as the free base. Hydrochloride salt was prepared by dissolution of the free base in a solution of HCl/ether (1M, 3 mL), filtration, and final trituration of the crude salt with ether (white solid, 30 mg, 24%): mp 205–207° C.; [α]D +58° (c 0.25, CHCl$_3$); $^1$H NMR (CDCl$_3$) δ 1.8–2.5 (m, 8H), 2.2 (m, 2H), 2.35 (s, 6H), 2.4–2.5 (m, 2H), 2.96 (m, 2H), 3.16 (m, 4H), 3.26 (m, 2H), 7.0–7.4 (m 16H).

Example 86

(+)-4,4'-[bis-4β-(4-Chlorophenyl)-1-methyl-3β-piperidinyl)methyl](1,3-adamantaneyl)diphenyl Ether Hydrochloride (38)

38 was prepared using the general procedure outlined in Example 60. From (+)-4β-(4-chlorophenyl)-1-methyl-3β-piperidinyl) methanol (159 mg, 0.625 mmol), 4–4'-(1,3-adamantanediyl)diphenol (100 mg, 0.313 mmol) in CH$_2$Cl$_2$ (2 mL) was obtained the title compound as a white powder (35 mg, 13%): mp 89–92° C.; $^1$H NMR (CDCl$_3$) δ 1.8–2.3 (m, 24H), 2.38 (s, 6H), 2.4–2.5 (m, 2H), 2.96 (m, 2H), 3.16 (m, 4H), 3.26 (m, 2H), 6.76 (bm, 2H), 7.0–7.4 (m 16H).

Incorporation by Reference

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A compound of formula (I):

$$X—L—X^1 \qquad (I)$$

wherein X and X$^1$ are each independently a compound of formula II

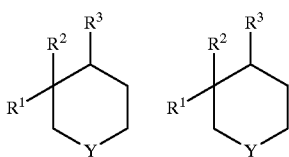

(II)

wherein:

Y is $NR^6$, —$C(R^4)(R^5)$—, or —O—;

$R^1$ is —$C(=O)OR_a$, —$C(=O)N(R_a)_2$, cyano, $(C_1–C_6)$alkyl, $(C_1–C_6)$alkanoyl, $(C_2–C_6)$alkenyl, $(C_2–C_6)$alkynyl, or 1,2,4-oxadiazol-5-yl unsubstituted or substituted at the 3-position by W, wherein any $(C_1–C_6)$alkyl, $(C_1–C_6)$alkanoyl, $(C_2–C_6)$alkenyl, or $(C_2–C_6)$alkynyl is unsubstituted or substituted with 1, 2 or 3 substituents independently selected from the group consisting of halo, nitro, cyano, hydroxy, $(C_1–C_6)$alkoxy, $(C_2–C_6)$acyloxy, trifluoromethyl, $C(=O)OR_b$, $C(=O)NR_cR_d$, $NR_eR_f$, and $S(=O)_nR_g$; and $R^3$ is $(C_6–C_{10})$aryl, 5–10 membered heteroaryl, $(C_6–C_{10})$aryl$(C_1–C_6)$alkyl, 5–10 membered heteroaryl$(C_1–C_6)$alkyl, $(C_6–C_{10})$arylcarbonyl, biphenyl, or 5–10 membered heteroarylcarbonyl, wherein any aryl, biphenyl, or heteroaryl substituent is unsubstituted or substituted on carbon with 1, 2 or 3 substituents independently selected from the group consisting of halo, nitro, cyano, hydroxy, $(C_1–C_6)$alkyl, $(C_2–C_6)$alkenyl, $(C_2–C_6)$alkynyl, $(C_1–C_6)$alkoxy, $(C_2–C_6)$acyloxy, trifluoromethyl, $C(=O)OR_b$, $C(=O)NR_cR_d$, $NR_eR_f$, and $S(=O)_nR_g$; or $R^1$ is —$CH_2$—, or —$CH_2CH_2$—, wherein $R^1$ is attached to a carbon at the ortho position of $R^3$; and $R^3$ is $(C_6–C_{10})$aryl, or 5–10 membered heteroaryl;

$R^2$ is hydrogen or $(C_1–C_6)$alkyl;

$R^4$ and $R^5$ are independently hydrogen or $(C_1–C_6)$alkyl;

$R^6$ is hydrogen, $(C_1–C_6)$alkyl, $(C_1–C_6)$alkanoyl, $(C_2–C_6)$alkenyl, $(C_2–C_6)$alkynyl, trifluoromethyl, aryl, heteroaryl, aryl$(C_1–C_4)$alkyl, heteroaryl$(C_1–C_4)$alkyl, aryl$(C_1–C_4)$alkanoyl, or heteroaryl$(C_1–C_4)$alkanoyl; wherein any $(C_2–C_6)$alkyl, $(C_2–C_6)$alkanoyl, $(C_2–C_6)$alkenyl, or $(C_2–C_6)$alkynyl is unsubstituted or substituted on a carbon other than the carbon attached to the piperidine nitrogen with 1, 2 or 3 substituents independently selected from the group consisting of nitro, cyano, hydroxy, $(C_1–C_6)$alkoxy, $(C_2–C_6)$acyloxy, trifluoromethyl, $C(=O)OR_b$, $C(=O)NR_cR_d$, and $S(=O)_nR_g$;

each n is independently 0, 1 or 2;

W is $(C_1–C_6)$alkyl, or aryl, unsubstituted or substituted with 1, 2, or 3 substituents independently selected from the group consisting of halo, nitro, cyano, hydroxy, $(C_1–C_6)$alkoxy, $(C_2–C_6)$acyloxy, trifluoromethyl, $C(=O)OR_b$, $C(=O)NR_cR_d$, $NR_eR_f$ and $S(=O)_nR_g$;

$R_a$ is $L_2$ hydrogen, $(C_1–C_4)$alkyl, aryl, heteroaryl, aryl$(C_1–C_4)$alkyl, or heteroaryl$(C_1–C_4)$alkyl;

each $R_b$ is independently hydrogen, $(C_1–C_4)$alkyl, aryl, heteroaryl, aryl$(C_1–C_4)$alkyl, or heteroaryl$(C_1–C_4)$alkyl;

each $R_c$ and $R_d$ is independently hydrogen, $(C_1–C_4)$alkyl, aryl, heteroaryl, aryl$(C_1–C_4)$alkyl, or heteroaryl$(C_1–C_4)$alkyl; or, independently, each $NR_cR_d$ together is piperidino, pyrrolidino, or morpholino;

each $R_e$ and $R_f$ is independently hydrogen, $(C_1–C_4)$alkyl, $(C_1–C_4)$alkanoyl, $(C_1–C_4)$alkoxycarbonyl, aryl, heteroaryl, aryl$(C_1–C_4)$alkyl, heteroaryl$(C_1–C_4)$alkyl, aryl$(C_1–C_4)$alkanoyl, or heteroaryl$(C_1–C_4)$alkanoyl; or, independently, each $NR_eR_f$ together is piperidino, pyrrolidino, or morpholino;

each $R_g$ is independently hydrogen, $(C_1–C_4)$alkyl, aryl, heteroaryl, aryl$(C_1–C_4)$alkyl, or heteroaryl$(C_1–C_4)$alkyl; and L is an unbranched $(C_2–C_{12})$alkylene chain, unsubstituted or substituted with one, two, or three substituents selected from the group consisting of $(C_1–C_4)$alkyl, $(C_1–C_4)$alkoxy, hydroxy, oxo, and halo; or L is an unbranched $(C_2–C_{10})$alkylene chain including, within the chain, at least one divalent radical selected from the group consisting of non peroxide oxy (—O—), thio (—S—), sulfinyl, sulfonyl, —OC(=O)—, and —N(R_m)C(=O)—; or L is $R_j$—$(C_2–C_{10}$alkylene)—$R_k$ wherein $R_j$ and $R_k$ are each independently —N(R_m)—, —O—, or —S—; each $R_m$ is independently hydrogen or $(C_1–C_4)$alkyl; or a pharmaceutically acceptable salt thereof.

2. The compound of claim 1 wherein X and $X^1$ each have the same structure.

3. The compound of claim 1 wherein X and $X^1$ each have a different structure.

4. The compound of claim 2 wherein X and $X^1$ are each a compound of formula II wherein Y is $NR^6$.

5. The compound of claim 2 wherein X and $X^1$ are each a compound of formula II wherein $R^1$ is —$C(=O)OR_a$.

6. The compound of claim 1 wherein the compound is selected from the group consisting of:

(+)-5-[4'β-(4-chlorophenyl)-1-methylpiperid-3'α-ylcarbonyloxy]pentyl 4β-(4-chlorophenyl)-1-methylpiperidine-3α-carboxylate;

(+)-5-[4β-(4-chlorophenyl)-1-methyl-3α-piperidylcarbonyloxy]pentyl 4β-(4-chlorophenyl)-1-methylpiperidine-3α-carboxylate;

(+)-3-[4β-(4-chlorophenyl)-1-methyl-3α-piperidylcarbonyloxy]propyl 4β-(4-chlorophenyl)-1-methylpiperidine-3α-carboxylate;

(+)-8-[4β-(4-chlorophenyl)-1-methyl-3α-piperidylcarbonyloxy]octyl 4β-(4-chlorophenyl)-1-methylpiperidine-3α-carboxylate;

(+)-4-[4β-(4-chlorophenyl)-1-methyl-3α-piperidylcarbonyloxy]phenyl 4β-(4-chlorophenyl)-1-methylpiperidine-3α-carboxylate;

(+)-4-{4-[4β-(4-chlorophenyl)-1-methyl-3α-piperidylcarbonyloxy]phenyl}phenyl 4β-(4-chlorophenyl)-1-methylpiperidine-3α-carboxylate;

(+)-1,5-{bis-[(4β-(4-chlorophenyl)-1-methyl-3α-piperidamido]}pentane;

(−)-1,5-{bis-[(4β-(4-chlorophenyl)-1-methyl-3α-piperidamido]}pentane;

(+)-1,4-{bis-[(4β-(4-chlorophenyl)-1-methyl-3α-piperidamido]}butane;

(−)-1,4-{bis-[(4β-(4-chlorophenyl)-1-methyl-3α-piperidamido]}butane;

(+)-1,3-{bis-[(4β-(4-chlorophenyl)-1-methyl-3α-piperidamido]}propane;

(−)-1,3-{bis-[(4β-(4-chlorophenyl)-1-methyl-3α-piperidamido]}propane;

(+)-1,6-{bis-[(4β-(4-chlorophenyl)-1-methyl-3α-piperidamido]}hexane;

(−)-1,6-{bis-[(4β-(4-chlorophenyl)-1-methyl-3α-piperidamido]}hexane;

(−)-4,4'-{bis-[(4β-(4-chlorophenyl)-1-methyl-3α-piperidamido]}bispiperidine;

(+)-1,5-{bis-[(4β-(4-chlorophenyl)-3α-piperidamido]}pentane;

(+)-1,5-{bis-[(4β-(4-chlorophenyl)-1-(2-phenylethyl)-3α-piperidamido]}pentane;

(+)-4,4'-[bis-4β-(4-chlorophenyl)-1-methyl-3β-piperidinyl)methyl]biphenyl ether hydrochloride; and (+)-4,4'-[bis-4β-(4-chlorophenyl)-1-methyl-3β-piperidinyl)methyl](1,3-adamantaneyl)diphenyl ether hydrochloride.

7. The compound of claim 2 wherein X and $X^1$ are each a compound of formula II wherein $R^1$ is $(C_1-C_6)$alkyl, $(C_1-C_6)$alkanoyl, $(C_2-C_6)$alkenyl, or 1,2,4-oxadiazol-5-yl optionally substituted at the 3-position by W, wherein any $(C_1-C_6)$alkyl, $(C_1-C_6)$alkanoyl, $(C_2-C_6)$alkenyl, or $(C_2-C_6)$alkynyl is unsubstituted or substituted with 1, 2 or 3 substituents independently selected from the group consisting of halo, nitro, cyano, hydroxy, $(C_1-C_6)$alkoxy, $(C_2-C_6)$acyloxy, trifluoromethyl, $C(=O)OR_b$, $C(=O)NR_cR_d$, $NR_eR_f$, and $S(=O)_nR_g$.

8. The compound of claim 2 wherein X and $X^1$ are each a compound of formula II wherein $R^3$ is $(C_6-C_{10})$aryl, or biphenyl; wherein any aryl or biphenyl is unsubstituted or substituted on carbon with 1, 2 or 3 substituents independently selected from the group consisting of halo, nitro, cyano, hydroxy, $(C_1-C_6)$alkyl, $(C_2-C_6)$alkenyl, $(C_2-C_6)$alkynyl, $(C_1-C_6)$alkoxy, $(C_2-C_6)$acyloxy, trifluoromethyl, $C(=O)OR_b$, $C(=O)NR_cR_d$, $NR_eR_f$, and $S(=O)_nR_g$.

9. The compound of claim 2 wherein X and $X^1$ are each a compound of formula II wherein $R^2$ is hydrogen.

10. The compound of claim 2 wherein X and $X^1$ are each a compound of formula II wherein $R^6$ is hydrogen, $(C_1-C_6)$alkyl, or aryl$(C_1-C_4)$alkyl; wherein any aryl is unsubstituted or substituted with 1, 2 or 3 substituents independently selected from the group consisting of nitro, cyano, hydroxy, $(C_1-C_6)$alkoxy, $(C_2-C_6)$acyloxy, trifluoromethyl, $C(=O)OR_b$, $C(=O)NR_cR_d$, and $S(=O)_nR_g$.

11. The compound of claim 3 wherein at least one of X and $X^1$ is a compound of formula II wherein Y is $NR^6$.

12. The compound of claim 3 wherein $R^1$ in X is $—C(=O)OR_a$.

13. The compound of claim 3 wherein at least one of X and $X^1$ is a compound of formula II wherein $R^1$ is $(C_1-C_6)$alkyl, $(C_1-C_6)$alkanoyl, $(C_2-C_6)$alkenyl, or 1, 2, 4-oxadiazol-5-yl optionally substituted at the 3-position by W, wherein any $(C_1-C_6)$alkyl, $(C_1-C_6)$alkanoyl, $(C_2-C_6)$alkenyl, or $(C_2-C_6)$alkynyl is unsubstituted or substituted with 1, 2 or 3 substituents independently selected from the group consisting of halo, nitro, cyano, hydroxy, $(C_1-C_6)$alkoxy, $(C_2-C_6)$acyloxy, trifluoromethyl, $C(=O)OR_b$, $C(=O)NR_cR_d$, $NR_eR_f$, and $S(=O)_nR_g$.

14. The compound of claim 3 wherein at least one of X and $X^1$ is a compound of formula II wherein $R^3$ is $(C_6-C_{10})$aryl, or biphenyl; wherein any aryl or biphenyl is unsubstituted or substituted on carbon with 1, 2 or 3 substituents independently selected from the group consisting of halo, nitro, cyano, hydroxy, $(C_1-C_6)$alkyl, $(C_2-C_6)$alkenyl, $(C_2-C_6)$alkynyl, $(C_1-C_6)$alkoxy, $(C_2-C_6)$acyloxy, trifluoromethyl $C(=O)OR_b$, $C(=O)NR_cR_d$, $NR_eR_f$, and $S(=O)_nR_g$.

15. The compound of claim 3 wherein at least one of X and $X^1$ is a compound of formula II wherein $R^2$ is hydrogen.

16. The compound of claim 3 wherein at least one of X and $X^1$ is a compound of formula II wherein $R^6$ is hydrogen, $(C_1-C_6)$alkyl, or aryl$(C_1-C_4)$alkyl; wherein any aryl is unsubstituted or substituted with 1, 2 or 3 substituents independently selected from the group consisting of nitro, cyano, hydroxy, $(C_1-C_6)$alkoxy, $(C_2-C_6)$acyloxy, trifluoromethyl, $C(=O)OR_b$, $C(=O)NR_cR_d$, and $S(=O)_nR_g$.

17. The compound of claim 1 wherein L is an unbranched $(C_2-C_{12})$alkylene chain.

18. The compound of claim 1 wherein L is an unbranched $(C_2-C_{10})$alkylene chain comprising within the chain, 1 or 2 divalent radicals selected from the group consisting of non peroxide oxy (—O—), thio (—S—), sulfinyl, sulfonyl, —OC(=O)—, and —NHC(=O)—.

19. The compound of claim 1 wherein L is $R_i$—$(C_2-C_{10})$—$R_k$, wherein $R_i$ and $R_k$ are each independently —N$(R_m)$—, —O—, or —S—; and $R_m$ is hydrogen or $(C_1-C_4)$alkyl.

20. The compound of claim 1 wherein L is attached to X and $X^1$ through $R_1$.

21. The compound of claim 12 wherein each $R^1$ is —C(=O)$OR_a$ and each $R_a$ is L.

22. The compound of claim 1 wherein each $R^1$ is —C(=O)N$(R_a)_2$ and each $R_a$ is L.

23. The compound of claim 1 wherein each Y is $NR^6$, and L is attached to X and $X^1$ by replacing each $R^6$ with a bond to L.

24. The compound of claim 1 wherein L is attached to X and $X^1$ through a ring carbon of $R^3$.

25. The compound of claim 21 or 22 wherein X and $X^1$ are each (−)-methyl 4β-(4-vinylphenyl)-1-methylpiperidine-3β-carboxylate.

26. The compound of claim 1 wherein X and $X^1$ are each individually selected from (−)-Methyl 4β-(4-bromophenyl)-1-ethylpiperidine-3β-carboxylate; (−)-Methyl 4β-(4-vinylphenyl)-1-methylpiperidine-3β-carboxylate; (±)-Methyl 4β-(2-naphthyl)-1-methylpiperidine-3β-carboxylate; and (±)-Methyl 4-(2-naphthyl)-1-methylpiperidine-3-carboxylate; or a pharmaceutically acceptable salt thereof.

27. The compound of claim 1 wherein X and $X^1$ are each (+) 4β-(4-chlorophenyl)-1-methylpiperidine-3α-carboxylate.

28. The compound of claim 27 wherein L is an unbranched $(C_2-C_{12})$alkylene chain.

29. The compound of claim 1 wherein X and $X^1$ are each (−)-methyl 4β-(4-vinylphenyl)-1-methylpiperidine-3β-carboxylate.

30. The compound of claim 29 wherein L is an unbranched $(C_2-C_{12})$alkylene chain that forms ester bonds with the 3β-carboxylate groups on X and $X^1$.

31. A pharmaceutical composition comprising a compound of claim 1; and a pharmaceutically acceptable diluent or carrier.

32. A method of treating drug addiction in a human comprising administering to said human a pharmaceutically effective dose of a compound of claim 1.

33. The method of claim 32 wherein the drug is cocaine.

34. A compound selected from the group consisting of:

(+)-methyl (2-E)-3-[4(-(4-chlorophenyl)-1-methyl-3(-piperidyl)]prop-2-enoate;

(+)-methyl 3-[4(-(4-chlorophenyl)-1-methyl-3(-piperidyl]propanoate;

(+)-3-[4(-(4-chlorophenyl)-1-methyl-3)-piperidyl]propan-1-ol;

(+)-5-[4β-(4-chlorophenyl)-1-methyl-3-piperidyl]-3-methyl-1,2,4-oxadiazole;

(+)-5-[4β-(4-chlorophenyl)-1-methyl-3-piperidyl]-3-phenyl-1,2,4-oxadiazole;

(+)-1-[4(-(4-chlorophenyl)-1-methyl-3-piperidyl]propan-1-one;

(+)-5-hydroxypentyl 4β-(4-chlorophenyl)-1-methylpiperidine-3α-carboxylate;

(−)-1-[9-fluorenyl-methoxycarbonyl]-5-[4β-(4-chlorophenyl)-1-methylpiperidine-3α-amido]pentyl-1-amine;

(−)-1-(benzamido)-5-[4β-(4-chlorophenyl)-1-methylpiperidine-3α-amido]pentane;

(−)-1-(1-adamantaneamido)-5-[4β-(4-chlorophenyl)-1-methylpiperidine-3α-amido]pentane;

(−)-1-(4-chlorocinnamido)-5-[4β-(4-chlorophenyl)-1-methylpiperidine-3α-amido]pentane; and (−)-1-[4β-(4-chlorophenyl)-1-methylpiperidine-3α-amido]-5-[(+)-3β-(4-chlorophenyl)tropane-2α-amido)pentane.

\* \* \* \* \*